(12) United States Patent
Anderson et al.

(10) Patent No.: US 10,126,282 B2
(45) Date of Patent: Nov. 13, 2018

(54) YIELD ESTIMATION

(71) Applicant: Deere and Company, Moline, IL (US)

(72) Inventors: Noel W. Anderson, Fargo, ND (US);
James J. Phelan, Bettendorf, IA (US);
Dohn W. Pfeiffer, Bettendorf, IA (US)

(73) Assignee: Deere & Company, Moline, IL (US)

( * ) Notice: Subject to any disclaimer, the term of this patent is extended or adjusted under 35 U.S.C. 154(b) by 377 days.

(21) Appl. No.: 14/822,848

(22) Filed: Aug. 10, 2015

(65) Prior Publication Data

US 2016/0084813 A1    Mar. 24, 2016

Related U.S. Application Data

(63) Continuation-in-part of application No. 14/616,571, filed on Feb. 6, 2015.

(60) Provisional application No. 62/054,187, filed on Sep. 23, 2014.

(51) Int. Cl.
| | | |
|---|---|---|
| *G01V 3/38* | (2006.01) | |
| *G01N 33/02* | (2006.01) | |
| *A01D 41/127* | (2006.01) | |
| *G01V 99/00* | (2009.01) | |

(52) U.S. Cl.
CPC ......... *G01N 33/025* (2013.01); *A01D 41/127* (2013.01); *A01D 41/1271* (2013.01); *G01V 99/00* (2013.01)

(58) Field of Classification Search
CPC ............ A01D 41/127; A01D 41/1271; G01N 33/025; G01V 99/00
USPC .......................................................... 702/5
See application file for complete search history.

(56) References Cited

U.S. PATENT DOCUMENTS

| | | | | |
|---|---|---|---|---|
| 6,185,990 B1* | 2/2001 | Missotten | ............ | A01B 79/005 |
| | | | | 324/691 |
| 9,372,109 B2* | 6/2016 | Acheson | ............... | G01G 11/003 |
| 9,468,140 B2* | 10/2016 | Madsen | ............... | A01B 69/001 |
| 9,635,811 B2* | 5/2017 | Ricketts | ............... | A01D 45/021 |
| 9,639,903 B2* | 5/2017 | Rosa | ....................... | G06Q 50/02 |
| 9,668,414 B2* | 6/2017 | Calmer | ............... | A01D 45/025 |

(Continued)

FOREIGN PATENT DOCUMENTS

| | | |
|---|---|---|
| EP | 0960558 | 12/1999 |
| EP | 1238579 | 9/2002 |

(Continued)

OTHER PUBLICATIONS

EP Search Report for 1518512.3-1656 dated Jun. 3, 2016.

(Continued)

*Primary Examiner* — Mohammed Shamsuzzaman
(74) *Attorney, Agent, or Firm* — Rathe Lindenbaum LLP

(57) ABSTRACT

A method and apparatus estimate yield. A first signal is received that indicates an aggregate yield measured by an aggregate yield sensor during a measurement interval. A second signal is received that indicates a plurality of geo-referenced regions across which a harvester has traveled prior to the measurement interval. The method and apparatus allocate, to each of at least two geo-referenced regions, an aggregate yield portion allocation based upon different travel times for crops to the aggregate yield sensor and pre-harvest weighting data value differences amongst the at least two georeferenced regions. The aggregate yield portion allocations are output.

17 Claims, 19 Drawing Sheets

(56) References Cited

U.S. PATENT DOCUMENTS

| | | | | |
|---|---|---|---|---|
| 9,872,433 | B2* | 1/2018 | Acheson | A01D 41/127 |
| 2002/0091458 | A1* | 7/2002 | Moore | A01B 79/005 |
| | | | | 700/110 |
| 2007/0050116 | A1* | 3/2007 | Jernigan | A01D 46/243 |
| | | | | 701/50 |
| 2010/0036696 | A1 | 2/2010 | Lang | |
| 2010/4035752 | | 2/2014 | Johnson | |
| 2014/0129146 | A1 | 5/2014 | Romier | |
| 2014/0236381 | A1* | 8/2014 | Anderson | A01D 75/00 |
| | | | | 701/1 |
| 2014/0249893 | A1* | 9/2014 | McClure | G09B 29/007 |
| | | | | 705/7.39 |
| 2015/0293029 | A1* | 10/2015 | Acheson | G01N 33/0098 |
| | | | | 356/51 |
| 2016/0084987 | A1* | 3/2016 | Dybro | G01V 99/00 |
| | | | | 702/5 |
| 2017/0016870 | A1* | 1/2017 | McPeek | G01N 33/0098 |
| 2017/0089742 | A1* | 3/2017 | Bruns | A01D 41/1273 |

FOREIGN PATENT DOCUMENTS

| | | |
|---|---|---|
| EP | 2529610 | 12/2012 |
| GB | 2350275 | 11/2000 |

OTHER PUBLICATIONS

EP Search Report for 1518512.3-1656 dated Jun. 3, 2018.
EP Search Report for 15185811.5-1656 dated Feb. 23, 2016.
EP Search Report for 1518512.3-1656 dated Feb. 23, 2016.
European Search Report dated Feb. 23, 2016 for EP15185809.

* cited by examiner

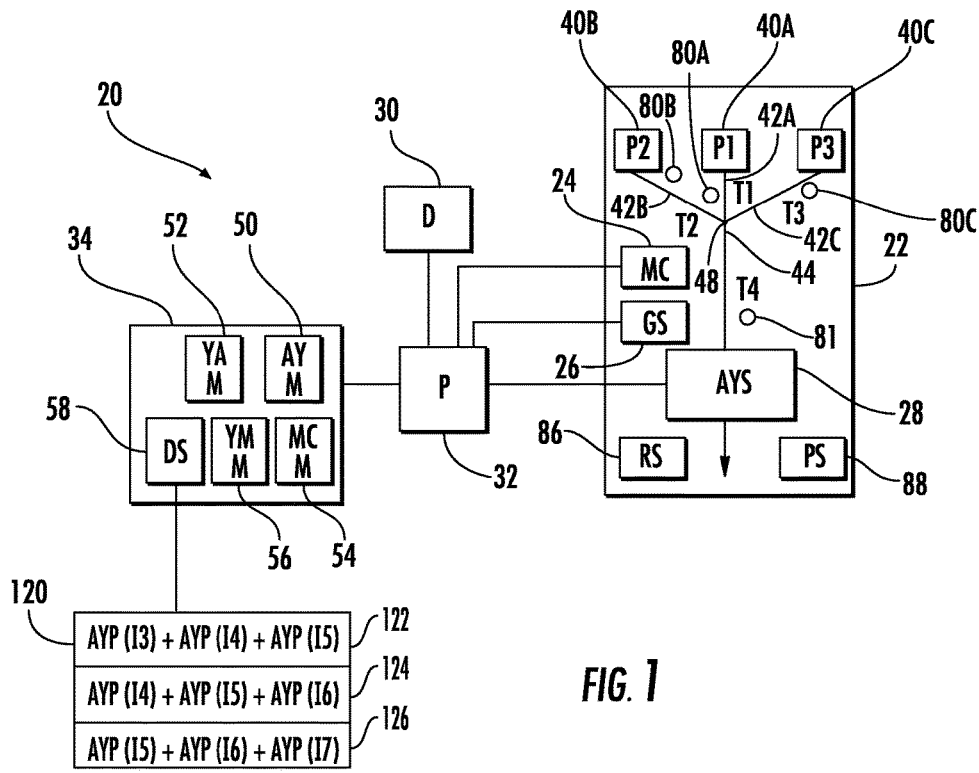
FIG. 1
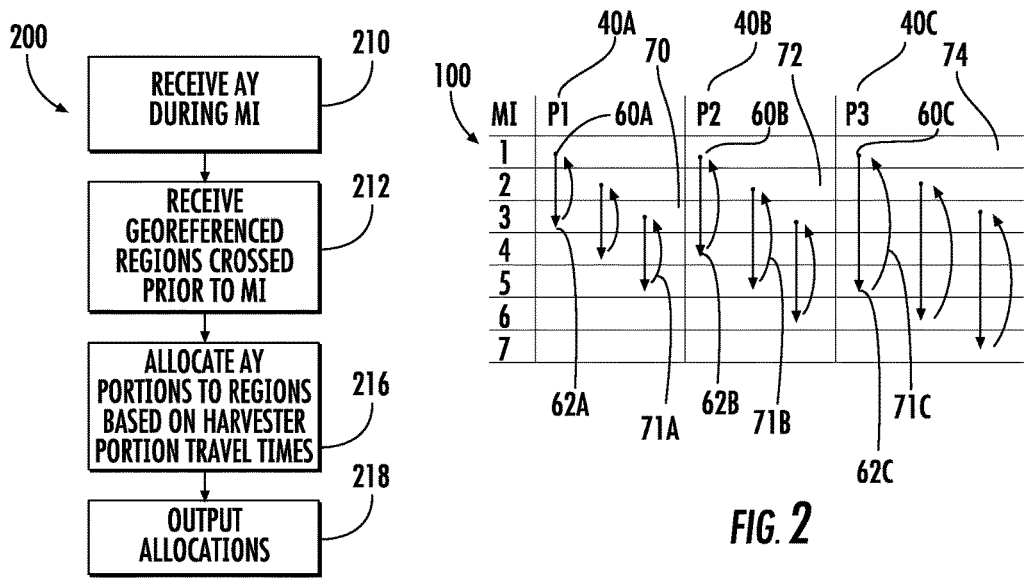
FIG. 2
FIG. 3

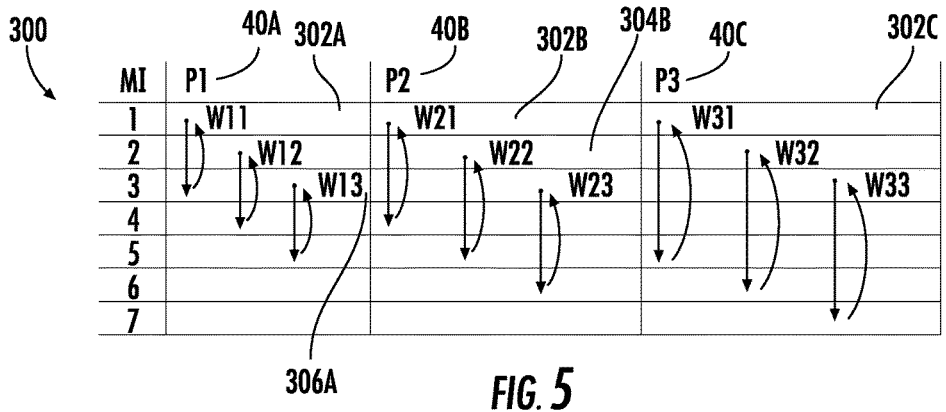
FIG. 5
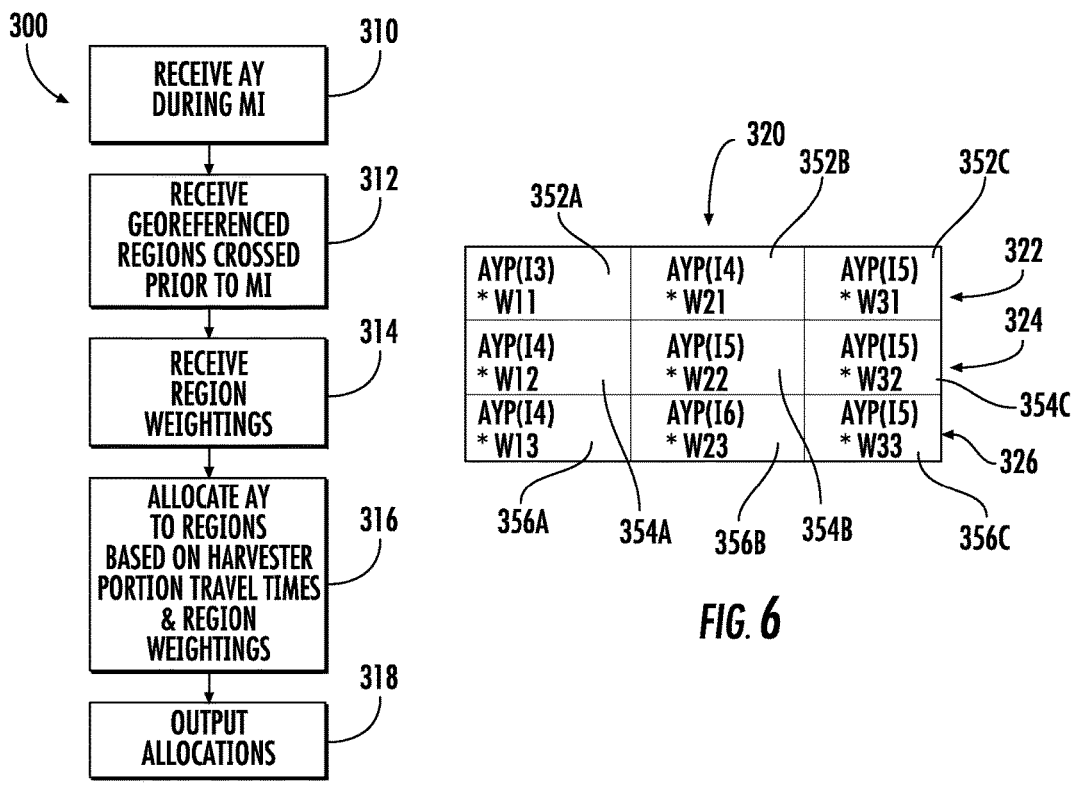
FIG. 4
FIG. 6

749

| RANK | ROW 1 | ROW 2 | ROW 3 | ROW 4 | ROW 5 | ROW 6 | ROW 7 | ROW 8 | NOTES |
|---|---|---|---|---|---|---|---|---|---|
| 1 | 7.0 | 5.0 | 3.0 | 1.0 | 1.0 | 3.0 | 5.0 | 7.0 | T=0 |
| 2 | 7.2 | 5.2 | 3.2 | 1.2 | 1.2 | 3.2 | 5.2 | 7.2 | |
| 3 | 7.4 | 5.4 | 3.4 | 1.4 | 1.4 | 3.4 | 5.4 | 7.4 | |
| 4 | 7.6 | 5.6 | 3.6 | 1.6 | 1.6 | 3.6 | 5.6 | 7.6 | |
| 5 | 7.8 | 5.8 | 3.8 | 1.8 | 1.8 | 3.8 | 5.8 | 7.8 | |
| 6 | 8.0 | 6.0 | 4.0 | 2.0 | 2.0 | 4.0 | 6.0 | 8.0 | |
| 7 | 8.2 | 6.2 | 4.2 | 2.2 | 2.2 | 4.2 | 6.2 | 8.2 | |
| 8 | 8.4 | 6.4 | 4.4 | 2.4 | 2.4 | 4.4 | 6.4 | 8.4 | |
| 9 | 8.6 | 6.6 | 4.6 | 2.6 | 2.6 | 4.6 | 6.6 | 8.6 | |
| 10 | 8.8 | 6.8 | 4.8 | 2.8 | 2.8 | 4.8 | 6.8 | 8.8 | |
| 11 | 9.0 | 7.0 | 5.0 | 3.0 | 3.0 | 5.0 | 7.0 | 9.0 | |
| 12 | 9.2 | 7.2 | 5.2 | 3.2 | 3.2 | 5.2 | 7.2 | 9.2 | |
| 13 | 9.4 | 7.4 | 5.4 | 3.4 | 3.4 | 5.4 | 7.4 | 9.4 | |
| 14 | 9.6 | 7.6 | 5.6 | 3.6 | 3.6 | 5.6 | 7.6 | 9.6 | |
| 15 | 9.8 | 7.8 | 5.8 | 3.8 | 3.8 | 5.8 | 7.8 | 9.8 | |
| 16 | 10.0 | 8.0 | 6.0 | 4.0 | 4.0 | 6.0 | 8.0 | 10.0 | |
| 17 | 10.2 | 8.2 | 6.2 | 4.2 | 4.2 | 6.2 | 8.2 | 10.2 | |
| 18 | 10.4 | 8.4 | 6.4 | 4.4 | 4.4 | 6.4 | 8.4 | 10.4 | |
| 19 | 10.6 | 8.6 | 6.6 | 4.6 | 4.6 | 6.6 | 8.6 | 10.6 | |
| 20 | 10.8 | 8.8 | 6.8 | 4.8 | 4.8 | 6.8 | 8.8 | 10.8 | |
| 21 | 11.0 | 9.0 | 7.0 | 5.0 | 5.0 | 7.0 | 9.0 | 11.0 | |
| 22 | 11.2 | 9.2 | 7.2 | 5.2 | 5.2 | 7.2 | 9.2 | 11.2 | |
| 23 | 11.4 | 9.4 | 7.4 | 5.4 | 5.4 | 7.4 | 9.4 | 11.4 | |
| 24 | 11.6 | 9.6 | 7.6 | 5.6 | 5.6 | 7.6 | 9.6 | 11.6 | |
| 25 | 11.8 | 9.8 | 7.8 | 5.8 | 5.8 | 7.8 | 9.8 | 11.8 | |
| 26 | 12.0 | 10.0 | 8.0 | 6.0 | 6.0 | 8.0 | 10.0 | 12.0 | |
| 27 | 12.2 | 10.2 | 8.2 | 6.2 | 6.2 | 8.2 | 10.2 | 12.2 | |
| 28 | 12.4 | 10.4 | 8.4 | 6.4 | 6.4 | 8.4 | 10.4 | 12.4 | |
| 29 | 12.6 | 10.6 | 8.6 | 6.6 | 6.6 | 8.6 | 10.6 | 12.6 | |
| 30 | 12.8 | 10.8 | 8.8 | 6.8 | 6.8 | 8.8 | 10.8 | 12.8 | |
| 31 | 13.0 | 11.0 | 9.0 | 7.0 | 7.0 | 9.0 | 11.0 | 13.0 | |
| 32 | 13.2 | 11.2 | 9.2 | 7.2 | 7.2 | 9.2 | 11.2 | 13.2 | |
| 33 | 13.4 | 11.4 | 9.4 | 7.4 | 7.4 | 9.4 | 11.4 | 13.4 | |
| 34 | 13.6 | 11.6 | 9.6 | 7.6 | 7.6 | 9.6 | 11.6 | 13.6 | |
| 35 | 13.8 | 11.8 | 9.8 | 7.8 | 7.8 | 9.8 | 11.8 | 13.8 | |
| 36 | 14.0 | 12.0 | 10.0 | 8.0 | 8.0 | 10.0 | 12.0 | 14.0 | |

FIG. 10

| TIME SEC | ROW 1 | ROW 2 | ROW 3 | ROW 4 | ROW 5 | ROW 6 | ROW 7 | ROW 8 | YM |
|---|---|---|---|---|---|---|---|---|---|
| 1 | 7 | 5 | 3 | 1 | 1 | 3 | 5 | 7 | 0 |
| 2 | 8 | 6 | 4 | 2 | 2 | 4 | 6 | 8 | 0 |
| 3 | 9 | 7 | 5 | 3 | 3 | 5 | 7 | 9 | 0 |
| 4 | 10 | 8 | 6 | 4 | 4 | 6 | 8 | 10 | 0 |
| 5 | 11 | 9 | 7 | 5 | 5 | 7 | 9 | 11 | 0 |
| 6 | 12 | 10 | 8 | 6 | 6 | 8 | 10 | 12 | 0 |
| 7 | 13 | 11 | 9 | 7 | 7 | 9 | 11 | 13 | 0 |
| 8 | 14 | 12 | 10 | 8 | 8 | 10 | 12 | 14 | 0 |
| 9 | 15 | 13 | 11 | 9 | 9 | 11 | 13 | 15 | 0 |
| 10 | 16 | 14 | 12 | 10 | 10 | 12 | 14 | 16 | 0 |
| 11 | 17 | 15 | 13 | 11 | 11 | 13 | 15 | 17 | 1 |
| 12 | 18 | 16 | 14 | 12 | 12 | 14 | 16 | 18 | 2 |
| 13 | 19 | 17 | 15 | 13 | 13 | 15 | 17 | 19 | 3 |
| 14 | 20 | 18 | 16 | 14 | 14 | 16 | 18 | 20 | 4 |
| 15 | 21 | 19 | 17 | 15 | 15 | 17 | 19 | 21 | 5 |
| 16 | 22 | 20 | 18 | 16 | 16 | 18 | 20 | 22 | 6 |
| 17 | 23 | 21 | 19 | 17 | 17 | 19 | 21 | 23 | 7 |
| 18 | 24 | 22 | 20 | 18 | 18 | 20 | 22 | 24 | 8 |
| 19 | 25 | 23 | 21 | 19 | 19 | 21 | 23 | 25 | 9 |
| 20 | 26 | 24 | 22 | 20 | 20 | 22 | 24 | 26 | 10 |
| 21 | 27 | 25 | 23 | 21 | 21 | 23 | 25 | 27 | 11 |
| 22 | 28 | 26 | 24 | 22 | 22 | 24 | 26 | 28 | 12 |
| 23 | 29 | 27 | 25 | 23 | 23 | 25 | 27 | 29 | 13 |
| 24 | 30 | 28 | 26 | 24 | 24 | 26 | 28 | 30 | 14 |
| 25 | 31 | 29 | 27 | 25 | 25 | 27 | 29 | 31 | 15 |
| 26 | 32 | 30 | 28 | 26 | 26 | 28 | 30 | 32 | 16 |
| 27 | 33 | 31 | 29 | 27 | 27 | 29 | 31 | 33 | 17 |
| 28 | 34 | 32 | 30 | 28 | 28 | 30 | 32 | 34 | 18 |
| 29 | 35 | 33 | 31 | 29 | 29 | 31 | 33 | 35 | 19 |
| 30 | 36 | 34 | 32 | 30 | 30 | 32 | 34 | 36 | 20 |
| 31 | 37 | 35 | 33 | 31 | 31 | 33 | 35 | 37 | 21 |
| 32 | 38 | 36 | 34 | 32 | 32 | 34 | 36 | 38 | 22 |
| 33 | 39 | 37 | 35 | 33 | 33 | 35 | 37 | 39 | 23 |
| 34 | 40 | 38 | 36 | 34 | 34 | 36 | 38 | 40 | 24 |
| 35 | 41 | 39 | 37 | 35 | 35 | 37 | 39 | 41 | 25 |
| 36 | 42 | 40 | 38 | 36 | 36 | 38 | 40 | 42 | 26 |
| 37 | 43 | 41 | 39 | 37 | 37 | 39 | 41 | 43 | 27 |
| 38 | 44 | 42 | 40 | 38 | 38 | 40 | 42 | 44 | 28 |
| 39 | 45 | 43 | 41 | 39 | 39 | 41 | 43 | 45 | 29 |
| 40 | 46 | 44 | 42 | 40 | 40 | 42 | 44 | 46 | 30 |

*FIG. 11*

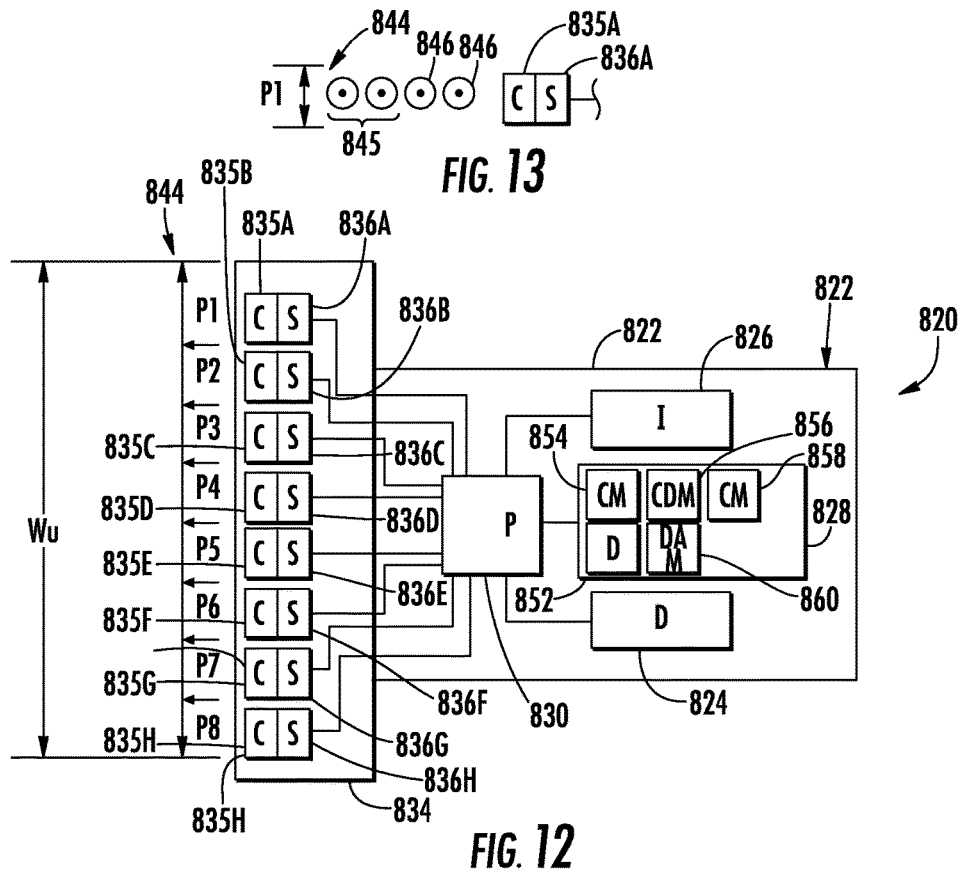
FIG. 13
FIG. 12
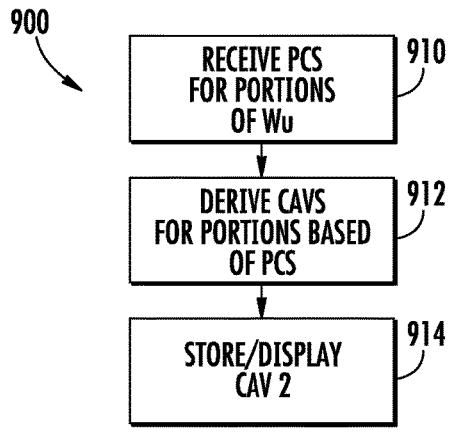
FIG. 14
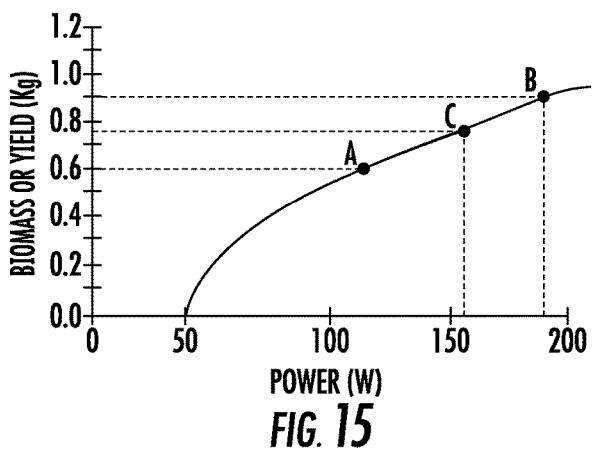
FIG. 15

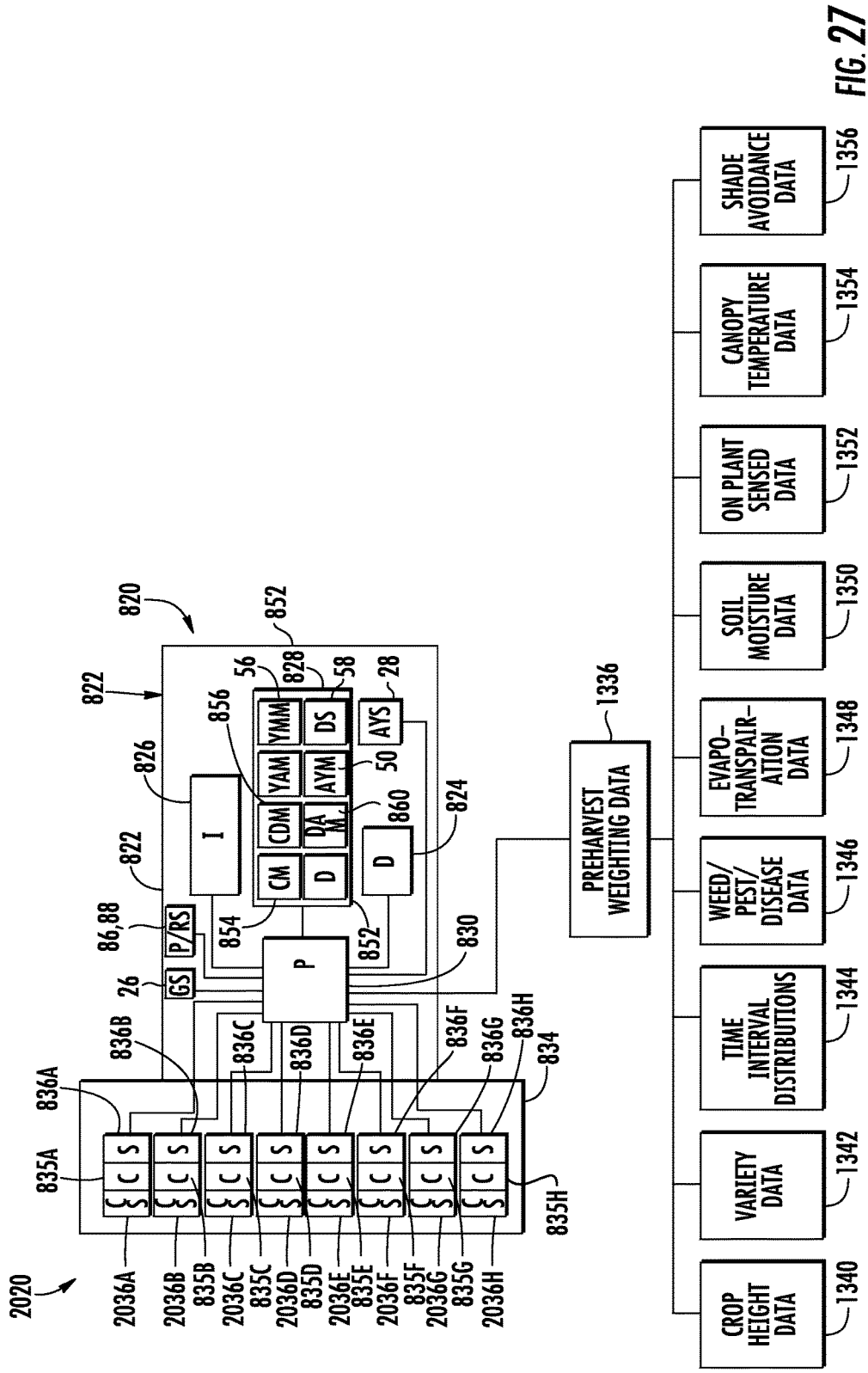

YIELD ESTIMATION

The present application claims priority under 35 USC Section 120 from the U.S. Provisional Patent Application Ser. No. 62/054,187 filed on Sep. 23, 2014 and entitled AGGREGATE YIELD ALLOCATION, the full disclosure of which is hereby incorporated by reference. The present application claims priority under 35 USC Section 120 from the pending U.S. patent application Ser. No. 14/616,571 filed on Feb. 6, 2015 and entitled YIELD ESTIMATION, the full disclosure of which is hereby incorporated by reference.

BACKGROUND

Some harvesters sense an aggregate yield being harvested across a width of a harvesting head. The aggregate yield data assists in the crop management. Unfortunately, aggregate yield data is often inaccurate.

BRIEF DESCRIPTION OF THE DRAWINGS

FIG. 1 is a schematic diagram of an example aggregate yield allocation system.

FIG. 2 is a schematic diagram of an example aggregate yield allocation scheme.

FIG. 3 is a flow diagram of an example aggregate yield allocation method.

FIG. 4 is a flow diagram of another example aggregate yield allocation method employing weightings.

FIG. 5 is a schematic diagram of another example aggregate yield allocation scheme output from the method of FIG. 4.

FIG. 6 is a diagram of an example yield map output by an example yield allocation system carrying out the method of FIG. 4.

FIG. 10 is a diagram of an example field being harvested by the harvester of FIG. 7, indicating feeder house arrival times for grain from different row units.

FIG. 11 is a diagram of an example aggregate yield allocation scheme.

FIG. 12 is a schematic diagram of an example yield estimation system.

FIG. 13 is a schematic diagram of a portion of the yield estimation system of FIG. 12.

FIG. 14 is a flow diagram of an example method for estimating biomass and/or grain yield.

FIG. 15 is a graph illustrating an example relationship between a sensed power characteristic and biomass yield or grain yield.

FIG. 27 is a schematic diagram of another example aggregate yield allocation system.

DETAILED DESCRIPTION OF EXAMPLES

Figure 7:
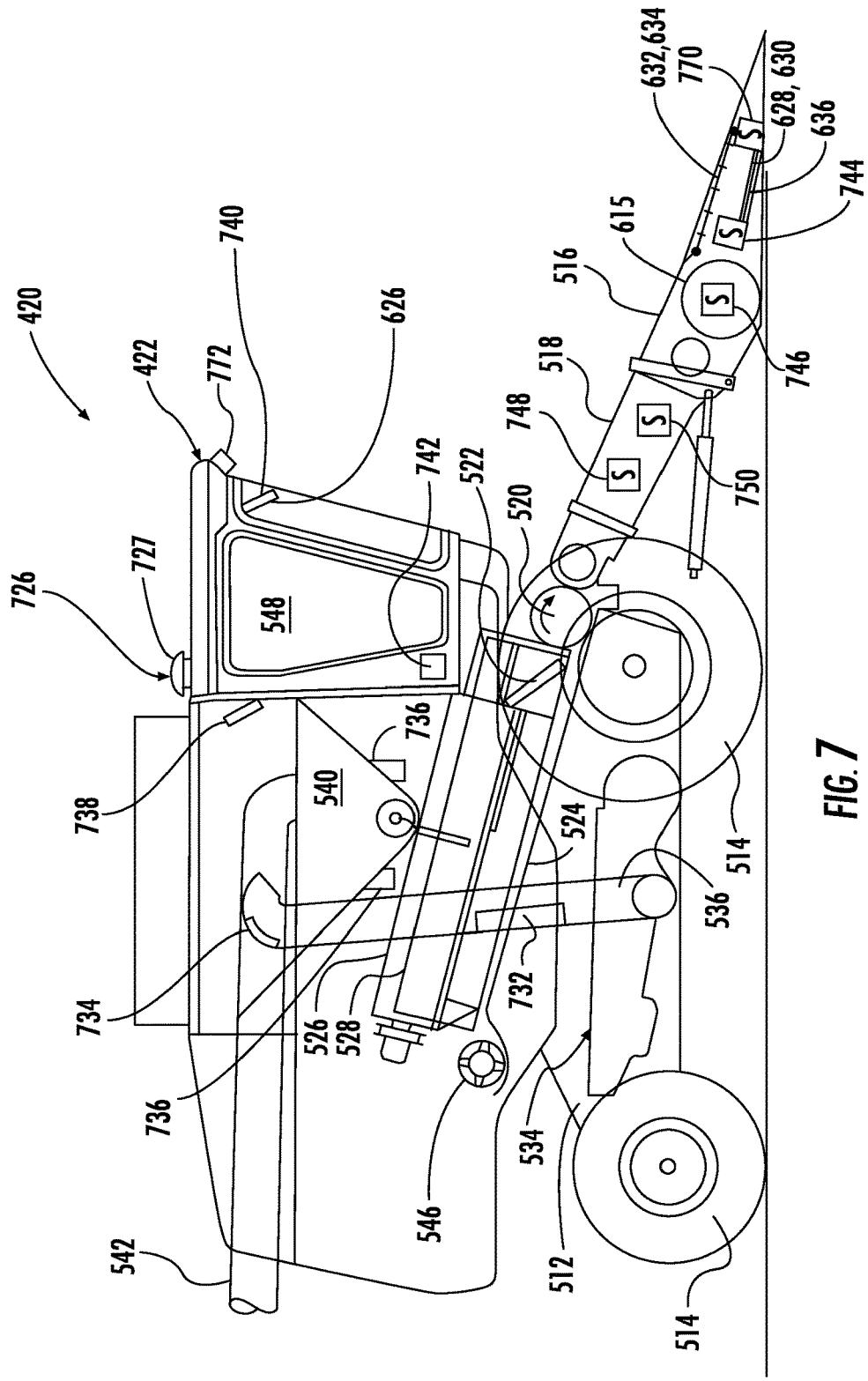
FIG. 7 is a schematic diagram of another example aggregate yield allocation system including an example harvester.

FIG. 1 schematically illustrates an example aggregate yield allocation system 20. Aggregate yield allocation system 20 allocates aggregate yield for a crop, such as grain or other harvested material such as cane billets, cotton and the like, to different geo-referenced locations or regions. As will be described hereafter, aggregate yield allocation system 20 takes into account different travel times for crops from different portions of a harvester head to an aggregate sensor when allocating the aggregate yield. As a result, system 20 more accurately allocates aggregate yield to the different geo-referenced locations or regions.

Aggregate yield allocation system 20 comprises harvester 22, machine controller 24, geo-referencing system 26, aggregate yield sensor 28, display 30, processor 32 and memory 34. Harvester 22 comprises a machine to harvest crops. In one implementation, harvester 22 is self-propelled. In another implementation, harvester 22 is towed. Harvester 22 removes portions of plants (the crop) from the growing medium or field. In one implementation, harvester 22 comprises a holding tank in which the crop is held. In another implementation, harvester 22 discharges the removed crop into a holding tank of another vehicle or onto the ground for subsequent collection.

Harvester 22 comprises crop removal portions 40A, 40B and 40C (collectively referred to as crop removal portions 40) and crop conveyors 42A, 42B, 42C (collectively referred to as crop conveyors 42), 44, each of which is schematically illustrated. Crop removal portions 40 sever, lift and/or remove the crop being harvested from the growing medium or field. In one implementation, crop removal portions 40 cut the stem or stalk of a plant carrying the crop to be harvested. In another implementation, crop removal portions 40 separate the crop to be harvested from the stalk or plant while the stalk or plant remains in the ground.

In the example illustrated, crop removal portions 40 are transversely located across a transverse width of harvester 22. In one implementation, crop removal portions 40 are located at different transverse locations across a harvester head. In other implementations, crop removal portions 40 are located at different transverse locations at different locations of harvester 22. Although harvester 22 is illustrated as comprising three crop removal portions 40, in other implementations, harvester 22 comprises two crop removal portions or more than three crop removal portions. For example, in one implementation, harvester 22 comprises a head having a plurality of row units, each row unit having a crop removal portion that removes the crop being harvested from the soil.

Crop conveyors 42 comprise mechanisms that convey the crops, once they have been removed or separated from the growing medium or field, to an aggregation location 48 at which crops from the different portions 40 are aggregated. In one implementation, aggregation location 48 comprises a feeder house at which crops harvested across the head are aggregated. In one implementation, due to the different transverse locations of crop removal portions 40, crop conveyors 42 have different lengths. In one implementation, crop conveyors 42 operate at different conveying speeds. Either due to the different transverse locations and/or the different conveying speeds, crops from crop removal portions 40 take different amounts of time to reach aggregation location 48.

In the example illustrated, crop conveyor 42A conveys crops from crop removal portion 40A to aggregation location 48 in time T1. Crop conveyor 42B conveys crops from crop removal portion 40B to aggregation location 48 in time T2 which is greater than time T1. Crop conveyor 42C conveys crops from crop removal portion 40C to aggregation location 48 in time T3 which is greater than time T2. In some implementations, one or more of crop conveyors 42 convey crops from different crop removal portions 40 in the same amount of time.

Crop conveyor 44 conveys crops from aggregation location 48 to an ultimate destination for the crop, whether it be a holding tank carried by harvester 22, a holding tank of another vehicle or a discharge location onto the ground for subsequent collection. In one implementation, crop conveyor 44 conveys the crop being harvested along with other material during separation of the crop from the other material. For example, in one implementation, crop conveyor 44 conveys portions of a plant and grain while the grain is separated from the remaining portions of the plant. In one implementation, crop conveyor 44 conveys the crop through one or more threshing devices.

Machine controller 24 comprise one or more processing units that output control signals to control the operational settings for harvester 22. For purposes of this application, the term "processing unit" shall mean a presently developed or future developed processing unit that executes sequences of instructions contained in a non-transitory computer-readable medium or memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, machine controller 24 is be embodied as part of one or more application-specific integrated circuits (ASICs). Unless otherwise specifically noted, the controller is not limited to any specific combination of hardware circuitry and software, nor to any particular source for the instructions executed by the processing unit.

In one implementation, machine controller 24 controls a translational speed of harvester 22 across a field, a severing or removal parameter for each of crop removal portions 40, a conveying speed or parameter for each of conveyors 42, 44, and/or an operational settings for threshing devices of harvester 22. In one implementation, machine controller 24 is carried by harvester 22 on board. In another implementation, machine controller 24 is at least partially embodied in a remote location, wherein such control signals are transmitted in a wireless fashion from the remote location to a communication transceiver carried by harvester 22.

Geo-reference system 26 comprises a device by which different regions of a field are identified, labeled and/or geo-referenced for being assigned crop yield characteristics. In one implementation, geo-reference system 26 specifically identifies a particular region or location of the field that is currently being driven over or traversed by harvester 22. In one implementation, geo-reference system 26 identifies regions of a field with a resolution such that each individual geo-referenced region has a width substantially equal to a width of harvester 22, such as a width of a head, such as when harvester 22 comprises a combine. In another implementation, the resolution is such that each geo-referenced region has a width of a plurality of rows less than the full width of harvester 22, wherein the full width of harvester 22 travels across multiple distinctly identified geo-referenced regions. In yet another implementation, the resolution is such that each geo-referenced region has a width equal to an individual row of plants, wherein each geo-referenced region has a width corresponding to an individual row of plants. In one implementation, the resolution of geo-referencing system 26 identifies geo-referenced regions having a length of a single rank of plants, a single plant across multiple rows. In another implementation, the resolution is such that each geo-referenced region has a length of a multiple ranks of plants, a set of multiple consecutive plants in each row. In one implementation, geo-reference system 26 comprises an antenna and associated electronics/software as part of a global navigational satellite system (GNSS) or global positioning system (GPS). In other implementations, other devices or other methods and/or technologies are used.

Aggregate yield sensor 28 comprises one or more sensors along conveyor 44 that output a signal indicating an aggregate yield of the crop that has been harvested during a measurement interval. In one implementation, an aggregate yield is the aggregation or total combined yield from each of portions 40 and as sensed by aggregate yield sensor 28. In one implementation, a measurement interval is a measurement interval during which the crop amount, resulting in the aggregate yield value, was sensed or detected by aggregate yield sensor 28. In one implementation, the measurement interval is defined as the lapse of a predetermined amount of time during which harvester 22 traverses a field. In another implementation, the measurement interval is defined as a distance traveled by harvester 22. During each measurement interval and/or at the end of each measurement interval, aggregate yield sensor 28 outputs signals which indicate a total or cumulative amount of crop that has been sensed during the measurement interval. In one implementation, each measurement interval is the same amount of time or the same amount of distance. In yet other implementations, measurement intervals vary in duration or distance.

In one implementation, aggregate yield sensor 28 comprises a grain flow sensor that detects a flow of crop, grain, by conveyor 44. For example, in one implementation, aggregate yield sensor 28 comprises a gamma ray attenuation sensor that measures flow rate of aggregated harvested grain by conveyor 44. In one implementation, aggregate yield sensor 28 comprises an impact plate sensor that detects impact of grain against a sensing plate or surface so as to measure mass flow rate of aggregated harvested grain by conveyor 44. In yet another implementation, aggregate yield sensor 28 comprises one or more load cells which measure or detect a load or aggregated massive harvested grain. For example, in one implementation, one or more load cells may be located at a bottom of a holding tank carried by harvester 22, wherein changes in the weight or mass of grain within the holding tank during the measurement interval indicates the aggregate yield during the measurement interval. In yet another implementation, aggregate yield sensor 28 comprises cameras or optical sensing devices that detect the size and/or shape of an aggregated mass of harvested grain, such as the shape of the mound or height of a mound of grain in a holding tank of harvester 22, wherein the change in shape or height of the mound during the measurement interval indicates the aggregate yield during the measurement interval. In other implementations, other aggregate yield sensing technologies are employed. In some implementations, aggregate yield sensor 28 comprises two or more of the above described sensors, wherein the aggregate yield for the measurement interval is determined from signals output by each of the multiple different types of sensors. For example, in one implementation, aggregate yield is determined based upon signals from a gamma ray attenuation sensor, an impact plate sensor, load cells within a holding tank and optical sensors along a holding tank of harvester 22.

Display 30 comprises a monitor, screen, panel or other device by which information is visibly communicated. In one implementation, display 30 additionally comprises auditory communication capabilities. Display 30 facilitates the presentation of information identifying the allocation of aggregate yield amongst different geo-referenced regions. In one implementation, display 30 is carried on board harvester 22 for viewing by an operator on harvester 22. In another implementation of display 30 is located remote with respect to harvester 22, such as where harvester 22 is remotely operated or such as when remote personnel or managers are analyzing or reviewing aggregate yield of different geo-referenced regions of a field.

Processor 32 comprises one or more processing units which receive signals from aggregate yield sensor 28 and signals from geo-referencing system 26 and utilizes such signals to allocate aggregate yield amongst different geo-referenced regions. In one implementation, processor to is embodied as part of machine controller 24. In another implementation processor 32 is separate and independent of machine controller 24.

Memory 34 comprises a non-transitory computer-readable medium or persistent storage device. In one implementation, memory 34 is carried by harvester 22. In another implementation, memory 34 is remote from harvester 22. In yet another implementation, memory 34 is distributed across different locations. Memory 34 comprises aggregate yield module 50, yield allocation module 52, machine control module 54, yield mapping module 56 and data storage 58.

Aggregate yield module 50 comprises software, code, circuitry and/or program logic providing instructions for directing processor 32 to determine an aggregate yield for each measurement interval based upon signals received from aggregate yield sensor 28. As noted above, the aggregate yield for each measurement interval is based upon signals received from a gamma ray attenuation sensor, impact plate sensors, flow sensors, load sensors and/or optical sensors.

Yield allocation module 52 comprises software, code, circuitry and/or program logic providing instructions for directing processor 32 to allocate portions of the aggregate yield for a particular measurement interval to each of at least two geo-referenced regions that were traversed by harvester 22 prior to the particular measurement interval, wherein the allocation is based upon different amounts of time for crops to travel to aggregate yield sensor 28 after being initially separated from the growing medium or ground to aggregate yield sensor 28. In the example illustrated, the time for crops to travel from aggregation location 48 to aggregate yield sensor 28 is the same for crops harvested from each of portions 40. However, due to either different travel distances and/or different conveying speeds, reflected by the different travel times T1, T2 and T3 for portions 40A, 40B and 40C, respectively, crops removed by crop removal portions 40A, 40B and 40C during a particular measurement interval arrive at aggregate yield sensor 28 at different times after conclusion of the measurement interval. Yield allocation module 52 allocates the aggregate yield value for the measurement interval to different geo-referenced regions that were traversed or interacted upon by crop removal portions 40 prior to the measurement interval.

FIG. 2 schematically illustrates an example aggregate yield allocation scheme 100 carried out by aggregate yield allocation system 20. FIG. 2 illustrates the initial removal of crop from the growing medium or field by each of crop removal portions 40 during each of measurement intervals 1, 2 and 3. The straight arrows in FIG. 2 indicate conveyance of the removed crop to aggregate yield sensor 28, wherein the end of such straight arrows indicate the measurement interval during which the removed crop arrives at aggregate yield sensor 28 and contributes to a determined aggregate yield for an associated measurement interval. The curved allocation arrows in FIG. 2 indicate allocation of aggregate yield from each particular measurement interval to geo-referenced regions which were traversed by harvester 22 during earlier measurement intervals.

As shown by FIG. 2, crop removal portion 40A removes crop from the growing medium at time 60 during measurement interval 1. After being removed, the crop removed at time 60A is conveyed, and possibly further interacted upon such as being threshed to separate from other portions of the plant, until the crop is sensed by aggregate yield sensor 28 at time 62A which occurs during a subsequent measurement interval 3. The difference between time 60A and 62A is the time consumed as a crop travels from portion 40A to aggregate yield sensor 28, times T1+T4, where time T1 is a duration of time for the crop to travel from crop removal portion 40A to aggregation location 48 and where time T4 is a duration of time for the crop to travel from aggregation location 48 to aggregate yield sensor 28.

Likewise, crop removal portion 40B removes crop from the growing medium at time 60B during measurement interval 1. After being removed, the crop removed at time 60B is conveyed, and possibly further interacted upon such as being threshed to separate from other portions of the plant, until the crop is sensed by aggregate yield sensor 28 at time 62B which occurs during a subsequent measurement interval 4. The difference between time 60B and 62B is the time consumed as a crop travels from portion 40B to aggregate yield sensor 28, times T2+T4, where time T2 is a duration of time for the crop to travel from crop removal portion 40B to aggregation location 48 and where time T4 is a duration of time for the crop to travel from aggregation location 48 to aggregate yield sensor 28. Because travel time T2 is greater than travel time T1, crops from portion 40B contribute to the aggregate yield of measurement interval 4 rather than measurement interval 3 despite that the crops for portions 40A and 40B were both separated from the growing medium during the same measurement interval 1.

Likewise, crop removal portion 40C removes crop from the growing medium at time 60C during measurement interval 1. After being removed, the crop removed at time 60C is conveyed, and possibly further interacted upon such as being threshed to separate grain from other portions of the plant, until the crop is sensed by aggregate yield sensor 28 at time 62C which occurs during a subsequent measurement interval 5. The difference between times 60C and 62C is the time consumed as a crop travels from portion 40C to aggregate yield sensor 28, times T3+T4, where time T3 is a duration of time for the crop to travel from crop removal portion 40C to aggregation location 48 and where time T4 is a duration of time for the crop to travel from aggregation location 48 to aggregate yield sensor 28. Because travel time T3 is greater than travel time T2, crops from portion 40C contribute to the aggregate yield of measurement interval 5 rather than measurement interval 4 despite that the crops for portions 40B and 40C were both separated from the growing medium during the same measurement interval 1.

As indicated by curved allocation arrows in FIG. 2, yield allocation module 52 allocates portions of the aggregate yield for each particular measurement interval back to two or more geo-referenced regions traversed by harvester 22 prior to the particular measurement interval. In the example illustrated, the aggregate yield for measurement interval 5, as determined by aggregate yield module 50, is allocated back to geo-referenced region 70 (as indicated by arrow 71A), which was traversed by harvester 22 during measurement interval 3; is allocated back to geo-referenced region 72 (as indicated by arrow 71B), which was traversed by harvester 22 during measurement interval 2; and is allocated back to geo-referenced region 74 (as indicated by arrow 71C), which was traversed by harvester during measurement interval 1.

Yield allocation module 52 is usable with various geo-referencing systems 26 having varying resolutions. For example, in one implementation, yield allocation module 52 is usable with a geo-referencing system 26, wherein each of geo-referenced regions 70, 72 and 74 has a width corresponding to a collective width of portions 40. In another implementation, aggregate yield allocation module 52 is usable with a geo-referencing system 26 having a resolution such that each of the geo-referenced regions has a width corresponding to the width of the particular portion 40 that harvested the crops from the associated geo-referenced region.

In one implementation, the aggregate yield for each measurement interval is equally divided and reallocated amongst the different geo-referenced regions. For example, in the scheme of FIG. 2, one third of the aggregate yield determined for measurement interval 5 is reallocated to each of geo-referenced regions 70, 72 and 74. As will be described hereafter, in other implementations, the aggregate yield from each measurement interval is differently allocated amongst two or more different geo-referenced regions. In one implementation, the allocation of the aggregate yield from a particular measurement interval to different geo-referenced regions is weighted. For example, in one implementation, the allocation of aggregate yield from a particular measurement interval is weighted based upon detected plant characteristics for each of the different geo-referenced regions. Such plant characteristics are detected during the harvest of the plants, such as when the plants are being interacted upon by harvester 22, and/or at times preceding the engagement of the plants by harvester 22. For example, in one implementation, plant characteristics are determined and recorded during cultivating, during fertilizer, herbicide or insecticide application or by overhead aerial photography/video for later aggregate yield allocation. In another implementation, the allocation of aggregate yield from a particular measurement interval is weighted based upon different sizes of different crop removal portions 40.

As further shown by FIG. 2, in the example illustrated, the aggregate yield for each measurement interval for each crop removal portion 40 is consistently allocated back to a geo-referenced region that was traversed during a prior measurement interval. For example, the aggregate yield for each measurement interval for crop removal portion 40A is consistently allocated back to a geo-referenced region that was traversed by harvester 22 during a measurement interval preceding the aggregate yield measurement interval by two measurement intervals. The aggregate yield for measurement interval 3 is allocated back to the geo-referenced region traversed by harvester 22 during measurement interval 1; the aggregate yield for measurement interval 4 is allocated back to the geo-referenced region traversed by harvester 22 during measurement interval 2; the aggregate yield for measurement interval 5 is allocated back to the geo-referenced region 70 traversed by harvester 22 during measurement interval 3; and so on. Likewise, the aggregate yield for each measurement interval for crop removal portion 40B is consistently allocated back to a geo-referenced region that was traversed by harvester 22 during a measurement interval preceding the aggregate yield measurement interval by three measurement intervals. The aggregate yield for each measurement interval for crop removal portion 40C is consistently allocated back to a geo-referenced region that was traversed by harvester 22 during a measurement interval preceding the aggregate yield measurement interval by four measurement intervals. This pattern of aggregate yield allocation is based on a presumption that the travel time for crops to travel from portions 40 to aggregate yield sensor 28 does not change. In such an implementation, such travel times associated with the different crop removal portions are determined by the manufacturer of harvester 22 through testing and data collection and/or are established and recorded during an initial calibration of harvester 22.

In another implementation, the allocation of aggregate yield from each measurement interval to a geo-referenced region that was traversed during an earlier measurement interval varies. For example, in one implementation, the travel times for each of portions 40 to aggregate yield sensor 28 are continuously or periodically sensed. In one implementation, harvester 22 comprises sensors 80A, 80B, 80C (shown in FIG. 1 and collectively referred to as sensors 80) that sense or detect the speed at which crops are conveyed or the time for crops to travel from each of the individual portions 40 to aggregation location 48. For example, in one implementation, times T1, T2 and T3 are determined by sensors 80 comprising cameras which capture a series of images, wherein the images are processed to measure travel times of different sections of harvester 22. For example, in one implementation, such sensors 80 determine times T1, T2 and/or T3 by capturing images of an ear of corn and tracking movement of the ear of corn in a series of time-stamped images.

In one implementation, harvester 22 additionally comprises sensors that sense or detect the speed at which crops travel from aggregation location 48 to aggregate yield sensor 28. For example, in one implementation, harvester 22 additionally comprises sensor 81 (schematically shown) which senses or detects the speed at which crop travels from aggregation location 48 to aggregate yield sensor 28. In such an implementation, yield allocation module 52 takes into account changes in performance over time of crop conveyors 42 due to wear and/or due to operational adjustments during the harvest of crops. For example, in one implementation, as harvester 22 is harvesting a crop, crop conveyors 42 and/or crop conveyor 44 undergo changes in the rate at which such crop conveyors convey the crop. In yet another implementation, the travel times are based upon control signals establishing the speed of the different crop conveyors 42, 44.

In one implementation, the conveyance speed of crop conveyors 42 and 44 uniformly change. In another implementation, the conveyance speed of crop conveyors 42 and 44 differently change, such as where the speed of crop conveyor 42C is increased to a greater extent as compared to crop conveyor 42B. Regardless of whether the conveying speeds of crop conveyors 42, 44 are uniformly or non-uniformly adjusted, yield allocation module 52 automatically adjusts the allocation of aggregate yield based upon signals from sensors 80.

In yet another implementation, harvester 22 additionally comprises roll sensor 86 and pitch sensor 88. Roll sensor 86 senses and detects the roll of harvester 22 as it is traversing a growing medium or field. Pitch sensor 88 senses and detects a current pitch of harvester 22 as it is traversing a growing medium or field. The detected roll and pitch of harvester 22 is recorded in memory 54 and associated with the particular geo-referenced region that was traversed by harvester 22 when harvester 22 experienced the detected roll and pitch. The roll and/or pitch of harvester 22 impacts the speed at which crops from different portions 40 are conveyed to aggregate yield sensor 28. In such an implementation, yield allocation module 52 automatically adjusts the allocation of the aggregate yield to geo-referenced regions previously traversed by harvester 22 during previous measurement intervals based upon signals from roll sensor 86 and/or pitch sensor 88.

For example, in one implementation, if harvester 22 has a forward pitch, leaning forward, such as when harvester 22 is traveling down an incline, conveyance of crops to a rearwardly located aggregate yield sensor 28 is prolonged, wherein yield allocation module 52 takes into account the longer time required for the crop to travel to aggregate yield sensor 28 by allocating the aggregate yield from a later measurement interval farther back in time to a geo-referenced region traversed during an even earlier measurement interval. If harvester 22 has a rearward pitch, leaning rearward, such as when harvester 22 is traveling up an incline, conveyance of crops to a rearwardly located aggregate yield sensor 28 is shortened, wherein yield allocation module 52 takes into account the shorter time required for the crop to travel to aggregate yield sensor 28 by allocating the aggregate yield to a geo-referenced region traversed during a more recent measurement interval.

In one implementation, if signals from roll sensor 86 indicate that harvester 22 has a roll to the right side of harvester 22, such as when harvester 22 is traveling across a side of a hill and leaning towards the right side of harvester 22, conveyance of crops from crop removing portions 40 on the right side of harvester 22 may have a longer travel time while conveyance of crops from crop removing portions 40 on the left side of harvester 22 may have a shorter travel time due to gravity. In such a circumstance, yield allocation module 52 automatically adjusts to the sideways tilt of harvester 22 by allocating the aggregate yield from a later measurement interval to different geo-referenced regions depending upon whether the geo-referenced region was harvested by a left side of harvester 22 or by a right side of harvester 22. Likewise, if signals from roll sensor 86 indicate that harvester 22 has a roll to the left side of harvester 22, such as when harvester 22 is traveling across a side of a hill and leaning towards the left side of harvester 22, conveyance of crops from crop removing portions 40 on the left side of harvester 22 may have a longer travel time while conveyance of crops from crop removing portions 40 on the right side of harvester 22 may have a shorter travel time due to gravity. In such a circumstance, yield allocation module 52 automatically adjusts to the sideways tilt of harvester 22 by allocating the aggregate yield from a later measurement interval to different geo-referenced regions depending upon whether the geo-referenced region was harvested by a left side of harvester 22 or by a right side of harvester 22.

Machine control module 54 comprises software, code, circuitry and/or program logic providing instructions for directing processor 32 to adjust operational settings or parameters of machine control 24 of harvester 22 based upon the allocation of aggregate yield to different geo-referenced regions. For example, in one implementation, machine control module 54 automatically adjusts operational speeds or conveying speeds of crop conveyors 42 based upon allocations of the aggregate yield to the different geo-referenced regions. In another implementation, machine control module 54 automatically adjusts operational settings for crop removal portions 40 based upon allocations of aggregate yield to the different geo-referenced regions. In yet another implementation, the control module 54 automatically adjusts operational settings of a threshing component, such as concave spacings in a combine, based upon allocations of aggregate yield to different geo-referenced regions.

Yield mapping module 56 comprises software, code, circuitry and/or program logic providing instructions for directing processor 32 to map the allocation of aggregate yield to the different geo-referenced regions traversed by harvester 22. In one implementation, yield mapping module 56 records or stores the maps of yield for the different geo-referenced regions in data storage 58. Data storage 58 comprises a data storage portion of memory 34. In one implementation, in addition to storing yield maps for the different geo-referenced regions, data storage 58 also stores additional data such as the aggregate yield for the different measurement intervals as well as earlier detected plant characteristics that are detected during the harvest of such plants or that are detected at earlier times prior to engagement of the plants by harvester 22, such as during herbicide, insecticide or fertilizer application, cultivation or overhead or aerial crop data collection. As noted above, in different implementations, data storage 58 is carried by harvester 22, at a location remote from harvester 22 and/or is distributed across different sites.

FIG. 1 illustrates a portion of an example yield map 120 recorded in data storage 58 by yield mapping module 56 in accordance with the example allocation scheme 100 shown in FIG. 2. The example yield map 120 is illustrated as having three yield map regions 122, 124 and 126. In the example illustrated, each yield map region 122, 124, 126 has a resolution having a width equal to the combined or collective width of portions 40 and a length equal to the distance traveled by harvester 22 during the associated measurement interval. Yield map region 122 comprises those geo-referenced regions harvested by crop removal portions 40 and traversed by harvester 22 during measurement interval 1. In the example illustrated, the yield for region 122 comprises the portion of the aggregate yield from measurement interval 3, from measurement interval 4 and from measurement interval 5. Likewise, Yield map region 124 comprises those geo-referenced regions harvested by crop removal portions 40 and traversed by harvester 22 during measurement interval 2. In the example illustrated, the yield for region 122 comprises the portion of the aggregate yield from measurement interval 4, from measurement interval 5 and from measurement interval 6. Yield map region 122 comprises those geo-referenced regions harvested by crop removal portions 40 and traversed by harvester 22 during measurement interval 3. In the example illustrated, the yield for region 122 comprises the portion of the aggregate yield from measurement interval 4, from measurement interval 5 and from measurement interval 6.

FIG. 3 is a flow diagram of an example method 200 for allocating aggregate yield to geo-referenced regions. As indicated by block 210, processor 32 receives an aggregate yield value during a measurement interval. In the example implementation of FIG. 1, processor 32 determines the aggregate yield in accordance with instructions provided by aggregate yield module 50 and signals received from aggregate yield sensor 28. As indicated by block 212, processor 32 identifies geo-referenced regions crossed by harvester 22 during the measurement interval. Such geo-referenced regions are identified based upon signals from geo-referencing system 26. As indicated by block 216, yield allocation module 52 allocate aggregate yield portions to regions based upon the travel times of the crop from different portions of harvester 22, such as crop removal portions 40. As indicated by block 218, system 20 outputs aggregate yield allocations. In the example implementation of FIG. 1, such output is utilized by machine control module 54 to adjust the operational parameter settings of machine control 24 and/or by yield mapping module 56 to present and display yield maps, such as yield map 120, on display 30 and/or store such maps in data storage 58.

FIG. 4 is a flow diagram illustrating an example method 300 for allocating aggregate crop yield. Method 300 is similar to method 200 except that method 300 applies different allocation weightings to different regions. As indicated by block 310, processor 32 receives an aggregate yield value during a measurement interval. In the example implementation of FIG. 1, processor 32 determines the aggregate yield in accordance with instructions provided by aggregate yield module 50 and signals received from aggregate yield sensor 28. As indicated by block 312, processor 32 identifies geo-referenced regions crossed by harvester 22 during the measurement interval. Such geo-referenced regions are identified based upon signals from geo-referencing system 26.

As indicated by block 314, processor 32 receives weightings for the different geo-referenced regions that have been crossed prior to the measurement interval. In one implementation, such weightings are based upon characteristics of the plants from each of portions 40 as detected during harvesting of the plants by harvester 22. For example, in one implementation, harvester 22 includes sensors that detect a thickness of each of the stalks of the plants being harvested by each of the regions 40, wherein allocation of aggregate yield to each of the regions 40 is weighted based upon the detected thickness of the plants by any of the regions 40. For example, two geo-referenced regions traversed by harvester 22 during the same measurement interval may receive different aggregate yield allocations due the stalks and one of the geo-referenced regions being thicker or wider than the stalks of the other of the geo-referenced regions, where the greater thickness of the stalk is determined as being linked to greater crop yield.

In another implementation, the two geo-referenced regions traversed by harvester 22 during the same measurement interval may receive different aggregate yield allocations from a later measurement interval due to other indications reflecting greater yield. For example, in one implementation, harvester 22 senses an impact of the crop, such as ears of corn, with harvester 22, such as against a stripper plate of harvester 22, wherein the two geo-referenced regions traversed by harvester 22 during the same measurement interval may receive different aggregate yield allocations from a later measurement interval due to sensed crop impacts being larger from plants in one geo-referenced region versus another geo-referenced region.

In another implementation, at least one sensor senses a power characteristic of each of different components across a crop harvesting width of the harvester 22, wherein yield allocation weightings for different plants in different geo-referenced regions are based upon the actual sensed power characteristics and/or differences in the sensed power characteristics of the different components across the harvesting width. For example, harvester 22 may be harvesting a first geo-referenced region and a second geo-referenced region at the same time across its harvesting width. Due to the first geo-referenced region providing a greater crop yield than the second geo-referenced region, the power consumed or otherwise employed to harvest the crops in the first geo-referenced region in many instances will be greater than the power consumed or otherwise employed to harvest the crops in the second geo-referenced region. As a result, the power consumed or employed by components of harvester 22 to harvest the crops in the first geo-referenced region will likely be greater than the power consumed or employed by components of harvester 22 to harvest the crops in the second geo-referenced region. Harvester 22 utilizes power sensors to sense a power characteristic associated with each of different components across the harvesting head and applies different yield allocation weightings to different geo-referenced regions based upon the actual sensed power characteristics and/or a relationship between the sensed power characteristics of the different components.

Examples of components across the harvesting width of harvester 22 for which power characteristics are be sensed include, but are not limited to, a snap roller, a stalk chopper, and a cutter bar. Examples of sensors used to detect or sense the power characteristics that harvester 22 uses to weight yield allocation amongst different geo-referenced/time stamped regions include, but are not limited to, a voltage sensor, a current sensor, a torque sensor, a hydraulic pressure sensor, a hydraulic flow sensor, a force sensor, a bearing load sensor and a rotational sensor. In some implementations, harvester 22 weights yield allocation amongst different geo-referenced regions, including timestamp regions, based upon sensed power characteristics of more than one type of crop interacting component across a harvesting width of harvester 22. In such implementations, using sensed power characteristics from more than one crop interacting component in each transverse portion of the harvesting width results in greater weighting assignment accuracy amongst the different geo-referenced/timestamp regions harvested by the different transfers portions of the harvesting width.

In yet another implementation, such yield allocation weightings are based upon captured video or images of the plants during harvest. For example, in one implementation, cameras carried by harvester 22 capture images of the plants prior to engaging with harvester 22, wherein such images are analyzed. The results of such analysis are used to generate and apply yield allocation weightings. For example, in one implementation, light detection and ranging (LIDAR) is used as a basis for estimating yield, wherein the yield estimates are used to generate yield allocation weightings for allocating the sensed aggregate yield to different georeferenced regions. In yet other implementations, such weightings are determined based upon other sensed characteristics of plants being harvested by harvester 22.

In yet other implementations, yield allocation weightings are based upon historical plant data acquired for the different geo-referenced regions prior to harvesting. Such historical plant data is acquired during field operations at any time from planting up to harvesting. For example, during field operations such as cultivation or the application of herbicide, insecticide and/or fertilizer, one or more plant characteristics are detected or sensed and stored. Different yield allocation weightings are determined based upon such historical data. Certain plant characteristics taken at various times are linked to greater yield. For example, taller plants, thicker plants, greener plants may all be linked to greater yield. In such an implementation, if a first geo-referenced region traversed by harvester 22 during a measurement interval is associated with historical data indicating that the region contained taller plants, thicker plants and/or greener plants during cultivation and/or during the application of herbicide, insecticide, fertilizer, as compared to a second geo-referenced region traversed by harvester 22 during the same measurement interval, yield allocation module 52 applies a larger region yield allocation weighting to the first geo-referenced region as compared to the second geo-referenced region. In one implementation, such historical data may additionally or alternatively be acquired through overhead or aerial surveillance of plants within a field prior to harvesting.

As indicated by block 316, yield allocation module 52 allocates aggregate yield portions to regions based upon the travel times of the crop from different portions of harvester 22, such as crop removal portions 40, and the region weightings. FIG. 5 schematically illustrates an example aggregate yield allocation scheme 300 carried out by aggregate yield allocation system 20. As with scheme 100 shown in FIG. 2, scheme 300 and FIG. 5 illustrates the initial removal of crop from the growing medium or field by each of crop removal portions 40 during each of measurement intervals 1, 2 and 3. The straight arrows in FIG. 3 indicate conveyance of the removed crop to aggregate yield a sensor 28, wherein the end of such straight arrows indicate the measurement interval during which the removed crop arrives at aggregate yield sensor 28 and contributes to a determined aggregate yield for an associated measurement interval. The curved allocation arrows in FIG. 5 indicate allocation of aggregate yield from each particular measurement interval to geo-referenced regions which were traversed by harvester 22 during earlier measurement intervals.

Aggregate yield allocation scheme 300 is similar to scheme 100 except that allocation scheme 300 additionally illustrates the application of different region weightings W. As described above with respect to block 314 in FIG. 4, in one implementation, such weightings W are based upon characteristics of the plants from each of portions 40 as detected during harvesting of the plants by harvester 22 and/or are based upon historically acquired characteristics or data regarding the plants from each of the portions 40. In the example illustrated, the portion of the aggregate yield of measurement interval 3 allocated back to geo-referenced region 302 is weighted by region weighting W11 which is based upon characteristics of plants grown in region 302A. The portion of the aggregate yield of measurement interval 4 allocated back to geo-referenced region 302B is weighted by region weighting W21 which is based upon characteristics of the plants grown in region 302B. The portion of the aggregate yield of measurement interval 5 allocated back to geo-referenced region 302C is weighted by region weighting W31 which is based upon characteristics of the plants grown in region 302C. As further shown by FIG. 5, relationships between regional weightings impacts the allocation of the aggregate yield by yield allocation module 52. For example, the aggregate yield sensed during measurement interval 5 is allocated amongst regions 306A, 304B and 302C. Region weightings impact proportional allocation of the aggregate yield to the prior geo-referenced regions. In the example scheme illustrating 5, yield allocation module 52 apportions the aggregate yield of measurement interval 5 amongst regions 306A, 304B and 302C based upon the relationship between the associated region weightings W13, W22 and W31. For example, if region weighting W22 is greater than region weightings W13 or W31, yield allocation module 52 allocates a greater percentage a portion of the aggregate yield of measurement interval 5 to region 304B. In one implementation, the aggregate yield is allocated to the different regions based upon or in proportion to the relation between the region weightings.

As indicated by block 318, system 20 outputs aggregate yield allocations. In the example implementation of FIG. 1, such output is utilized by machine control module 54 to adjust the operational parameter settings of machine control 24 and/or is utilized by yield mapping module 56 to present and display yield maps on display 30 and/or store such maps in data storage 58. FIG. 6 illustrates an example yield map 320 resulting from the example yield allocation scheme 300 shown in FIG. 5. As shown by FIG. 6, yield map 320 comprises yield map regions 322, 324 and 326, with each of yield map regions 322, 324, 326 comprising a geo-referenced region from which crops are harvested by crop removal portions 40. Yield map region 322 comprises geo-referenced regions 352A, 352B and 352C (collectively referred to as geo-referenced regions 352) harvested during measurement interval 1 in FIG. 5 by crop removal portions 40A, 40B and 40C, respectively. Similarly, yield map region 324 comprises geo-referenced regions 354A, 354B and 354C (collectively referred to as geo-referenced regions 354) harvested during measurement interval 2 in FIG. 5 by crop removal portions 40A, 40B and 40C, respectively. Yield map region 322 comprises geo-referenced regions 356A, 356B and 356C (collectively referred to as geo-referenced regions 356) harvested during measurement interval 3 in FIG. 5 by crop removal portions 40A, 40B and 40C, respectively. As shown by FIG. 6, each of geo-referenced regions 352, 354 and 356 has a yield value based upon the aggregate yield sensed by aggregate yield system 28 during a later measurement interval and as weighted by the aggregate yield region weighting W for the particular region. Yield map 320 has a resolution having a width of each individual crop removal portion 40 and a length corresponding to the distance that harvester 22 traverses during the particular measurement interval.

Figure 8:
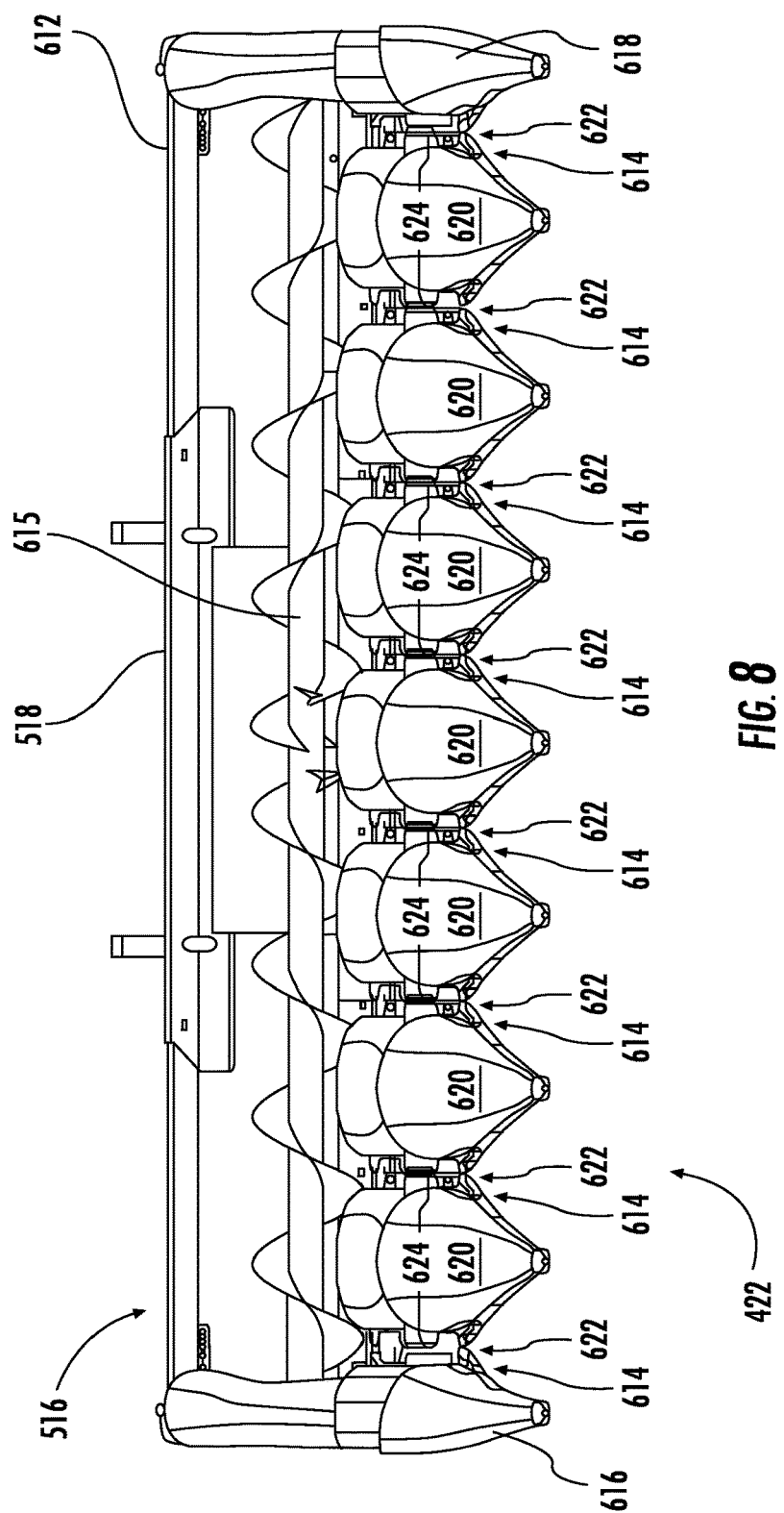
FIG. 8 is a front view of an example head of the harvester of FIG. 7.

FIGS. 7 and 8 illustrate aggregate yield allocation system 420, an example implementation of aggregate yield allocation system 20. Aggregate yield allocation system 420 is similar to aggregate yield system 20 except that aggregate yield allocation system 420 is illustrated as being specifically used with harvester 422 (in the form of a combine). Aggregate yield allocation system 420 comprises each of the components illustrated and described with respect to FIG. 1, some of which are shown and similarly numbered in FIG. 7, except that aggregate yield allocation system 420 specifically includes aggregate yield sensors 732, 734, 736, 738, travel time or conveying speed sensors 740, 744, and sensors 748, 750, particular examples of sensors 28, 80, 86 and 88 respectively.

Harvester 422 comprises a chassis 512 which is supported and propelled by ground engaging wheels 514. Although harvester 422 is illustrated as being supported and propelled on ground engaging wheels 514, in other implementations, harvester 422 is supported and propelled by full tracks or half-tracks. A harvesting platform or head 516 (shown as a corn head) is used to take up crop and to convey it to a feeder house 518, which serves as an aggregation location for crops from different portions of head 516.

As schematically shown in FIG. 7 and shown in more detail in FIG. 8, harvesting head 516 comprises frame 612, row units 614, auger 615. Frame 612 extends across the physical width of harvesting head 516 and supports row units 614. Row units 614 harvest corn from individual rows of crop and convey the harvested corn to auger 615 for further conveyance to feeder house 518. Row units 614 are spaced in a side-by-side relationship with each other a distance commensurate with the spacing between adjacent rows of corn to be harvested. As shown by FIG. 8, outer dividers 616, 618 and central dividers 1620 direct plants, such as cornstalks, into engagement with each of row units 614. Central dividers 620 extend between consecutive row units 614. Dividers 616, 618 and 620 cooperate to define longitudinal passages 622 which are centered relative to the rows to be harvested and a fore-and-aft extending relatively narrow throat 624 defined by each row unit 614. In some implementations, the row units 614 may be adjustable to accommodate other row spacings.

Figure 9:
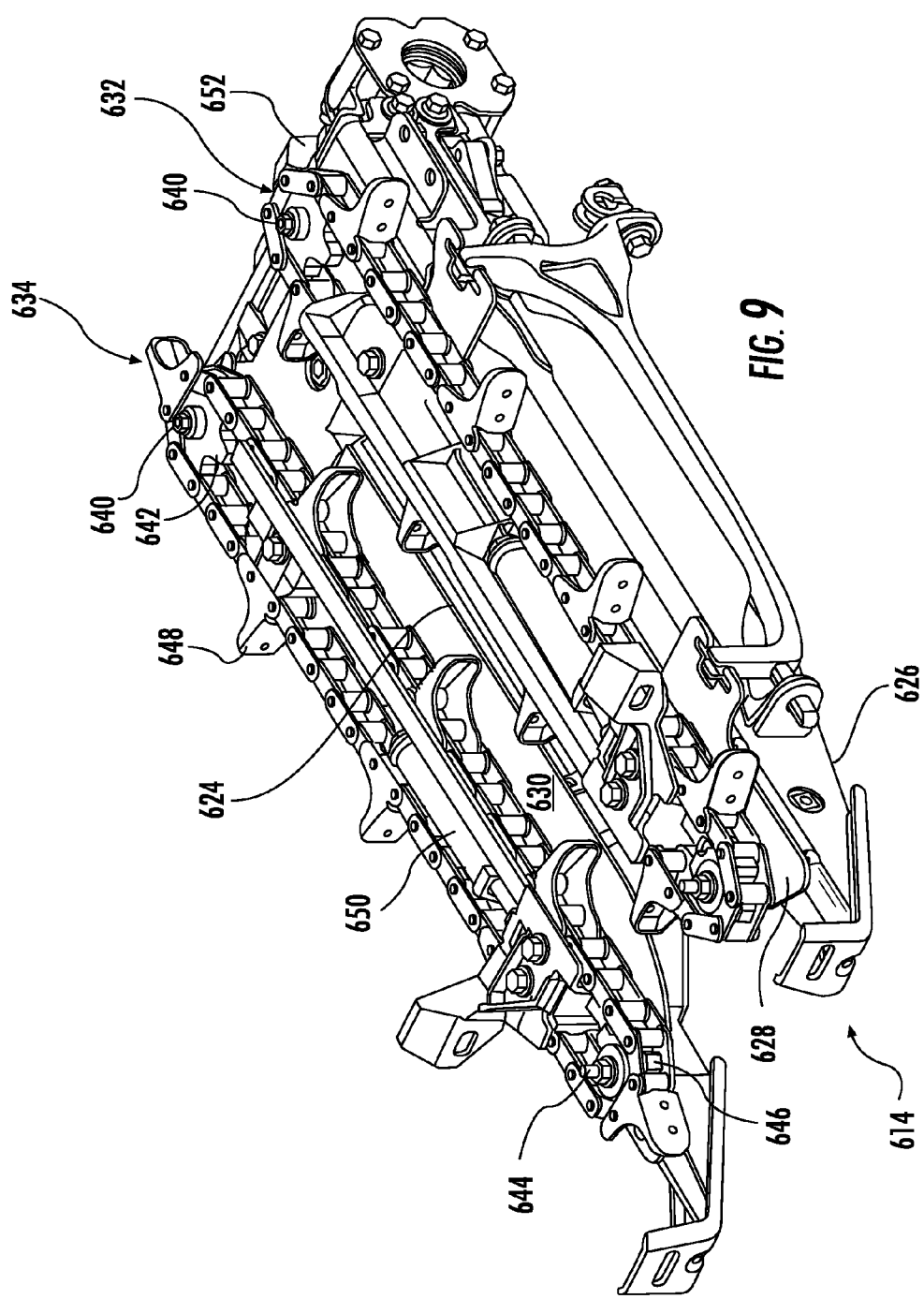
FIG. 9 is a perspective view of an example row unit of the head of FIG. 8.

FIG. 9 illustrates one example row unit 614. Each row unit 614 comprises frame 626, right and left stripper plates, also known as deck plates, 628, 630, right and left gathering units 632, 634 and snapping rolls 636, schematically shown in FIG. 7 below stripper plates 628, 630. Frame 626 supports stripper plates 628, right and left gathering units 632, 634 and snapping rolls 636.

Stripper plates 628, 630 comprise plates having inner edges spaced apart so as to define narrow throat 624. Throat 624 receives cornstalks of an aligned row as row unit 1214 moves along a row of crops. As row unit 614 is moved along the row, the stalks are drawn down through throat 624 with the assistance of the snapping rolls 636 such that ears of corn carried by the stalk impact the stripper plates and are separated from the stalk. Left and right gathering units 632, 634 convey the separated ears of corn in a longitudinal direction rearwardly to auger 615. Auger 615 further conveys the separated ears of corn in transverse directions to feeder house 518. Due to the different transverse locations of the different row units 614 (as shown in FIG. 8), the ears of corn from the different row unit 614 arrive at feeder house 518 at different times. In other words, the ears of corn from the outer row units or outer portions of head 516 are conveyed, on average, for longer periods of time by auger 615 as compared to the ears of corn from the more central portions or inner row units, transversely closer to feeder house 518.

As shown by FIG. 7, the crop is conveyed by the feeder house 518 to a beater 520. The beater 520 guides the crop upwardly through an intake transition region 522 to a rotary threshing and separating assembly 524. Although harvester 422 is described as a rotary combine, in other implementations, harvester 422 may comprise other types of combines (for example combines having a transverse threshing cylinder and straw walkers or combines having a transverse threshing cylinder and rotary separator rotors) or other agricultural harvesting machines including, without limitation, self-propelled forage harvesters, sugar cane harvesters, and windrowers The rotary threshing and separating assembly 524 comprises a rotor housing 526 and a rotor 528 arranged in the rotor housing 526. The harvested crop enters the rotor housing 526 through the intake transition region 522. The rotary threshing and separating assembly 524 threshes and separates the harvested crop. Grain and chaff fall through grates at the bottom of the rotor housing onto a cleaning assembly 534. The cleaning assembly 534 removes the chaff and conducts the clean grain to a grain elevator 536 which conducts upwardly to grain tank 540. The clean grain in the grain tank 540 can be unloaded through an unloading auger 542 into a trailer or truck. Threshed straw separated from the grain is conducted out of the rotary threshing and separating assembly 524 through an outlet to a discharge beater 546. The discharge beater 546 ejects the straw out the rear of harvester 422.

As schematically shown by FIG. 7, in addition to the above described elements of harvester 422, aggregate yield allocation system 420 further comprises geo-referencing system 726, aggregate yield sensors 732, 734, 736, 738, display 740, crop conveyor sensors 744, 746, pitch sensor 748, roll sensor 750 and yield allocator and control unit 742. Geo-referencing system 726 comprises a device, including localization input 727, by which different regions of a field are identified, labeled and/or geo-referenced for being assigned crop yield characteristics. In one implementation, geo-reference system 726 specifically identifies a particular region or location of the field that is currently being driven over or traversed by harvester 422. In one implementation, geo-reference system 726 identifies regions of a field with a resolution such that each individual geo-referenced region has a width substantially equal to a width of head 516. In another implementation, the resolution is such that each geo-referenced region has a width of a plurality of row units less than the full width of harvester 422, wherein the full width of harvester 422 travels across multiple distinctly identified geo-referenced regions. In yet another implementation, the resolution is such that each geo-referenced region has a width equal to an individual row of plants, wherein each geo-referenced region has a width corresponding to an individual row of plants or an individual row unit 614. In one implementation, the resolution of geo-referencing system 26 identifies geo-referenced regions having a length of a single rank of plants, a single plant position across multiple rows. In another implementation, the resolution is such that each geo-referenced region has a length of a multiple ranks of plants, a set of multiple consecutive plant positions in each row. In one implementation, geo-reference system 726 comprises an antenna and associated electronics/software as part of a global navigational satellite system (GNSS) or global positioning system (GPS). In other implementations, other devices or other methods and/or technologies are used.

As schematically shown in FIG. 7, harvester 422 comprises multiple aggregate yield sensors: grain flow sensor 732, impact plate sensor 734, load sensors 736 and optical sensors 738. Grain flow sensor 732 comprises a sensor, such as a gamma ray attenuation sensor, positioned along clean grain elevator 536, which senses or measures the flow rate of aggregated harvested grain. In other implementations, grain flow sensor 732 is provided at other locations.

Impact plate sensor 734 detects the volume or mass of grain based upon impact of the grain with an impact plate. In one implementation, impact plate sensor 734 comprises an impact plate mounted so that it deflects in a direction generally parallel to the direction of grain flow. Its deflection is dependent upon the mass flow rate of the clean grain. The deflection of the impact plate is measured and thus data on the mass flow rate of the harvested grain is provided. Such a sensor is described in U.S. Pat. No. 5,343,761 (the full disclosure of which is hereby incorporate by reference) and the documents recited therein.

Load sensors 736 comprise one or more load cells underlying portions of grain tank 540. In one implementation, load sensors 736 sense or detect the total weight or mass of tank 540 and the grain held by tank 540, wherein changes in the mass indicate aggregate yield. In another implementation, load sensors 736 comprise load cells that sense or measure grain pressure against walls are surfaces of tank 540, wherein changes in the pressure indicate aggregate yield. Optical sensors 738 comprise one or more cameras, optical emitter-detector pairs, such as infrared emitter-detector pairs, which detect the amount of grain within holding tank 540. In one implementation, such optical sensors 738 detect a level of grain within tank 540, wherein changes in the level of grain indicate aggregate yield. In yet another implementation, such optical sensors 738 additionally or alternatively detect a shape of the mound of grain within grain tank 540, wherein changes in the shape indicate aggregate yield. In one implementation, optical sensors 738 cooperate with load sensors 736 to indicate aggregate yield. One example of such an implementation is disclosed in U.S. patent application Ser. No. 14/318,165 filed on Jun. 27, 2014 by Johnson et al. and entitled GRAIN MASS FLOW ESTIMATION, the full disclosure of which is hereby incorporated by reference.

In the example illustrated, signals from each of the aggregate yield sensors 732, 734, 736, 738 are used to determine an aggregate yield for different measured intervals as harvester 422 traverses a field during harvest. In one implementation, the different results from the different aggregate yield sensors are specifically averaged or otherwise combined. In another implementation, signals from one of aggregate yield sensors 732, 734, 736, 738 serves as a base measurement, wherein adjustments are made to the base measurement based upon signals from the other aggregate yield sensors. In still other implementations, one or more of such aggregate yield sensors 732, 734, 736, 738 are omitted.

Display 740 comprises a monitor, screen, panel or other device by which information is visibly communicated. In one implementation of display 740 additionally comprises auditory communication capabilities. Display 740 facilitates the presentation of information identifying the allocation of aggregate yield amongst different geo-referenced regions. In the example illustrated, display 740 is carried on board harvester 422 for viewing by an operator within cab 948 of harvester 422. In another implementation, display 740 is located remote with respect to harvester 422, such as where harvester 422 is remotely operated or such as when remote personnel or managers are analyzing or reviewing aggregate yield of different geo-referenced regions of a field.

Crop conveyor sensors 744, 746 detect the travel time of crops along head 516 by affecting the conveyance speed of different portions of head 516. Conveyor sensors 744 output signals indicating the speed at which gathering units 632, 634 convey the crop, such as ears of corn or other crops, rearwardly along each of row units 614 to auger 615. In one implementation, each row unit 614 is equipped with an assigned sensor 744 such that different conveyance speeds of different gathering unit 632, 634 along different row unit 614 are detected. Conveyor sensor 746 comprises one or more sensors that output signals indicating the time for the crop, ears of corn, to be transversely conveyed to feeder house 518 and/or the conveyance speed of auger 615. In the example illustrated, the time for the crop to be conveyed from feeder house 518 to aggregate sensors 732, 734, 736, 738 is determined based upon the time at which the crop being conveyed is found to reach feeder house 516, based upon signals from sensor 744 and 746 and the rate at which the crop is conveyed from feeder house 518 to the aggregate yield sensors by the various components of harvester 422 between feeder house 518 and the aggregate yield sensors.

Pitch sensor 748 comprises one or more sensors that output signals indicating a pitch of harvester 422. In one implementation, pitch sensor 748 outputs signals indicating a pitch of head 516, independent of what might be the pitch of a remainder of harvester 422. Roll sensor 750 comprises one or more sensors that output signals indicating a roll of harvester 422. In one implementation, roll sensor 750 outputs signals indicating a roll of head 516, independent of what might be a different roll for the remainder of harvester 422. In some implementations, one or more of sensors 744, 746, 748 and 750 are omitted, wherein predetermined default values are utilized for the conveyor speeds, pitch and/or roll.

Yield allocator and control unit 742 comprises a computing component incorporating processor 32 and memory 34 described above. Yield allocator and control unit further comprises machine controller 24 described above. Although illustrated as being carried by harvester 422, in other implementations, yield allocator and control unit 742 is located remote from harvester 422 or is distributed with portions carried by harvester 422 and with other portions remote from harvester 422, wherein communication is facilitated in a wireless fashion using radio frequencies or other wireless technologies.

In operation, processor 32 of unit 742 receives an aggregate yield value during a measurement interval. In the example implementation, processor 32 determines the aggregate yield in accordance with instructions provided by aggregate yield module 50 and signals are received from one or more of aggregate yield sensors 732, 734, 736, 738. Processor 32 of unit 742 receives signals from localization input 727 indicating geo-referenced regions crossed by harvester 422 during the measurement interval. Based upon signals from sensors 744 and 746, yield allocation module 52 of unit 742 determines differences in times for crops collected by different portions, different individual row units or groups of row units 614 of head 516 to travel to aggregate yield sensors 732, 734, 736, 738. In one implementation, yield allocation module 52 of unit 742 determines differences in time for crops collected by different portions of head 516 to travel to feeder housing 518 and adjusts a base or predetermined travel time from head 615 to tank 540 based upon the differences.

FIG. 10 schematically illustrates an example area 749 of a field being harvested by harvester 422 which is eight rows by 36 ranks in area. FIG. 10 illustrates one example set of different travel times for crops traveling from different portions of head 516 to a location where the crops are sensed for the purpose of determining aggregate yield. The time at which harvested material, such as an ear of corn, being harvested arrives at feeder house 518 for each plant is shown in each cell. In the example illustrated, travel time is one second up each row unit 614 and two seconds per row away from the center rows 3 and 4. Delay from the feeder house to the particular aggregate yield sensor being utilized, aggregate yield sensor 734, is 10 seconds. In the example shown in FIG. 10, the measured aggregate yield from the measurement interval 17.0 to 18.0 seconds is from crops, ears, entering feeder house 518 at the interval 7.0 to 8.0 seconds. These crops, such as ears, are identified in FIG. 10 by shaded subregions 1400. In particular, as indicated by such shading, crop ranks 1-6, 11-16, 21-26 and 31-36 (indicated in the leftmost column) all arrive at the aggregate yield sensor 734 during the same measurement interval, during the time interval of 17.0 to 18.0 seconds.

FIG. 11 is a diagram illustrating the different times at which crops harvested by the different row unit 614 during a same measurement interval contribute to the detected aggregate yield for multiple subsequent measurement intervals. FIG. 11 illustrates the harvesting of crops by harvester 422 having eight row units 614 during 40 measurement intervals, wherein each measurement interval is one second. The time at which crops or plants from a particular row unit 614 arrive at feeder house 518 is shown in each cell. As shown by FIG. 11, crops harvested by Row 1 at time 17 (indicated in the left most time column) arrive at feeder house 518 at time 23 (indicated in the cell corresponding to time 17 and Row 1). Crops harvested by Row 2 during the same time 17 arrive at the feeder house at time 21, crops harvested by Row 3 during the same time 17 arrive at feeder house 518 at time 19 and so on, reflecting the travel time of two seconds per row away from center Rows 3 and 4. Crops harvested by Row 1 at time 18 arrive at feeder house 518 at time 24, reflecting the one second measurement interval.

In the example illustrated, delay from the feeder house to the particular aggregate yield sensor being utilized, aggregate yield sensor 734 is 10 seconds. The cells of the aggregate yield monitoring column on the right side of FIG. 11 are filled with the time at which the crop presently contributing to the aggregate yield for the current measurement interval or time interval previously arrived at feeder house 518. In the example illustrated, the crop arriving at feeder house 518 at time 23 (the value contained in the aggregate yield monitoring column on the right side of FIG. 11) contribute to the aggregate yield value at time 33 (as indicated in the left most time column), reflecting the 10 second travel time from feeder house 518 to the particular aggregate yield monitor or sensor being utilized to detect aggregate yield.

As shown by the shading in FIG. 11, the aggregate yield value as detected during time 33 is an aggregate of the crop arriving at feeder house 518 at time 23. As further shown by FIG. 11, the crop arriving at feeder house 518 at time 23 were initially harvested by the different row unit 614, Rows 1-8, at different times due to the differences in time for the crop to travel to feeder house 518. In the example illustrated, crop arriving at feeder house 518 at time 23 were harvested by Rows 1-4 at times 17, 19, 21 and 23, respectively, from different geo-referenced regions that were traversed by harvester 22 during the different times 17, 19, 21 and 23, respectively. Likewise, crops arriving at feeder house 518 at time 23 were harvested by Rows 5-8 at times 23, 21, 19 and 17, respectively, from different geo-referenced regions that were traversed by harvester 22 during the different times 23, 21, 19 and 17, respectively. As indicated by shading, the aggregate yield measured at a particular time, for a particular measurement interval, is the result of the aggregation of crop harvested from geo-referenced regions in the pattern or shape of a chevron, a line or strip in the shape of a V or an inverted V, depending on orientation.

Yield allocation module 52 of yield allocation and control unit 742 allocate or apportion the aggregate yield detected during each time or measurement interval back to earlier geo-referenced regions based upon the travel times of the crop from different portions of harvester 422, such as from the different row unit 614. For example, in the example travel time scheme shown in FIGS. 9 and 10, unit 742 allocates the measured aggregate yield from measurement interval or time 33 back to the geo-referenced regions that were traversed by head 516 of harvester 422 during measurement intervals or times 17, 19, 21 and 23. Similarly, unit 742 allocates the measured aggregate yield from measurement interval or time 34 back to geo-referenced regions that were traversed by head 516 of harvester 422 during measurement intervals or times 18, 20, 21 and 23, allocate the measured aggregate yield for measurement interval or time 35 back to geo-referenced regions that were traversed by head 516 of harvester 422 during measurement intervals or times 19, 21, 22 and 23, respectively, and so on. As shown by shading in FIG. 11, unit 742 of portions or allocates the aggregate yield from a particular measurement interval or time to previously traversed geo-referenced regions which are part of a chevron shape.

In the example yield allocation scenario illustrated in FIGS. 9 and 10, the measurement interval is one second. In other implementations, the measurement interval is less than one second. In one implementation, the measurement interval is between 0.05 seconds and 0.1 seconds to provide spatial resolution of approximately 2 foot×2 foot with a global positioning system position error of less than 0.5 inches, facilitating per plant allocations. In circumstances where row spacing is 18-38 inches for corn and plant spacing within a row is 6 inches on up spatial resolution of 2 foot by 2 foot contains several plants.]

In other implementations, other measurement intervals are employed. For example, in other implementations, harvester 422 may move through a field at 2 mph, such that it is traveling just under 3 feet/second. In one implementation, position location system 726 comprises a GPS receiver that with corrections reports position with 0.5 inch accuracy at a 10 Hz rate or approximately every 4 inches. Corn is often planted with 6 inch seed separation and 24 inch row separation. As a result, the GNSS or other positioning system reporting rate and spatial accuracy, combined with row crops of known separation, facilitates the allocation of aggregate yield to individual plants.

In the example yield allocation scheme shown in FIGS. 9 and 10, the travel times for crops from different row units 614 to feeder housing 518 is illustrated as being uniform across the different transversely located the units 614. Rows 1-8, with the travel time being uniformly two seconds per row away from the center rows 3, 4. In other implementations, different harvesters may have different travel times. Moreover, such travel times on the same harvester may vary at different times and from row to row. For example, harvester 22 and its conveyors, including gathering unit 62, 634 and auger 615, may operate at different speeds at different times as harvester 22 is traversing a field. In the example illustrated, sensors 744 and 746 output signals indicating such different speeds at different times, wherein yield allocator and control unit 742 adjusts the allocation or apportionment of the aggregate yield to the different geo-referenced regions based upon the different speeds or crop travel times as indicated by sensors 744, 746.

At yet other times, harvester 422 may be traveling across the side of a hill, resulting in head 516 having an uneven roll or roll that is not level. Roll sensor 748 outputs signals indicating such an uneven roll. In such a circumstance, crops harvested by row units 614 closer to the top of the hill may have shorter travel times to feeder housing 518 as compared to crops harvested by row units 614 closer to the bottom of the hill due to gravity. Yield allocator and control unit 742 adjusts the allocation or apportionment of the aggregate yield to the different geo-referenced regions based upon the different travel times based upon the roll of head 516 at the time that the particular geo-referenced regions are crossed by head 516.

At yet other times, harvester 422 may be traveling up a hill or down, resulting in head 516 undergoing pitch, not being level, but leaning upward or leaning downward. Pitch sensor 750 outputs signals indicating such a pitch. In circumstances where head 516 is inclined going uphill, crops harvested by row units 614 may have shorter travel times to feeder housing 518 due to the assistance of gravity. Likewise, in circumstances where head 516 is declined going downhill, crops harvested by row units 614 may have longer travel times to feeder housing 518 due to the resistance of gravity. Yield allocator and control unit 742 adjusts the allocation or apportionment of the aggregate yield to the different geo-referenced regions based upon the different travel times based upon the pitch of head 516 at the time that the particular geo-referenced regions are crossed by head 516. In addition, time for crops to travel from the feeder house to aggregate yield sensor may also vary with time and may be adjusted with data from pitch sensor, roll, sensor, or other sensors.

In one implementation, travel time adjustments resulting from changes in pitch or roll of harvester head 516 are additionally based upon the type of crop being harvested, the cleanliness of the crop being harvested, the moisture content of the crop being harvested and the total initial aggregate yield allocations to a particular geo-referenced region. For example, the type of crop being harvested may impact the speed at which harvested crops flow transversely along head 516 are rearwardly along head 516. The amount of foreign material, such as chaff, in the grain being harvested and/or the moisture content of the grain being harvested may further impact the speed at which grain flows. The volume or amount of grain being carried by head 516 may also impact the speed at which harvested crops flow transversely along head 516 or rearwardly along head 516. In one implementation, yield allocation in control unit 742 differently adjusts for changes in pitch and/or roll of head 516 based upon the type of crop being harvested, the cleanliness and/or moisture level of the crop being harvested and/or the volume or mass of the aggregate yield.

Yield allocation in control unit 742 outputs aggregate yield allocations. In the example implementation, yield allocation and control unit 742 performs prescriptive harvester adjustment, adjusting the operational parameter settings of harvester 422 based upon the aggregate yield allocations. In one implementation, yield mapping module 56 of unit 742 present and display yield maps, such as yield map 120 (shown in FIG. 1), on display 730 and/or store such maps in data storage 58 of unit 742.

In one implementation, yield allocation and control unit 742 additionally bases the allocation of aggregate yield upon yield allocation factors or weightings for different geo-referenced regions and/or the plants growing in such different geo-referenced regions. In one implementation, yield allocation a control unit 742 identifies delays between crop harvest and aggregate yield measurement for each row as harvested by each row unit 614. Such time delays may be variable due to pitch and/or role of header 518 as well as crop processing elements. Unit 742 additionally defines a data interval. Based upon collected time stamped individual geo-referenced region yield predictions and time-stamped aggregate yield data, yield allocation control unit 742 assigns or allocates the aggregate yield for the measurement interval to individual plants and/or individual geo-referenced regions. In one implementation, such time stamped individual geo-referenced region yield prediction data and time stamped aggregate yield data or additionally location stamped, indicating the geo-referenced location based upon signals from localization input 726.

In one implementation, harvester 422 additionally comprises sensor 770 and/or sensor 772. Sensors 770 and 772 outputs signals indicating one or more characteristics of individual plants being harvested or groups of plants as they are being harvested. In such an implementation, yield allocation and control unit 742 utilizes such signals to identify or predict yield differences between different plants and/or different groups of plants being harvested by the different portions, row units 614, of harvester 422. In one implementation, each of the row units 614 includes sensor 770 and/or sensor 772. In another implementation, multiple row units 614, forming different subsets of the entire set of row units 614, each share a sensor 770. Based upon the predicted yield differences, yield allocation and control unit 742 adjusts the allocation or apportionment of the aggregate yield amongst the different geo-referenced regions from which plants were harvested by the different row units 614.

In one implementation, sensor 770 comprises a sensor that interacts, engages or contacts the plants as the plants are being harvested, wherein such interaction results in signals indicating one or more characteristics of the plants being harvested. In one implementation, sensor 772 comprises a sensor that detects one or more characteristics of the plants being harvested without contacting the plants being harvested. For example, in one implementation, sensor 772 comprises a camera or LIDAR that output signals indicating characteristics of the plants being harvested. In such implementations, control unit 742 includes software, code or programmed logic to predict a yield for the different plants or groups of plants based upon signals from sensor 770 and/or sensor 772. The predicted yield is used to apply different weightings to adjust aggregate yield allocation amongst different geo-referenced regions.

In one implementation, each row unit 614 of head 516 includes a sensor 770 that detects a diameter of each of the stalks of the plants being harvested from each of the geo-referenced regions by the different row units 614 or groups of row units 614. One implementation, sensor 772 is configured to detect the diameter of individual stalks. In such an implementation, unit 742 allocates aggregate yield from a particular measurement interval to each of the geo-referenced regions traversed by the different row unit 614 using a weighting that is based upon the detective thickness of the plants harvested by integral unit 614. For example, two geo-referenced regions traversed by harvester 422 during the same measurement interval may receive different aggregate yield allocations due the stalks in one of the geo-referenced regions harvested by one of the row unit 614 being thicker or wider than the stalks in the other of the geo-referenced regions harvested by other row unit 614, where the greater thickness of the stalk is determined as being linked to greater crop yield.

In another implementation, the two geo-referenced regions traversed by harvester 22 during the same measurement interval may receive different aggregate yield allocations from a later measurement interval due to other indications reflecting greater yield. For example, in one implementation, each row unit 614 comprises a sensor 770 that senses an impact of the crop, such as ears of corn, with harvester 422, such a stripper plate 636 of harvester 422. In one implementation, each sensor 770 may comprise an auditory sensor or an accelerometer to detect the impact of the crop with harvester 422. In one implementation, larger or greater impacts producing higher amplitude signals indicate greater mass and are deemed as indicating greater yield. In such an implementation, two geo-referenced regions traversed by harvester 422 during the same measurement interval may receive different aggregate yield allocations from later measurement intervals due to differences in the sensed crop impacts being larger from plants in one geo-referenced region versus impacts from plants in another geo-referenced region. One example of such a crop impact detection system is disclosed in U.S. patent application Ser. No. 13/771,682 filed on Feb. 20, 2013 and entitled CROP SENSING; U.S. patent application Ser. No. 13/771,727 filed on Feb. 20, 2013 and entitled PER PLANT CROP SENSING RESOLUTION; U.S. patent application Ser. No. 13/771,760 filed on Feb. 20, 2013 and entitled CROP SENSING DISPLAY, the full disclosures of which are hereby incorporated by reference.

In yet another implementation, such yield allocation weightings are based upon captured video or images of the plants during harvest. For example, in one implementation, sensor 772 carried by harvester 422 capture images of the plants prior to engaging with harvester 422, wherein such images are analyzed the results of such analysis used to generate and apply yield allocation weightings. For example, in one implementation, light detection and ranging (LIDAR) is used as a basis for estimating yield, wherein the yield estimates are used to generate yield allocation weightings for allocating the sensed aggregate yield to different geo-referenced regions. In other implementations, images of other plant portions are used for yield allocation weightings using preselected our field calibrated conversion factors or both. For example, in other implementations, yield allocation weightings are based upon captured video or images of the size of the year at stripper plate or the size of the plant, wherein plant size correlates to plant mass which correlates to grain mass. In yet other implementations, such weightings are determined based upon other sensed characteristics of plants being harvested by harvester 422.

In another implementation, sensor 770 senses a power characteristic of each of different components across a crop harvesting width of the harvester 422, wherein yield allocation weightings for different plants in different geo-referenced regions are based upon the actual sensed power characteristics and/or differences in the sensed power characteristics of the different components across the harvesting width. For example, harvester 422 may be harvesting a first geo-referenced region with a first row unit 416 or a group of row units 416 and a second geo-referenced region at the same time with a different second row unit 416 or a different second group of row units 416. Due to the first geo-referenced region providing a greater crop yield than the second geo-referenced region, the power consumed or otherwise employed to harvest the crops in the first geo-referenced region in many instances will be greater than the power consumed or otherwise employed to harvest the crops in the second geo-referenced region. As a result, the power consumed or employed by components of the first row unit 416 or first group of row units 416 to harvest the crops in the first geo-referenced region will likely be greater than the power consumed or employed by components of the second row unit 416 or the second group of row units 416 to harvest the crops in the second geo-referenced region. Harvester 422 utilizes sensors 770 across the harvesting width to sense a power characteristic associated with each of different components across the harvesting head and applies different yield allocation weightings to different geo-referenced regions based upon the actual sensed power characteristics and/or a relationship between the sensed power characteristics of the different components of the different individual row units or groups of row units.

Examples of components across the harvesting width of harvester 422 for which power characteristics are be sensed include, but are not limited to, a snap roller, a stalk chopper, and a cutter bar. Examples of sensors used to detect or sense the power characteristics that harvester 422 uses to weight yield allocation amongst different geo-referenced/time stamped regions include, but are not limited to, a voltage sensor, a current sensor, a torque sensor, a hydraulic pressure sensor, a hydraulic flow sensor, a force sensor, a bearing load sensor and a rotational sensor. In some implementations, harvester 22 weights yield allocation amongst different geo-referenced regions, including timestamp regions, based upon sensed power characteristics of more than one type of crop interacting component across a harvesting width of harvester 422. In such implementations, using sensed power characteristics from more than one crop interacting component in each transverse portion of the harvesting width results in greater weighting assignment accuracy amongst the different geo-referenced/timestamp regions harvested by the different transfers portions of the harvesting width.

In yet other implementations, yield allocation weightings are based upon historical plant data acquired for the different geo-referenced regions prior to harvesting. Such historical plant data is acquired during field operations at any time from planting up to harvesting. For example, during field operations such as cultivation or the application of herbicide, insecticide and/or fertilizer, one or more plant characteristics are detected are sensed and stored. Different yield allocation weightings are determined based upon such historical data. Certain plant characteristics taken at various times are linked to greater yield. For example, taller plants, thicker plants, greener plants may all be linked to greater yield. In such an implementation, if a first geo-referenced region traversed by harvester 422 during a measurement interval is associated with historical data indicating that the region contained taller plants, thicker plants and/or greener plants during cultivation and/or during the application of herbicide, insecticide, fertilizer, as compared to a second geo-referenced region traversed by harvester 422 during the same measurement interval, yield allocation module 52 of the yield allocation and control unit 742 applies a larger region yield allocation weighting to the first geo-referenced region as compared to the second geo-referenced region. In one implementation, such historical data may additionally or alternatively be acquired through overhead or aerial surveillance of plants within a field prior to harvesting.

FIG. 12 schematically illustrates an example crop sensing system 820. Crop sensing system 820 outputs crop data and field maps with an enhanced resolution. In an example embodiment, the term "resolution" refers to the level of detail with regard to crop data and/or field maps. Resolution for crop data or field maps is determined by the smallest unit for which an attribute is sensed or for which an attribute is derived. Generally, the smaller the unit, the greater the resolution. Crop sensing system 820 outputs crop data and maps a field using sensed or derived attributes and/or identified conditions for individual units or portions of the field having a width less than a utilized crop harvesting width of a harvester. For example, even though a harvester may have a harvesting swath of 12 rows, crop sensing system 820 may output crop data or field maps providing crop attributes such as, yield, for less than 12 rows, such as on a row-by-row basis or even a plant-by-plant basis. Crop sensing system 820 may be similarly implemented with respect to non-row crops and non-row harvesters. The greater crop data resolution provided by crop sensing system 820 facilitates more advanced and sophisticated crop management.

Crop sensing system 820 comprises an agricultural machine, an example of which is the illustrated harvester 822. Crop sensing system 820 further comprises display 824, input 826, processor 830 and memory 828. Harvester 822 comprises a mobile machine configured to travel across a field or plot of land while harvesting a crop. Harvester 822 comprises head 834, harvester head components 835A-835H (collectively referred to as components 835) and sensors 836A-836H (collectively referred to as sensors 836). In other implementations, crop sensing system 820 may comprise other types of agricultural machines.

Head 834 comprises a mechanism configured to gather and harvest a crop along a swath. The swath of head 834 has a utilized width, Wu, when harvesting crops. In an example embodiment, the utilized width Wu constitutes that portion of the length or swath width that is being utilized to harvest crops at a particular time. Although in most instances, the utilized width Wu is equal to the physical width of the swath of head 834, in some circumstances, the utilized width Wu may constitute only a portion of the swath of head 834, such as along an end row, waterway, previously harvested transport corridor, and/or the like.

Harvesting components 835 comprise various mechanisms for harvesting, such as mechanisms to sever or separate the crop from a remainder of a plant. Such mechanisms may include knives or blades, stripper plates, rollers, snapping roles, augurs, gathering chains or belts and/or the like. In one implementation, head 834 comprises a corn head for a combine, wherein the corn head separates ears of corn from the remaining stalk. In another implementation, head 834 comprises a head having stripper plates or other mechanisms to sever other types of ears from associated stalks. In one implementation, the term "ear" refers to a seed-bearing part of a plant, such as ears of corn, seed laden flowers such as sunflowers, pods and the like. In another implementation, head 834 comprises components to separate cotton from a cotton plant. In another implementation, head 834 comprises components to separate a sugar or oil bearing plant stalk from plant leaves. In another implementation, head 834 may comprise a grain head for a combine, wherein the grain along with the stalk is severed and subsequently threshed by the combine. In other implementations, head 834 and components 835 may have other configurations. For example, although head 834 is illustrated as being located at a forward end of harvester 822 and as being interchangeable with other heads (facilitating the change of corn and grain heads), in other implementations, head 834 may be supported at other locations by harvester 822 and/or may be a permanent, non-interchangeable component of harvester 822.

Sensors 836 comprise mechanisms to sense or detect one or more power characteristics of their associated harvesting components 835. Each of sensors 836 output signals based upon sensed power characteristics of the associated one or more harvesting components 835. Examples of sensors 836 include, but are not limited to, a voltage sensor, a current sensor, a torque sensor, a hydraulic pressure sensor, a hydraulic flow sensor, a force sensor, a bearing load sensor and a rotational sensor. Such power characteristics vary based upon characteristics of the plants crops presently being harvested. For example, plants having thicker stalks are often associated with greater yield. Plants having thicker stalks are also typically associated with larger power characteristics. In particular, the components that sever the thicker stalks, chop the thicker stalks and/or convey either the grain or the associated biomass consume larger amounts of power or require larger forces as compared to components interacting with plants having thinner stalks and lower yields. The larger amount of power to sever the stalk or remove portions of the plant from the stalk is in the form of an increase in voltage, an increase in electrical current, an increase in hydraulic pressure flow, and/or increase in a load or force. Sensors 836 detect the larger power characteristics and output corresponding signals to processor 830.

Each of sensors 836 senses one more crop attribute values for crops harvested by a corresponding distinct portion of the utilized width Wu. In the example illustrated, each of sensors 836 senses a power characteristic of plant interacting components which indicates a crop attribute for plants along an individual row, providing "per row" crop attributes. As indicated by partitioning 844, the utilized width Wu is partitioned or divided into 8 equal portions P1-P8, such as row units, wherein sensors 836A-836H each sense power characteristics of components 835 which interact with crops or plants from portions P1-P8, respectively. In the example illustrated, each portion or each row unit includes a dedicated component 835 and a dedicated sensor 836. In other implementations, components may be shared amongst different portions or row units. Likewise, sensors may be shared amongst multiple components or multiple row units. In some implementations, in lieu of providing per row crop attributes, sensors 36 shared amongst rows alternatively sense power characteristics of crop or plant interacting components to determine crop attributes for groups of rows less than the total harvesting width Wu. Crop attributes comprise grain yield and/or biomass yield.

Although head 834 is illustrated as including eight sensors, in other implementations, head 834 may include a greater or fewer number of such sensors along the physical width or swath of head 834. For example, a crop row harvester may have greater than or less than eight rows, wherein the head of the harvester may similarly divide with greater than or less than eight row sensing sensors. Although head 834 is illustrated as being partitioned into equal portions, in other example embodiments, head 834 is partitioned into unequal portions, wherein sensors sense power characteristics for crop interacting components for the unequal portions. For example, in another implementation, one of sensors 836 senses or detects power characteristics for crop interacting components that interact with an individual row while another sensor 836 senses power characteristics for crop interacting components that interact with a plurality of rows.

As shown by FIG. 12, in some implementations, each of sensors 836 offers a degree of crop sensing resolution by being configured to detect how power characteristics of crop interacting components change when interacting with each individual plant as harvester 822 traverses a field, providing an indication from which a per plant grain or biomass yield estimate is determined. As indicated by FIG. 13, in some implementations, sensors 836 may additionally or alternatively sense changes in power characteristics of crop interacting components when interacting with sets or collections 848 of plants based upon time, distance, a number of plants, and/or the like to reduce the amount of data that is processed or stored. Aggregating individual plant data may also improve useability of the data by eliminating noise in the data.

Display 824 comprises a device by which information may be visually presented to an operator of harvester 282 or to a remotely located monitor/manager/operator of harvester 822. Display 824 may comprise a monitor or screen which is stationary in nature or which is mobile in nature. In one implementation, display 824 is carried by harvester 822 along with the operator. In another implementation, display 824 comprises a stationary monitor remote from harvester 822. In yet other implementations, display 824 may be mobile in nature, being provided as part of a computer tablet, smart phone, personal data assistant (PDA) and/or the like.

Input 826 comprises one or more devices by which controls and input may be provided to processor 830. Examples of input 826 include, but are not limited to, a keyboard, a touchpad, a touch screen, a steering wheel or steering control, a joystick, a microphone with associated speech recognition software and/or the like. Input 826 facilitates the input of selections, commands or controls. In implementations where harvester 822 is remotely controlled or remotely steered, input 826 may facilitate such remote steering.

Memory 828 comprises a non-transient or non-transitory computer-readable medium or persistent storage device for storing data for use by processor 830 or generated by processor 30. In one implementation, memory 828 may additionally store instructions in the form of code or software for processor 830. The instructions may be loaded in a random access memory (RAM) for execution by processor 830 from a read only memory (ROM), a mass storage device, or some other persistent storage. In other embodiments, hard wired circuitry may be used in place of or in combination with software instructions to implement the functions described. For example, at least regions of memory 828 and processor 830 may be embodied as part of one or more application-specific integrated circuits (ASICs). In one implementation, memory 828 is carried by harvester 822. In other implementations, memory 28 may be provided remote from harvester 822.

In the example illustrated, memory 828 comprises data storage portion 852, correlation module 854, condition detection module 856, display module 858 and operations adjustment module 860. Data storage portion 852 contains historical data, such as lookup tables, facilitating analysis of data and information sensed by sensors 836. Data storage portion 852 is further configured to store the power characteristic values directly sensed by sensors 836 and crop attribute values derived from the directly sensed power characteristic values using correlation module 854. Such stored information may be in various formats such as tables, field maps and/or the like. Data storage portion 852 may additionally store various settings and operator preferences.

Correlation module 854, condition detection module 856, display module 858 and operations adjustment module 860 comprise programming, software or code stored on a non-transitory medium for directing the operation of processor 830. Correlation module 854 instructs processor 830 in the correlation of one or more directly sensed power characteristic values detected by sensors 836 to derived crop attribute values. In other words, correlation module 854 instructs processor 30 and the derivation of crop attribute values, such as grain or biomass yield and/or the like, from directly sensed power characteristic values. In one implementation, correlation module 854 directs processor 830 to consult a lookup table in data storage portion 852 to correlate a power characteristic as detected by sensors 836 to a grain mass or grain yield value, the derived crop attribute value. In another implementation, correlation module 854 directs processor 830 to carry out one or more algorithms/mathematical equations using a sensed power characteristic, and possibly using other additional factors, to derive a grain mass or biomass, mass other than grain, yield of the plant. In other implementations, correlation module 854 directs processor 830 to derived crop attribute values from directly sensed power characteristic values in other fashions.

Condition detection module 856 directs processor 830 in the identification of field and/or crop conditions based upon the directly sensed power characteristic values or the derived crop attribute values. Examples of such field/crop conditions include, but are not limited to, the absence of plants, a field washout condition, an area of the field having yields suffering from wheel compaction beyond a predetermined threshold, the existence of a weed patch, the existence of yield loss due to inappropriate chemical application, and/or the like. In one implementation, condition detection module 856 directs processor 830 to consult a lookup table in data storage portion 852 to correlate a power characteristic as detected by sensors 836 and/or a derived grain mass or grain yield value, the derived crop attribute value, to one of various predefined conditions, examples of which are set forth above. In another implementation, condition detection module 856 directs processor 830 to carry out one or more algorithms and/or mathematical equations using a directly sensed power characteristic value and/or a derived crop attribute value and to further compare the resulting calculation to one or more predefined thresholds to identify a field and/or crop condition. In other implementations, condition detection module 856 may direct processor 830 to identify or detect crop and/or field conditions in other fashions.

Display module 858 instructs processor 830 to generate control signals causing display 824 to present various information and/or prompts to an operator. For example, display module 858 may cause processor 830 to prompt an operator to select whether or not and how individual power characteristic data is to be aggregated, how data is to be displayed (graph, chart, field map), what conditions are to be identified, how the operator is notified or alerted to such conditions, where such data is to be stored and/or the like. Display module 858 further instructs processor 830 in the display of data per operator preferences.

Operations adjustment module 860 comprises code or programming which directs processor 830 to automatically generate control signals adjusting operational parameters of harvester 822 based upon directly sensed power characteristic values or derived crop attribute values. In one implementation, operations adjustment module 860 generates control signals independently adjusting operational parameters of distinct portions of head 834 along its utilized width Wu. For example, operations adjustment module 860 may adjust the operational parameters of one row unit of head 834 independent of or differently with respect to another row unit of head 834 based upon directly sensed or derived power characteristic values for the crop interacting components of the different row units. For example, operations adjustment module 860 may, automatically, in response to sensed or derived power characteristic values for crop interacting components of a particular row unit, generate control signals for an actuator coupled to stripper plates of the row unit to adjust the spacing of stripper plates. This adjustment of stripper plates for the particular row unit may be independent of and different from the spacing adjustment of other stripper plates for other row units. As a result, the enhanced crop sensing resolution provides enhanced more refined control over the operation of harvester 822 to better harvest crops.

Processor 830 comprises one or more processing units configured to carry out instructions either hardwired as part of an application-specific integrated circuit or provided as code or software stored in memory 828. In the example illustrated, display 824, input 826, memory 828 and processor 830 are each illustrated as being part of and carried by harvester 822. In other implementations, one or more of such components may alternatively be located remote from harvester 822 and in communication with harvester 822 in a wireless fashion. In some implementations, some of the aforementioned functions of processor 830 in memory 828 may be shared amongst multiple processors or processing units and multiple memories/databases, wherein at least some of the processors and memories/databases may be located remote with respect to harvester 822.

FIG. 14 is a flow diagram illustrating an example method 900 that may be carried out by system 820 to sense and estimate grain and/or biomass yield. As indicated by block 910, processor 830 receives sensed power characteristic values for each of multiple crop interacting components across portions of the utilized width Wu of head 834 of harvester 822. For example, in an implementation where partitioning 844 is employed, sensor 836A provides processor 830 with a first power characteristic value for crop interacting components that interact with crops along portion P1. Sensor 836B provides processor 830 with a second sensed power characteristic value for crop interacting components of portion P2. Sensors 836C-836H similarly provide processor 830 with distinct power characteristic values for their associated crop interacting components of portions P3-P8, respectively. In some implementations, the sensed power characteristic values may comprise a sensed voltage, a sensed electrical current, the sensed torque, a sensed hydraulic pressure, a sensed hydraulic flow and/or a sensed load of one or more crop interacting components.

As indicated by block 912, processor 830, following instructions provided by correlation module 854, utilizes the received power characteristic values (PC) for each of the crop interacting components of the different portions to derive crop attribute values (CAVs) for each of the portions. FIG. 15 is a graph illustrating one example relationship of a power characteristic and biomass or grain yield. In the example illustrated, power sensed in the form of Watts, wherein the wattage of power being utilized by the crop interacting component for a particular period of time corresponds to biomass and/or grain yield for the particular period of time. In one implementation, an average, median or other statistical value of power consumption for a crop interacting component during a predetermined period of time is used by processor 830 to estimate a grain and/or biomass yield for the predetermined period of time. In yet other implementations, an average, median or other statistical value of power consumption for a crop interacting component during a predetermined length of travel of harvester 822 or such components interacting with a predetermined number of plants is used by processor 832 to estimate a grain and/or biomass yield for the predetermined travel length or predetermined number of crop interactions.

As noted above, the crop attribute values comprises an estimate for grain yield and/or an estimate for mass other than grain/biomass yield. In such an implementation, processor 830 derives an estimated yield for portions that are harvesting a crop. For example, in an implementation where partitioning 844 is employed, processor 830 derives a first yield value for portion P1, a second yield value for portion P2, a third yield value for portion P3 and so on.

As indicated by block 914, processor 830 generates control signals, following the instructions contained in display module 858, to store or display the derived crop characteristics. In one implementation, processor 830 stores the crop attribute values derived from the sensed power characteristic in data storage portion 852 of memory 828. In one implementation, processor 830 transmits the derived crop attribute values to a remote database or memory location via a wide area network, such as a wired or wireless connection. In some implementations, the root or base power characteristic data is also stored and/or transmitted. In some implementations, the derived crop attribute values are further displayed on display 824. In some implementations, a visible or audible alert or notice may be output by display 824 in response to the derived crop attribute value for a particular portion satisfying a predefined threshold. For example, if a derived crop yield for a particular portion P, such as a particular row unit of head 834, falls below a predefined threshold, the operator may be provided with an alert or notice possibly indicating problems with the operation of the particular row unit.

As noted above, because system 820 determines crop attributes for individual portions of the harvesting width, such as individual rows or individual plants (or aggregations of plants along a row), system 820 provides an operator with more detailed information having a higher resolution, allowing the operator (or the harvesting machine automatically) to make adjustments to the setting of the harvester on a row-by-row basis to adapt to different conditions that may exist on a row-by-row basis. The operator may further utilize such information to correlate the yield results for individual rows during harvest to individual row settings of other operations such as planting, tillage, fertilizer, insecticide, or herbicide application and/or the like. As a result, row-by-row settings for such other equipment operations such as planter, tillage, fertilizer, insecticide, or herbicide application may be subsequently adjusted based upon the row-by-row harvesting information. For example, strip till, planters, fertilizer, insecticide, herbicide applicators and/or the like may have given rise to uneven emergence or crop development rates, wherein row level sensing information allows an operator to determine that a problem exists, to identify causes and to identify solutions prior to the next harvesting season.

Such information may also be utilized to better calibrate other crop harvesting yield estimating devices. For example, per-row yield estimates may be used with yield data captured elsewhere on the machine, such as a grain yield sensor mounted on the clean grain auger, or off the machine, such as a weigh scale at a grain storage facility. The combination of this data may be used for purposes such as sensor calibration and post-harvest data processing.

Figure 16:
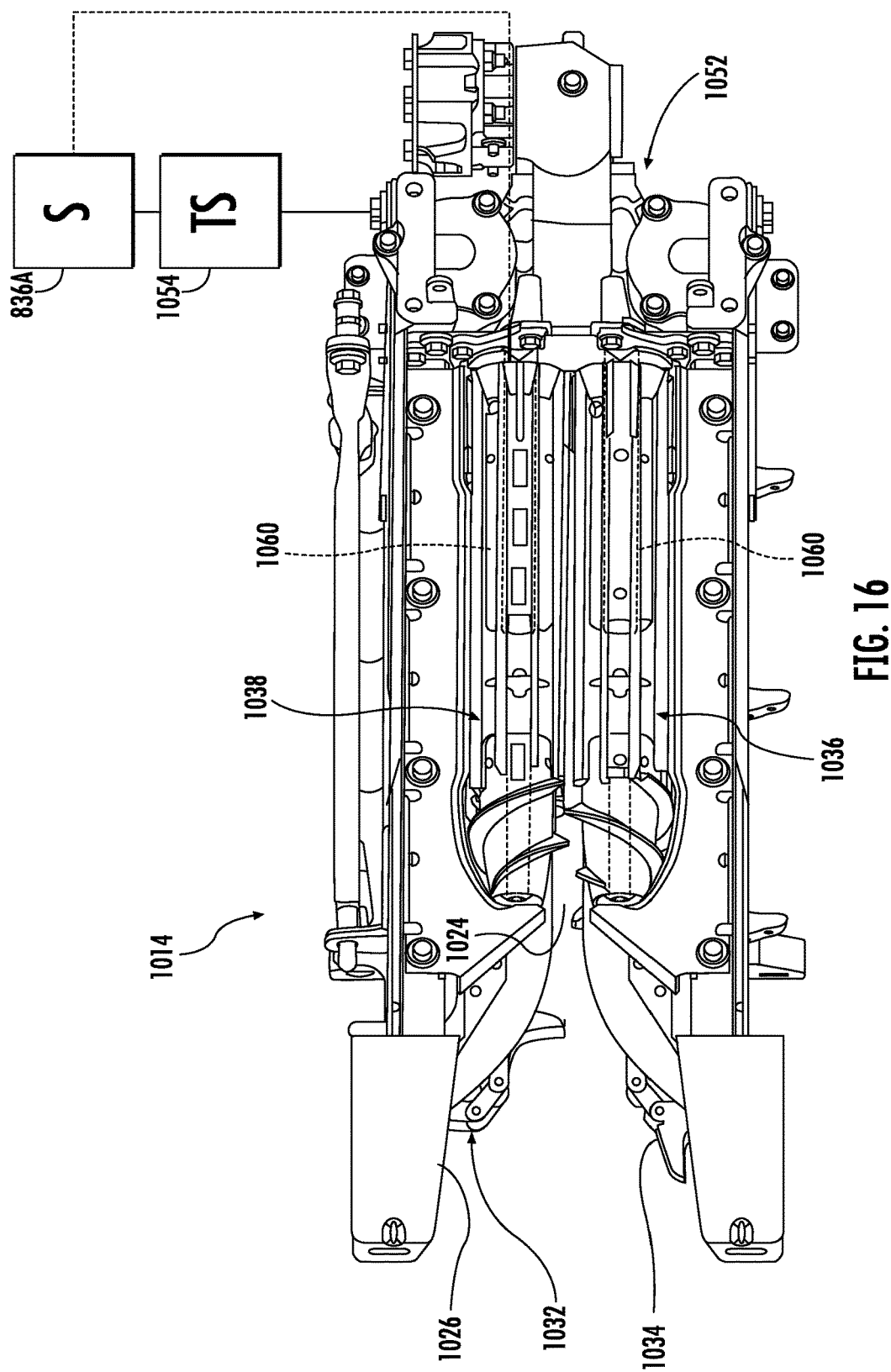
FIG. 16 is a bottom view of an example row unit of a harvester of the crop sensing system of FIG. 12.
Figure 17:
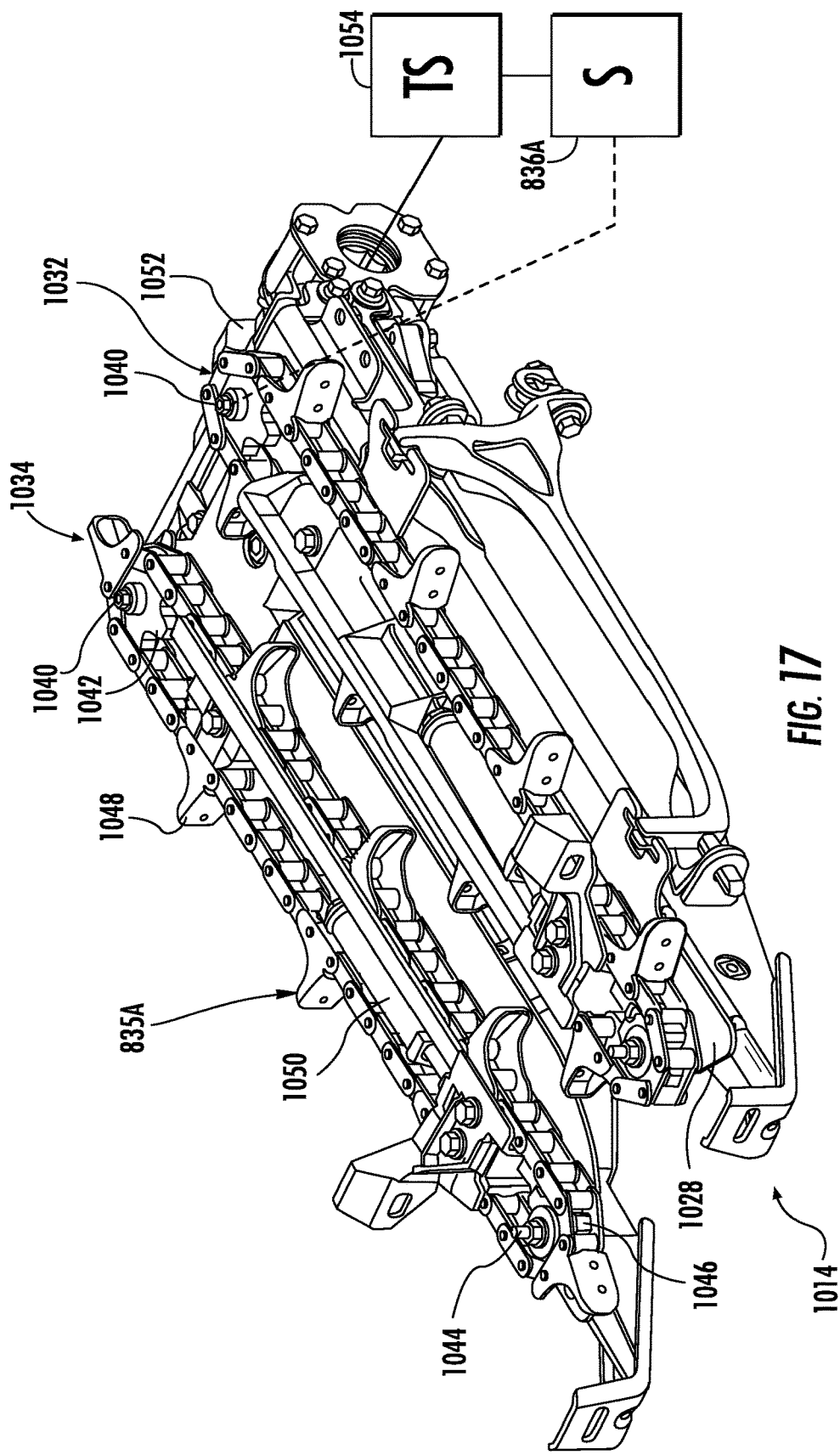
FIG. 17 is a top perspective view of the row unit of FIG. 16.

FIGS. 16 and 17 illustrate examples of crop interacting components 835A of harvester 822, for example, right and left gathering units 1032, 1034 and snapping rolls 1036, 1038. FIGS. 16 and 17 illustrate an example row unit 1014 of harvester 822 described above. Row unit 1014 comprises frame 1026, right and left stripper plates, also known as deck plates, 1028, 1030, right and left gathering units 1032, 1034 and snapping rolls 1036, 1038 (shown in FIG. 16). Frame 1026 comprise a U-shaped member supporting stripper plates 1028, 1030 as well as right and left gathering units 1032, 1034 and snapping rolls 1036, 1038.

Stripper plates 1028, 1030 comprise plates having inner edges spaced apart so as to define narrow throat 1024. Throat 1224 receives cornstalks of an aligned row as row unit 1214 moves along a row of crops. As row unit 1014 is moved along the row, the stalks are drawn down through throat 1024 with the assistance of snapping rolls 1036, 1038 (shown in FIG. 16) such that ears of corn carried by the stalk impact the stripper plates and are separated from the stalk. As noted above, in some implementations, an actuator may be coupled to stripper plates to automatically adjust the spacing a stripper plates 1028, 1030 in response to control signals from processor 830 based upon a sensed power characteristic values for the particular row unit 1014.

Right and left gathering units 1032, 1034 gather the ears of corn and transport such ears rearwardly towards and auger, such as auger 615 shown in FIG. 8. In the example illustrated, each of gathering units 1032, 1034 comprises driveshaft 1040, drive sprocket 1042, idler shaft 1044, idler sprocket 1046, gathering chain 1048, and chain tensioning assembly 1050. Each of drive shafts 1040 extends from and is driven by a gearbox 1052 to rotationally drive sprocket 1042. Gearbox 1052 is itself operably coupled to a torque source 1054 (schematically shown) which supplies torque to rotate driveshaft 1040 through gearbox 1052 Each of drive shafts 1040 extends through a corresponding opening 1054 of frame 1026 (shown in FIG. 16). Drive sprockets 1042 cooperate with idler sprockets 1046 to support and drive gathering chain 1048.

Idler shafts 1044 are rotationally supported by chain tensioning assemblies 1050. Idler shafts 1044 rotationally support idler sprockets 1046. Chain tensioning assemblies 1050 adjustably support idler sprockets 1046 for movement between different fore and aft positions to adjust the tension of gathering chains 1048. Snapping rolls 1036, 1038 are mounted to a pair of drive shafts 1060 with project forwardly from gearbox 1052. Torque source 1054 supplies torque to driveshaft 1060 through gearbox 1052 to rotate snapping rolls 1036, 1038. As noted above, snapping rolls 1036, 1038 draw cornstalks down through throat 1024, between stripper plates 1028, 1030. Because ears of corn are too large to pass down through throat 1024, such ears impact stripper plates 1028, 1030 and are detached or severed from the stalks for being gathered by gathering chains 1048.

In the example shown in FIGS. 16 and 17, sensor 836A senses a power characteristic associated with crop interacting components 835A. In the example illustrated, sensor 836A senses a power characteristic associated with the driving of gathering units 1032, 1034 and/or snapping rolls 1036, 1038. In one implementation in which torque source 1054 comprises an electric motor, sensor 836A senses changes in electrical current or voltage of the electrical motor, wherein the changes indicate changes in crop attributes such as stalk thickness, which is used by processor 830 to estimate grain and/or biomass yield. In one implementation which torque source 1054 comprises a hydraulic or pneumatic motor, sensor 836A senses changes in hydraulic or pneumatic flow rate and/or changes in hydraulic or pneumatic pressure of the hydraulic motor, wherein the changes indicate changes in crop attributes such as stalk thickness, which is used by processor 830 to estimate grain and/or biomass yield. As schematically indicated by broken lines, in other implementations, sensor 836A additionally or alternatively senses physical characteristics of the movement of gathering units 1032, 1034 and/or snapping rolls 1036, 1038. For example, in one implementation, sensor 836A senses changes in the force, bearing or torque being imposed upon gathering units 1032, 1034 and/or snapping rolls 1036, 1038 as a result of crop interaction. Sensor 836A measures or senses force exerted by a crop against a surface, such as snapping rolls 106, 1038, which causes the sensors to deflect or the force being applied to bearings upon which snapping rolls 1036, 1038 are mounted. The sensed forces are correlated with biomass yield or grain yield.

Figure 18:
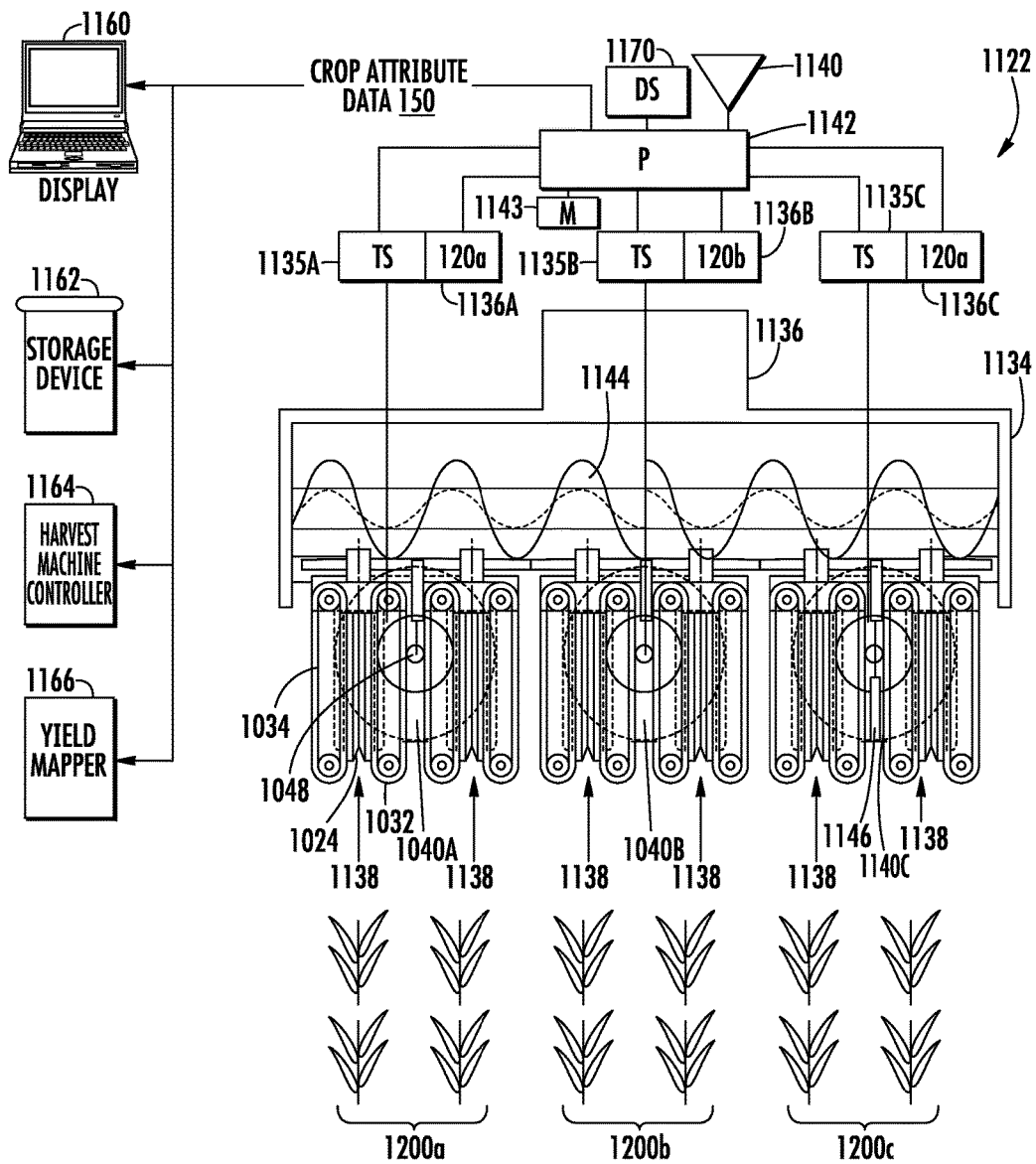
FIG. 18 is a schematic diagram of another example crop sensing system.

FIG. 18 illustrates a portion of harvester 1122, another implementation of harvester 822. Harvester 1122 comprises harvester head 1134, torque sources 1135A, 1135B, 1135C (collectively referred to torque sources 1135), power characteristic sensors 1136A, 1136B, 1136C (collectively referred to as power characteristic sensors 1136), geo-referencing system 1140 and processor 1142. In the example illustrated, head 1134 is configured as an attachment for harvester 1122. In other implementations, head 1134 is fixed as part of harvester 1122. Head 1134 comprises a frame 1136 supporting six picking units or row units 1138 and three stalk choppers 1140a, 1140b, and 1140c (collectively referred to as stalk choppers 1140). Picking units or row units 1138 draw and pick crops which are conveyed rearwardly to auger 1144. Each of row units 1138 is similar to row unit 1014 described above. In one implementation, each of row units 1138 utilizes picking our snapping rolls to draw crops through a picking gap or throat 1024, wherein chain conveyors or gathering units 1032, 1034 transport the crops are plants rearward to screw conveyor or auger 1144. Although harvester 1122 is illustrated as including six row units 1138, in other implementations, harvester 1122 comprises a greater number row units or a fewer number of row units.

Stalk choppers 1140 are supported below row units 1138 to chop or comminute stems or stalks remaining on the field and accelerate plant decomposition. Each of stalk choppers 1140 comprises a knife 1146 rotatably supported by frame 1136 so as to be rotatably driven about a vertical axis 1148. In the example illustrated, each knife 1146 chops or cuts stocks being harvested by two adjacent row units 1138. In other implementations, each row you 1138 may have a dedicated rotatable knife.

Torque sources 1135 supply torque to rotatably drive each of the knives 1146. In the example illustrated, torque sources 1135 comprise electric drives, such as electric motors. In other implementations, torque sources 1135 comprise hydraulic motors or other sources of torque.

Power characteristic sensors 1136 sense power characteristics of torque sources 1135. In the example illustrated, sensors 1136A, 1136B, 1136C sense power characteristics of their associated torque sources 1135A, 1135B 1135C, respectively. Power characteristic sensors 1136 comprise one or more of voltage sensors, current sensors, torque sensors, rotational speed sensors, phase sensors, or other appropriate sensors. Sensors 1136 output signals which are transmitted to processor 1142.

Geo-referencing system 1140 provides geo-referenced data to processor 1142 to associate sensed power characteristics and derived or determined crop attributes, such as biomass yield or grain yield, to particular geo-referenced regions. In one implementation, geo-referencing system 1140 comprises a global navigation satellite system (GNSS). Geo-referencing system 1140 provides data such as global position, speed, heading, time. The data may come solely through processing of navigation satellite signals or may additionally or alternatively use data from sensors such as electronic compass, radar speed sensor, local positioning system, wheel-driven odometer, etc. In another implementation, geo-referencing system 1140 provides time-stamp data linking or associating particular regions of a field to sensed power characteristics and/or derived or determined crop attributes as harvester 1122 traverses a field.

Processor 1142 comprises one or more processing units that follow program logic or code contained in a non-transitory computer readable medium or memory 1143 so as to utilize signals received from sensors 1136 and geo-referencing system 1140 to provide output to display 1160, storage device 1162, harvest machine controller 1164 and/or yield mapper 1166. In operation, as harvester 1122 moves through a crop, stalk chopper 1140A cuts crop 1200a. Stalk chopper 1140B cuts crop 1200b. Stalk chopper 1140C cuts crop 1200c. Power consumed by each of the torque sources 1135 is measured by power characteristic sensors 1136. Signals from sensors 1136 are sent to processor 1142. This data may be in the form of a power value or as any of the physical parameter sensor data in raw, filtered, or otherwise processed form.

Processor 1142 processes data from sensors 1136 and optionally from geo-referencing system 1140 and data source 1170. Data source 1170 comprises supplemental data used by processor 1142 to derive, determine or estimate crop attributes, such as biomass yield or grain yield. In one implementation, data source 1170 includes power/material curves such as in FIG. 15 to convert sensor values to material values. In one implementation, data from sensors 1136 is further normalized to account for harvester speed using data from the referencing system 1140 and data source 1170 such as plant population, plant variety (e.g. stalk toughness).

Processor 130 generates crop attribute data 150 which is correlated to power consumed by torque sources 1135 which is correlated to characteristics of the crop 1200a, 1200b, and 1200c being harvested. Stalk choppers processing larger amount of crop will typically consume greater power. In one implementation, processor 1142 provides output in the form of immediate feedback to a harvesting apparatus operator via display 1160. In one implementation, since harvester 1122 comprises three sections of relative yield, display 1160 may report and display the distribution as three bars. The bars may represent an absolute amount of materials such as bushels of grain or tons of biomass, a deviation from average, or the like.

In another implementation, processor 1142 stores crop attribute data 150, in storage device 1162 for later analysis. In one implementation, storage device 1162 is local persistent storage device carried by harvester 1122. In yet another implementation, storage device 1162 is a remote persistent storage device. Examples of persistent storage devices include, but are not limited to, magnetic disk, solid state non-volatile memory, etc.

In yet another implementation, processor 1142 transmits crop attribute data 150 to harvest machine controller 1164. Harvest machine controller 1164 outputs control signals adjusting the operation of harvester 1122 based upon the received crop attribute data 150. For example, in one implementation, controller 1164, in response to biomass and/or grain yield data, adjusts the operation of torque sources 1135 to individually adjust power supplied to knives 1146. For example, in one implementation, in response to receiving signals indicating that row units 1138A is harvesting a greater volume of biomass or a greater amount of grain, harvest machine controller 1164 automatically outputs control signals increasing the power supplied to knife 1146 of stalk chopper 1140A. In another implementation, controller 64 additionally or alternatively outputs control signals adjusting the speed or torque being supplied to gathering units 1032, 1034 or snapping rolls 1036, 1038 (shown in FIG. 16). Although harvest machine controller before is schematically illustrated as being separate from processor 1142, in some implementations, processor 1142 may serve as part of controller 1164.

In yet another implementation, processor 1142 outputs crop attribute data 1150 to yield mapper 1166. Yield mapper 1166 comprises a computing module that combines crop attribute data and geo-referencing data from geo-referencing system 1140 to generate maps depicting biomass yield and/or grain mass yield across regions of a field. In one implementation, the generated yield map is presented on display 1160. In one implementation, the generate yield map is additionally or alternatively stored in storage device 1162. Although yield mapper 1166 is illustrated as being separate from processor 1142, in some implementations, processor 1142 may serve as part of yield mapper 1166.

Although harvester 1122 is illustrated as comprising processor 1142, in other implementations, processor 1142 and lessor memory 1143 are provided as part of a distributed computing environment power and processor 1142 and memory 1143 alternatively be located remote from harvester 1122, communicating with harvester 1122 in a wireless fashion across a local area network or a wide area network. Similarly, in one implementation, one or more of display 1160, storage device 1162, harvest machine controller 1164 and yield mapper 1166 is located local to harvester 1122, being carried by harvester 1122 as harvester 1122 traverses a field. Likewise, one or more of display 1160, storage device 1162, harvest machine controller 1164 and yield mapper 1166 may also be part of a distributed computing environment, wherein such devices are located remote from harvester 1122 and wherein communication with devices wirelessly occurs across a local area network or a wide area network.

Figure 19:
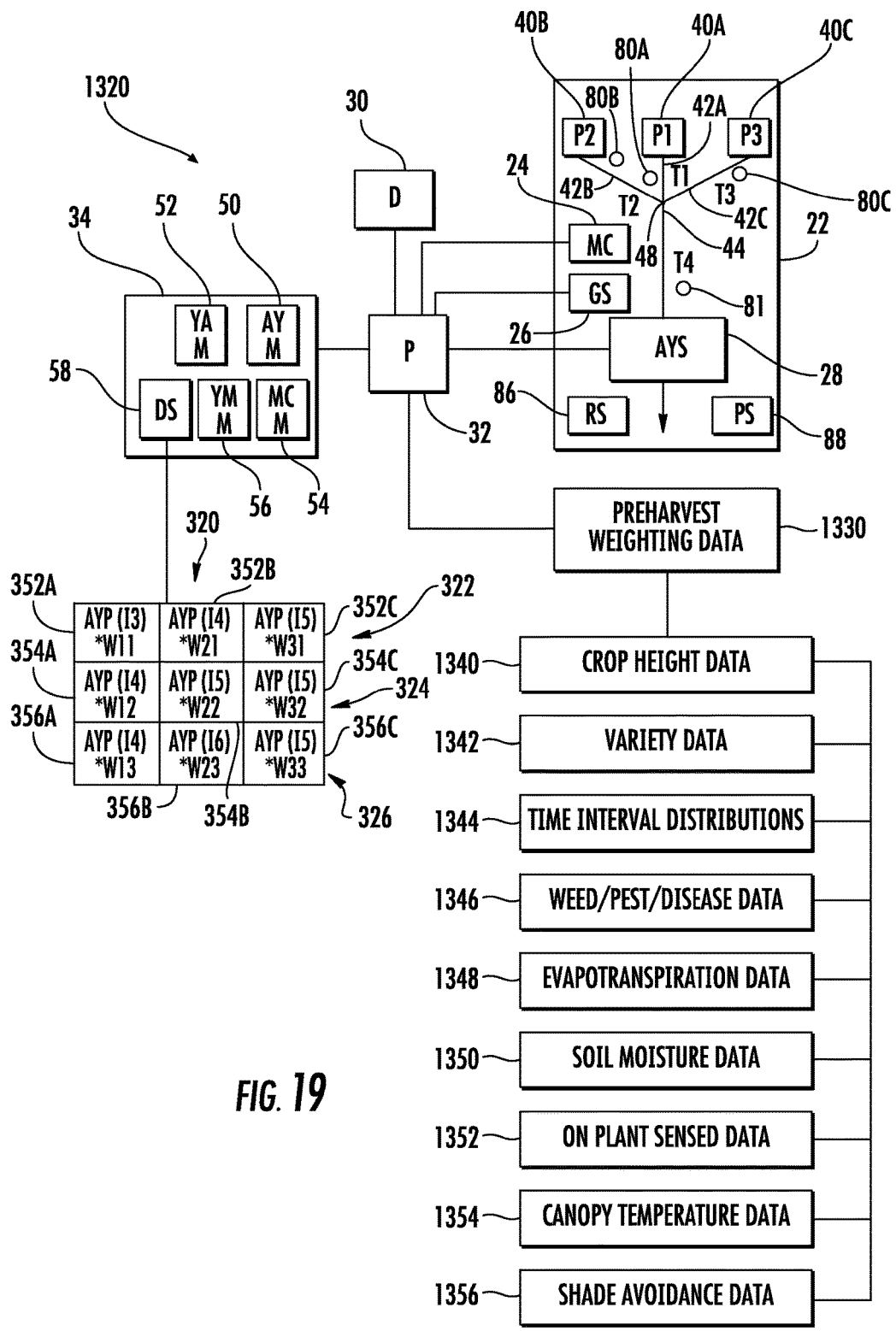
FIG. 19 is a schematic diagram of another example aggregate yield allocation system.

FIG. 19 schematically illustrates aggregate yield allocation system 1320, an example implementation of aggregate yield allocation system 20 described above. As with aggregate yield allocation system 20, aggregate yield allocation system 1320 allocates aggregate yield for a crop, such as grain or other harvested material such as cane billets, cotton and the like, to different geo-referenced locations or regions. Aggregate yield allocation system 1320 is similar to system 20 except that system 1320 is specifically illustrated as carrying out method 300 (shown in FIG. 4), wherein system 1320 applies or utilizes pre-harvest weighting data to allocate the sensed aggregate yield amongst the different geo-referenced locations or regions. Those components of system 1320 which correspond to components of system 20 are numbered similarly.

As shown by FIG. 19, processor 32 receives or otherwise obtains pre-harvest weighting data 1330. Such pre-harvest weighting data comprises historical data acquired for the different geo-referenced regions prior to harvesting. Such historical data is acquired during field operations at any time from planting up to harvesting. It may also be acquired prior to the current growing season. For example, during field operations such as cultivation or the application of herbicide, insecticide and/or fertilizer, one or more plant characteristics are detected or sensed and stored. Different yield allocation weightings are determined based upon such historical data. Certain plant characteristics taken at various times are linked to greater yield. For example, taller plants, thicker plants, greener plants may all be linked to greater yield. In such an implementation, if a first geo-referenced region traversed by harvester 22 during a measurement interval is associated with historical data indicating that the region contained taller plants, thicker plants and/or greener plants during cultivation and/or during the application of herbicide, insecticide, fertilizer, as compared to a second geo-referenced region traversed by harvester 22 during the same measurement interval, yield allocation module 52 applies a larger region yield allocation weighting to the first geo-referenced region as compared to the second geo-referenced region. In one implementation, such historical data may additionally or alternatively be acquired through overhead or aerial surveillance of plants within a field prior to harvesting.

In one implementation, the pre-harvest weighting data is stored in a memory carried by harvester 22. In another implementation, the pre-harvest weighting data is remotely stored, wherein harvester 22 receives or retrieves the pre-harvest weighting data in a wireless fashion, such as across a wireless network.

As further shown by FIG. 19, in the example illustrated, system 1320 is operable in one of multiple user selectable modes, wherein the operator or user is provided with the opportunity to select what pre-harvest weighting data is applied to the allocations of the aggregate yield. In one mode of operation, system 1320 presents selections on display 30 prompting the operator to select more than one type of pre-harvest weighting data, wherein the multiple types of pre-harvest weighting data are concurrently used or aggregated in a weighted fashion to allocate aggregate yield to different geo-referenced regions. In one implementations, system 1320 applies a default weight to each of the multiple types of pre-harvest weighting data collected by the operator for use in the allocation of aggregate yield. In yet another implementation, system 1320 prompts the operator or otherwise provides the operator with the opportunity to customize the allocation by inputting what weightings are to be used for each of the selected types of pre-harvest weighting data.

In still other implementations, system 1320 utilizes different types of pre-harvest weighting data for different portions of the field or different geo-referenced regions when weighting the allocation of aggregate yield. In one implementation, system 1320, via processor 32, display 30 and an input device, prompt the operator or otherwise provide the operator with the opportunity to identify on a map of the field what different available different types of pre-harvest weighting data are to be applied to the different portions or regions of the field. In another implementation, system 1320 automatically selects which of the different types of pre-harvest weighting data are utilized for allocating aggregate yield amongst the different geo-referenced regions. In one implementation, system 1320 automatically selects which of the different types of pre-harvest weighting data are utilized based upon factors such as a level of confidence in the different types of pre-harvest weighting data for the different regions, a level of correlation between yield and one or more yield factors, the level of geographic resolution for the different types of pre-harvest weighting data and/or an extent to which the different types of pre-harvest weighting data statistically differ amongst the geo-referenced regions.

For example, historical data may indicate that certain types of pre-harvest weighting data are not very accurate for particular fields as compared to others. In some implementations, system 1320 may favor particular types of pre-harvest weighting data having higher degrees of geographic resolution as compared to others for particular fields. In some implementations, those types of pre-harvest weighting data that do not exhibit significant differences amongst the different geo-referenced regions to which the aggregate yield is being allocated are disfavored, less likely to be selected by system 1320, due to limited value in estimating yield differences amongst the different geo-referenced regions. In some implementations, differences in the values for each type of pre-harvest weighting data are compared to a predefined threshold, wherein those types of pre-harvest weighting data that have values that are not significantly different across the different geo-referenced regions are not utilized or selected.

As shown by FIG. 19, in the example illustrated, system 1320 provides the operator with the opportunity to various types of pre-harvest weighting data for weighting the aggregate yield allocations amongst the different geo-referenced regions. Examples of different types of pre-harvest weighting data include, but are not limited to, crop height data 1340, variety data 1342, time interval distributions 1344, weed, pest and/or disease data 1346, evapotranspiration data 1348, soil moisture data 1350, on plant sensed data 1352, canopy temperature data 1354 and shade avoidance data 1356.

As described above, in some implementations, the operator may choose different types of pre-harvest weighting datadata for different fields or different regions of the field. In other implementations, system 1320 automatically selects one or more of the different types of pre-harvest weighting datadata for weighting the aggregate yield allocations amongst the different geo-referenced regions based upon one or more predetermined criteria. In one implementation, system 1320 automatically selects and uses different types of pre-harvest weighting datadata for different fields or different regions of the field based upon such predefined or predetermined criteria.

In circumstances where multiple different types of pre-harvest weighting datadata are selected by the operator or automatically chosen by system 1320, the multiple types of pre-harvest weighting data may be combined or aggregated to determine the particular aggregate yield allocation weighting to be assigned to each geo-referenced region. In one implementation, each of the multiple types of pre-harvest weighting data are equally weighted, wherein the predicted yield for a geo-referenced region is equally based upon each of the different yield predictions from the different types of pre-harvest weighting data. For example, in one implementation, the different yield estimates or predictions for a particular geo-referenced region from the multiple different types of pre-harvest weighting data for that region are averaged. For example, if time interval distributions 1344 predicts a yield of 150 bushels per acre while weed/pest/disease data 1346 predicts a yield of 170 bushels per acre for a particular geo-referenced region, an average yield of 160 bushels per acre ((170+150)/2) would be used for weighting the aggregate yield allocations amongst the different geo-referenced regions.

In another implementation, the predicted or estimated yields for a geo-referenced region from the different types of pre-harvest weighting data are differently weighted. In one implementation, the yield predictions or estimates from those types of pre-harvest weighting data having historically lower levels of accuracy are provided with a lower weight as compared to the yield predictions or estimates from those types of pre-harvest weighting data having historically higher levels of accuracy. In one implementation, the different weightings applied to the different yield estimates from different types of pre-harvest weighting data are uniformly applied across all of the geo-referenced regions.

In another implementation, the different weightings applied to the different yield estimates from different types of pre-harvest weighting data are differently or non-uniformly applied across all of the geo-referenced regions. In other words, the yield predictions from different types of pre-harvest weighting data are differently weighted relative to one another depending upon the geographic location of the geo-referenced region. For example, in one implementation, the yield predictions for geo-referenced regions of a first portion of a field or at a first location, based upon soil moisture data 1350, are given a greater weight as compared to canopy temperature data 1354, while the yield predictions for geo-referenced regions in a second portion of the field or second location, based upon soil moisture data 1350, are given a lesser weight as compared to canopy temperature data 1354.

In one implementation, when combining the multiple different types of data to determine an aggregate yield allocation weighting, system 1320 automatically applies and selects the different weightings applied to the yield estimates from the multiple different types of pre-harvest weighting data for the geo-referenced regions. For example, in one implementation, system 1320 consults a lookup table having stored or historical different levels of accuracy for the different types of data or predictors for the different geo-referenced regions. In another implementation, system 1320 may prompt an operator to input weighting selections, wherein the operator chooses the extent to which each of the yield predictions from each of the multiple different types of pre-harvest weighting data contributes to the final yield estimate for the particular geo-referenced region and the aggregate yield allocation weighting value assigned to the particular geo-referenced region.

Figure 20:
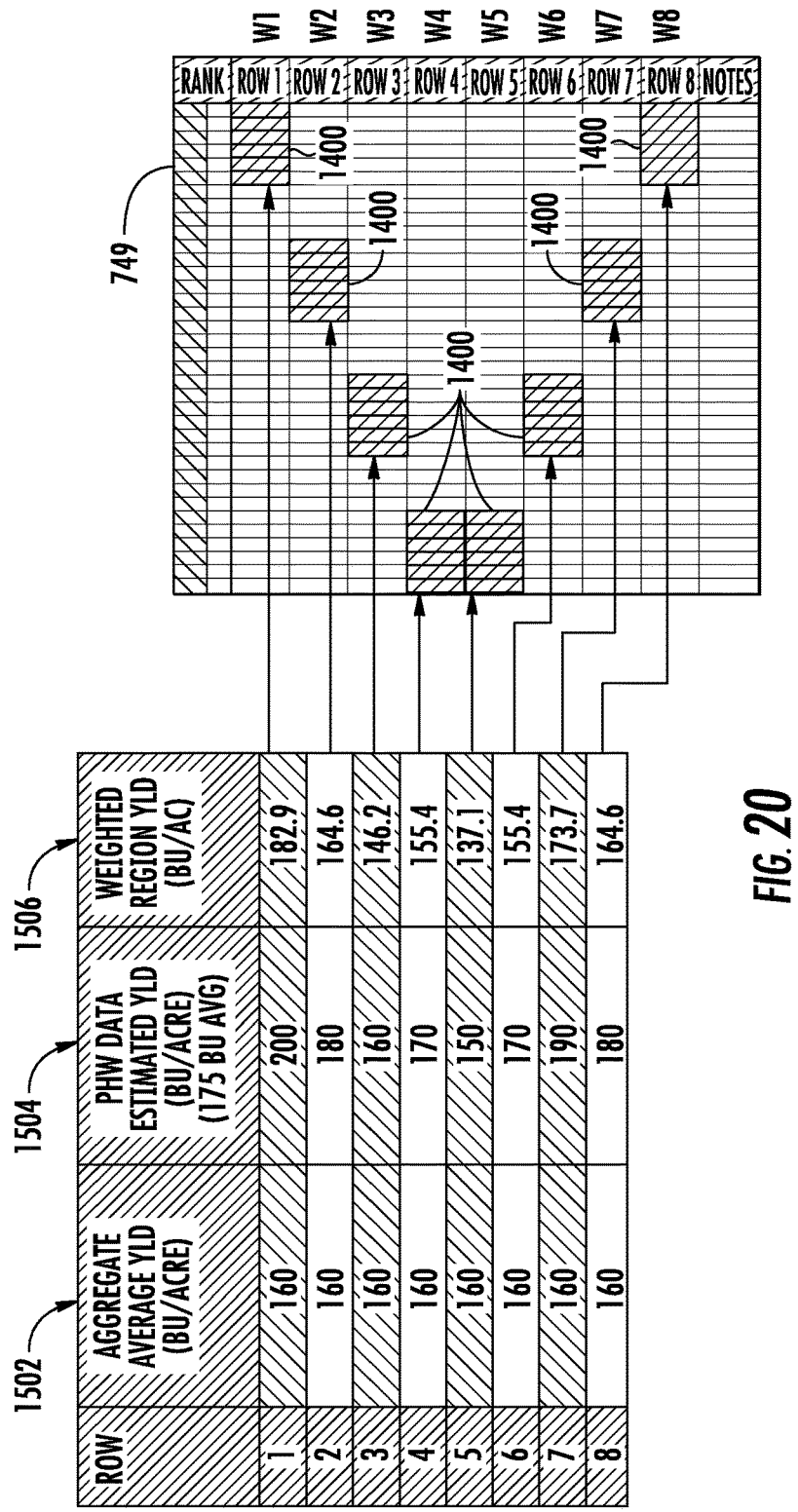
FIG. 20 is the diagram illustrating an example of weighted allocation of aggregate yield to geo-referenced regions based upon example preharvest weighting data.

FIG. 20 illustrates an example weighting of aggregate yield allocations to different geo-referenced regions being harvested using one or more of the pre-harvest weighting data. In the example illustrated in FIG. 20, aggregate yield for the shaded sub-regions 1400 of rows 1-8 of FIG. 10 is 160 bushels per acre as indicated in column 1502. The different pre-harvest weighting data based yield estimates for each of the sub-regions are shown in column 1504. In some implementations, the pre-harvest weighting data values in column 1504 for each of the sub-regions is the result of an aggregation or combination of multiple yield estimates from different types of pre-harvest weighting data, whether equally weighted or differently weighted. In the example, the pre-harvest weighting data average for the sub-regions is 175 bushels per acre. The weighted data yield for each region is 160*PHW/175, where PHW i is the preharvest weighting data based yield estimate for row i. The weighted preharvest weighting data yield for each of the eight sub-regions in the example are listed in column 1506. In one implementation, a pre-harvest weighting data based yield map, mapping different pre-harvest weighting data and/or corresponding yield estimates for different geo-referenced regions, is stored in polygons or vector, raster elements or other suitable formats. If a harvested region to be weighted spans more than one polygon/raster element, a weighting may be determined by, for example, using a weighted average, by area, of the spanned polygons or raster elements.

As described above, FIG. 19 illustrates a sampling of different types of pre-harvest weighting data. In one example, crop height data 1340 comprises data pertaining to the height of the crop at one time or at multiple different times during growth, prior to harvest. In one implementation, such data is obtained during activities during growth of the plants, such as during the application of herbicide, insecticide or fertilizer or cultivation. In other implementations, such data is obtained through aerial unmanned or manned vehicles by which images of the crop are captured during growth of the crop prior to harvest. Difference in height of the crops in the different geo-referenced regions are deemed to correlate to differences in yield from which system 1320 determined different yield allocation weightings for the different geo-referenced regions.

In one example, variety data 1342 refers to the variety of the crop. For example, some varieties are deemed to have different yield expectations as compared to other varieties. In one implementation, such data is obtained through historical records and/or from seed suppliers. The differences in the yield expectations for the different varieties are used by system 1320 to determine different yield allocation weightings for the different geo-referenced regions in which different yields of the crops are planted.

In one example, time interval distributions 1344 refers to the intervals of time or to the distribution of intervals of time from planting of the crop in a particular geo-referenced region to emergence of the crop or some other plant growth stage in the geo-referenced region. In one implementation, such data is obtained during activities during growth of the plants, such as during the application of herbicide, insecticide or fertilizer or cultivation. In other implementations, such data is obtained through recordation of planting times and aerial unmanned or manned vehicles by which images are captured over time indicating when the crop emerges. Differences in the intervals of time or distributions of the time intervals are deemed to correlate to different yields, wherein system 1320 utilizes the differences in predicted yields to determine and assign different yield allocation weightings to the different geo-referenced regions.

In one example, weed, pest and/or disease data 1346 refers to differences in the prevalence or degree of weed, pest and/or disease infestation amongst the different geo-referenced regions. In one implementation, such data is obtained during activities during growth of the plants, such as during the application of herbicide, insecticide or fertilizer or cultivation. In other implementations, such data is obtained through aerial unmanned or manned vehicles by which images of the crop are captured during growth of the crop prior to harvest. In one implementation, system 1320 will assign a geo-referenced region having a high degree of infestation of weeds, pest or disease with a lower yield allocation weighting as compared to the yield allocation weightings assigned by system 1320 to other geo-referenced regions having a lesser degree of infestation of weeds or pests or disease.

In one example, evapotranspiration data 1348 refers to the timing and rate at which moisture or water is transferred from each individual geo-referenced region to the air or atmosphere through evaporation from the soil and by transpiration from the crops or plants. Such data may be obtained through the use of local or field positioned evapotranspiration sensors or through the use of airborne or satellite remote evapotranspiration sensors. In one implementation, system 1320 correlates differences in evapotranspiration amongst the different geo-referenced regions to different predicted yields according to historical correlation data or formulas, wherein system 1320 further assigns different allocation weightings to the different geo-referenced regions based upon the different predicted yields.

In one example, soil moisture data 1350 refers to differences in the level of soil moisture in the different geo-referenced regions at a particular measurement time or at multiple different measurement times during growth of the crop. Such data may be obtained through various soil moisture sensors, whether local field position sensors or aerial or satellite sensors. Based upon differences in soil moisture or the amount of soil moisture at particular growth stages of the crops in the different geo-referenced regions, system 1320 determines a predicted yield or a predicted yield relationship between the different geo-referenced regions. System 1320 assigns different aggregate yield allocations to the different geo-referenced regions based upon the different predicted yields or yield relationships predicted from the determined soil moisture differences.

In one example, system 1320 utilizes on plant sensed data 1352 as a basis for assigned different aggregate yield allocations to the different geo-referenced regions. For example, in one implementation, on-plant sensors are provided on each plant or a sample of plants within each geo-referenced region. Data is obtained and stored from such on-plant sensors. In one implementation, system 1320 predicts yield differences or yield relationships between different geo-referenced regions based upon the different on-plant sensor data retrieved from the different geo-referenced regions. In another implementation, such predicted yield differences or yield relationships are determined by an outside provider, wherein the predicted yield differences or yield relationships are supplied to system 1320. Examples of such on-plant sensors include, but are not limited to sensors that measure light intensity, soil moisture, fertilizer conditions, soil consistency, humidity and temperature, stem diameter, leaf size, leaf moisture, turgidity, plant hormone levels, and plant color.

In one example, canopy temperature data 1354 refers to the sensed temperature of the canopy of the crop across the different geo-referenced regions. Canopy temperature is a direct measure of the energy released by plant and/or water stress of the plant. In one implementation, such canopy temperature may be sensed or monitored through the use of local, overhead or aerial infrared temperature or sensors or infrared thermometry systems. Such canopy temperature provides information on water status, water use and how a plant is functioning metabolically. Monitoring a canopy temperature facilitates the determination of heat unit accumulation. In one implementation, such canopy temperature or variations in canopy temperature across the different geo-referenced regions may indicate or predict different crop yields for the different geo-referenced regions. In one implementation, canopy temperature may be estimated as a function of ambient air temperature. The ambient air temperature may be measured near the geo-referenced regions or based on measurements at one or more remote locations. In one implementation, based upon the predicted differences in crop yield due to the sensed and recorded differences in canopy temperatures taken at one or more times or stages of growth of the crop, prior to harvest, system 1320 assigns different aggregate yield allocation weightings to the different geo-referenced regions.

In one example, shade avoidance data 1356 refers to data reflecting differences in predicted yield for different geo-referenced regions due to the phenomenon of shade avoidance. Evidence suggests that crop yield is sometimes reduced by the presence of weeds at the earliest vegetative states through a shade avoidance effect. Plants detect green light reflected by the nearby plants and respond to avoid the shade. Such plants respond by directing more resources to growing the plant tall at the expense of growing roots deep. The shallower roots may impact subsequent yield by limiting the plant's ability to access moisture and nutrients deeper in the soil.

In one implementation, shadow avoidance data 1356 is acquired through periodic collection, such as daily collection, of field images following planting. Such field images are processed to generate ortho-rectified, geo-referenced vegetation maps showing emerged crop and other vegetation. Plants which are crop are identified in images based on an as-planted map, likelihood of being in a row of crop and thus a crop plant, leaf spectral reflectance, leaf shape and other presently developed or future technologies. Other plants in such images are assumed to be weeds or they may be explicitly identified as a weed or specific weed species through spectral reflectance, leaf shape and other presently developed or future developed technologies. In some implementations, data from LIDAR or stereo camera are used to measure a crop and weed height. In some implementations, height is also used as a factor in estimating crop yield impact from weeds along with weed species, and crop variety, wherein different crop varieties may have different susceptibilities to shade avoidance effect.

Figure 21:
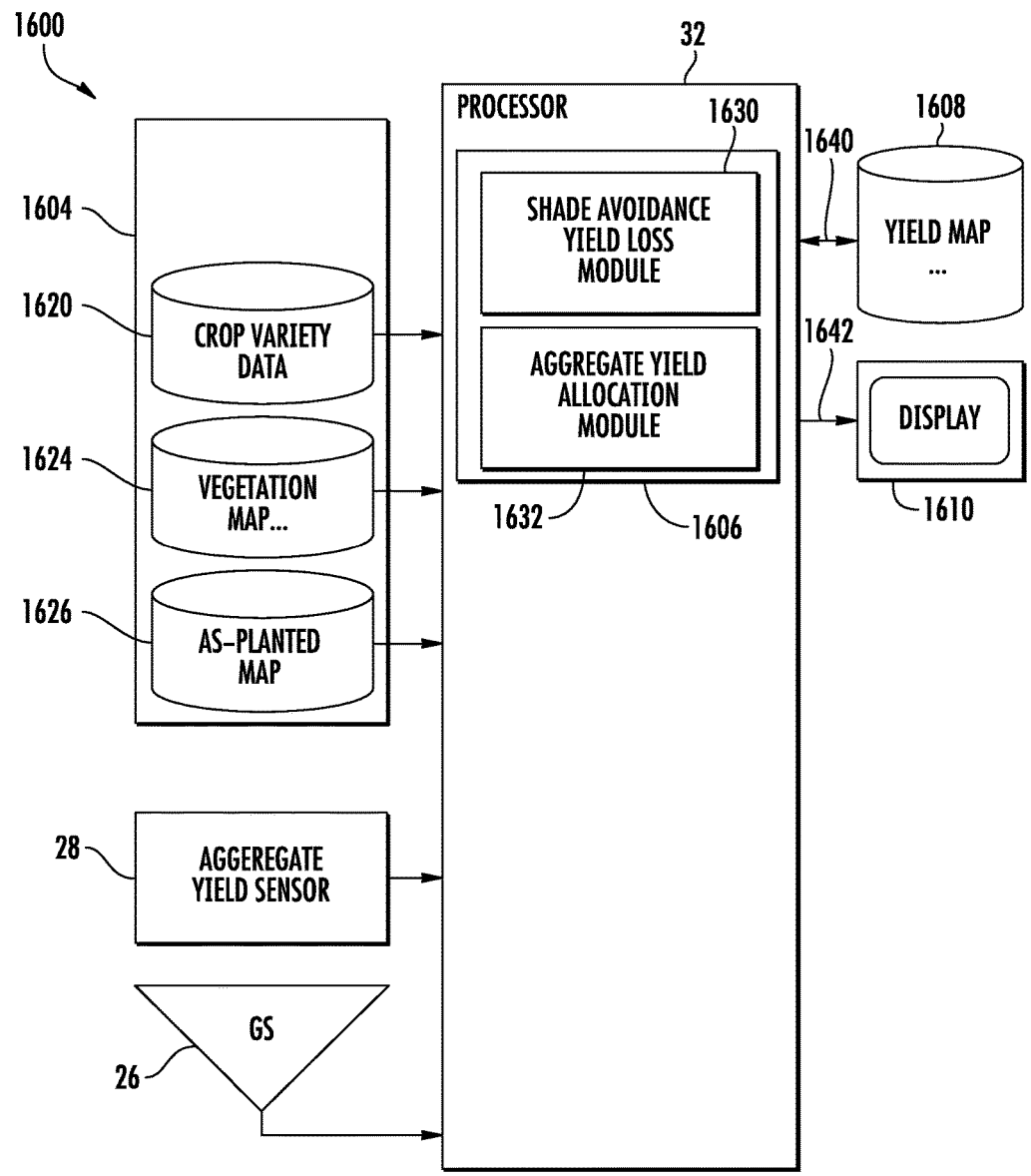
FIG. 21 is a schematic diagram of an example shade avoidance aggregate yield allocation weightings system.
Figure 22:
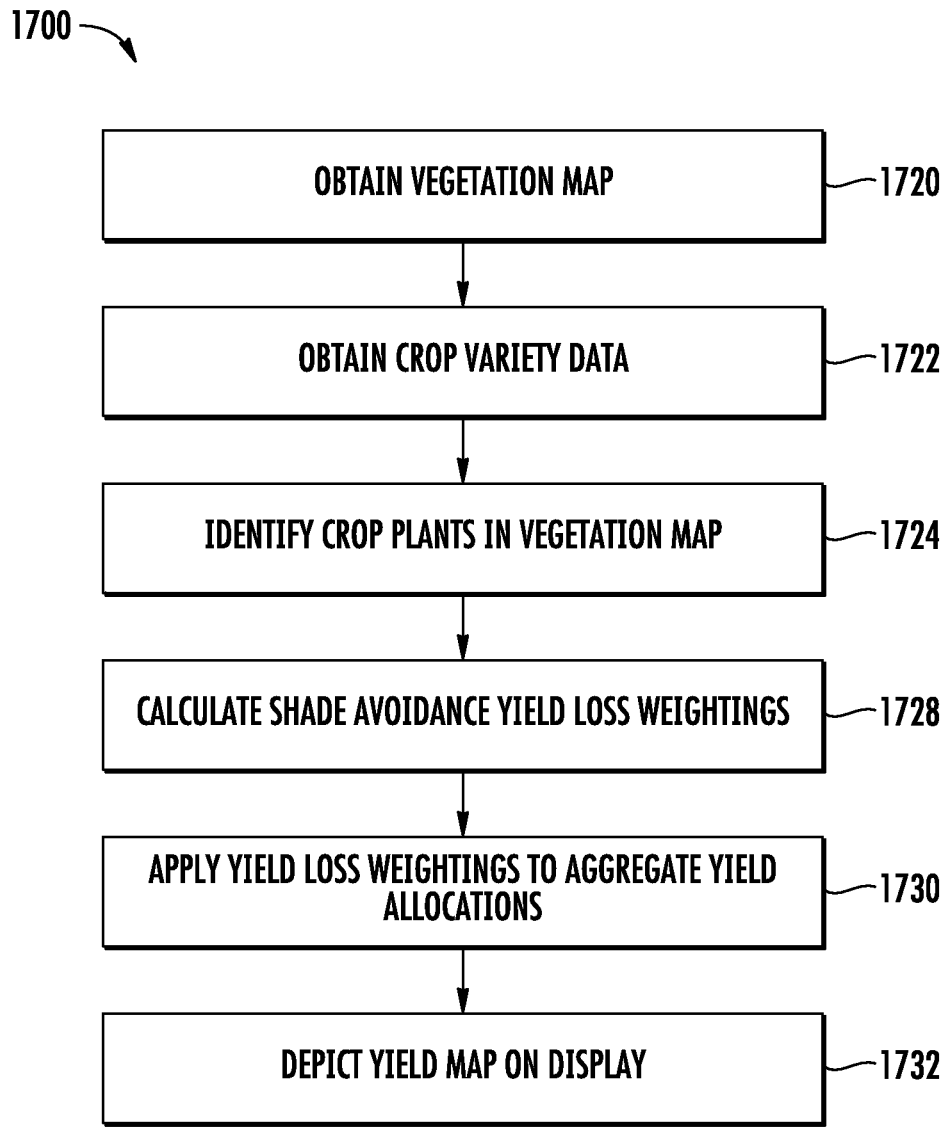
FIG. 22 is a flow diagram of an example method for weighting the allocation of aggregate yield based upon shade avoidance loss weightings.

FIG. 21 schematically illustrates an example shade avoidance aggregate yield allocation weighting system 1600 for using shade avoidance data 1356 to differently weight the allocation of aggregate yield amongst different geo-referenced regions based upon differences in shaded avoidance data from the different geo-referenced regions. In one implementation, system 1600 is incorporated or integrated into system 1320 described above. System 1600 comprises geo-referencing system 26, aggregate yield sensor 28, data sources 1604, processor 32, described above, instructions 1606, yield map data stored 1608 and display 1610.

Geo-referencing system 26, aggregate yield sensor 28 and processor 32 are each described above. Data sources 1604 comprise databases from which processor 32, following instructions 1606, retrieve data for determining shade avoidance yield loss weightings. In one implementation, data sources 1604 are local with respect to processor 32. In one implementation, data sources 1604 and processor 32 are local with respect to harvester 22, being carried by harvester 22. In another implementation, data sources 1604 and processor 32 are remote with respect to harvester 22, communicating in a wireless fashion with harvester 22. It still other implementations, processor 32 is local with respect to harvester 22, being carried by harvester 22, while data sources 1604 are remote with respect to harvester 22, communicating with harvester 22 in a wireless fashion. In some implementations, processor 32 and portions of data sources 1604 are distributed amongst multiple local and/or remote locations.

Data sources 1604 comprise crop variety data 1620, vegetation map 1624 and as planted map 1626. Crop variety data 1620 comprises a database of information regarding the particular variety or varieties of crop planted in the regions geo-referenced by geo-referencing system 26. Such data assists in identifying or distinguishing crops from extraneous vegetation. In one implementation, crop variety data 1620 provides historical data with respect to anticipated yield losses for different amounts of vegetation in the vicinity of a crop plant of a particular variety of the crop. Such information may be provided in the form of an equation, algorithm, model or other suitable form.

Vegetation map 1624 comprises a map or image of the geo-referenced regions and the vegetation in such geo-referenced regions, including both crop plants and extraneous vegetation, such as weeds. In one implementation, the vegetation map is generated based upon images captured at one or more times or at one or more different growth stages of the crop during the growing season prior to harvest. The vegetation map is stored for subsequent aggregate yield allocations during harvest of the crop. In one implementation, such images are captured by aerial or other overhead image capturing devices such as unmanned aerial vehicles, manned aircraft, balloon, satellite or other aerial vehicles. In other implementations, vegetation map 1624 is obtained from a camera mounted on a manned ground vehicle or through manual crop scouting. In one implementation, the vegetation map is ortho-rectified and geo-referenced.

As planted map 1624 comprises a map identifying planting characteristics of the different geo-referenced regions. In one implementation, as planted 1624 includes data indicating the varieties of the crop plants planted as well the spacing of such crop plantings. In some implementations, the as planted map 1624 further includes additional historical data such as levels of fertilizer, insecticide or herbicide applied to each of the different geo-referenced regions. In some implementations, as planted map 1624 is omitted.

Instruction 1606 comprise instructions or programmed logic contained on a non-transitory computer-readable medium or memory. Instruction 1606 comprise shade avoidance yield loss module 1630 and aggregate yield allocation module 1632. Shade avoidance yield loss module 1630 directs processor 32 in the estimation of shade avoidance yield losses for each of the different geo-referenced regions. Aggregate yield allocation module 1632 directs processor 32 in the allocation of a sensed aggregate yield to the different geo-referenced regions, wherein the allocation of the sense aggregate yield is based upon different travel time for crops to travel to the aggregate yield sensor 28 and different shade avoidance yield loss weightings for the different geo-referenced regions, such as according to method 300 described above.

In one implementation, modules 1630 and 1632 cooperate to direct processor 32 to carry out the example method 1700 outlined in FIG. 21. As indicated by block 1720, model 1630 directs processor 32 to access data store 1600 and obtain a vegetation map 1624 of the geo-referenced regions being harvested. As indicated by block 1722, module 1630 further directs processor 32 to acquire crop variety data by accessing crop variety data 1620 of data sources 1600. As indicated by block 1724, module 1630 further directs processor 32 to identify crop plants in the retrieved vegetation map. In other words, module 1630 direct processor 32 to distinguish crop plants from non-crop plants or extraneous plants, such as weeds. In one implementation, processor 32 utilizes the crop variety data in identifying crop plants in the retrieved vegetation map. In one implementation, processor 32 utilizes the as-planted map to identify crop plants from non-crop plants. For example, once processor 32 identifies a first crop plant, processor 32 utilizes the stored spacing between the planting of the crop plants to assist in positively identifying additional crop plants which will have the same planted spacing with respect to the first crop plant.

In some implementations, the identification of crop plants in the vegetation map is further achieved based upon the likelihood of being in a row of crop and thus a crop plant, leaf spectral reflectance, leaf shape and other criteria. Plants not identified as crop plants identified as weeds by processor 32. In yet other implementations, processor 32 additionally or alternatively positively identifies weeds or weed species through leaf spectral reflectance, leaf shape and other criteria, wherein plants not identified as weeds are deemed as more likely to be crop plants.

As indicated by block 1728, module 1630 uses the identification of crop plants in the vegetation map to calculate shade avoidance yield loss weightings. In one implementation, processor 32 utilizes a detailed 3-D ray tracing model of light from the sun, to weeds, to nearby crop plants to calculate how much green light is reflected from weed leaves to the crop plant. Weed leaf size and position are considered in such an approach. In another implementation, processor 32 determines the amount of green light based on a sum of a function applied to all weed leaves in a region of interest, wherein the function considers the area of each weed, centroid location, and the distance from the weed centroid to the centroid of the crop plant receiving its light. In one implementation, the area of each weed, centroid location, and the distance from the weed centroid to the centroid of the crop plant receiving its light are directly based on a 2-D analysis of the vegetation map.

Figure 23:
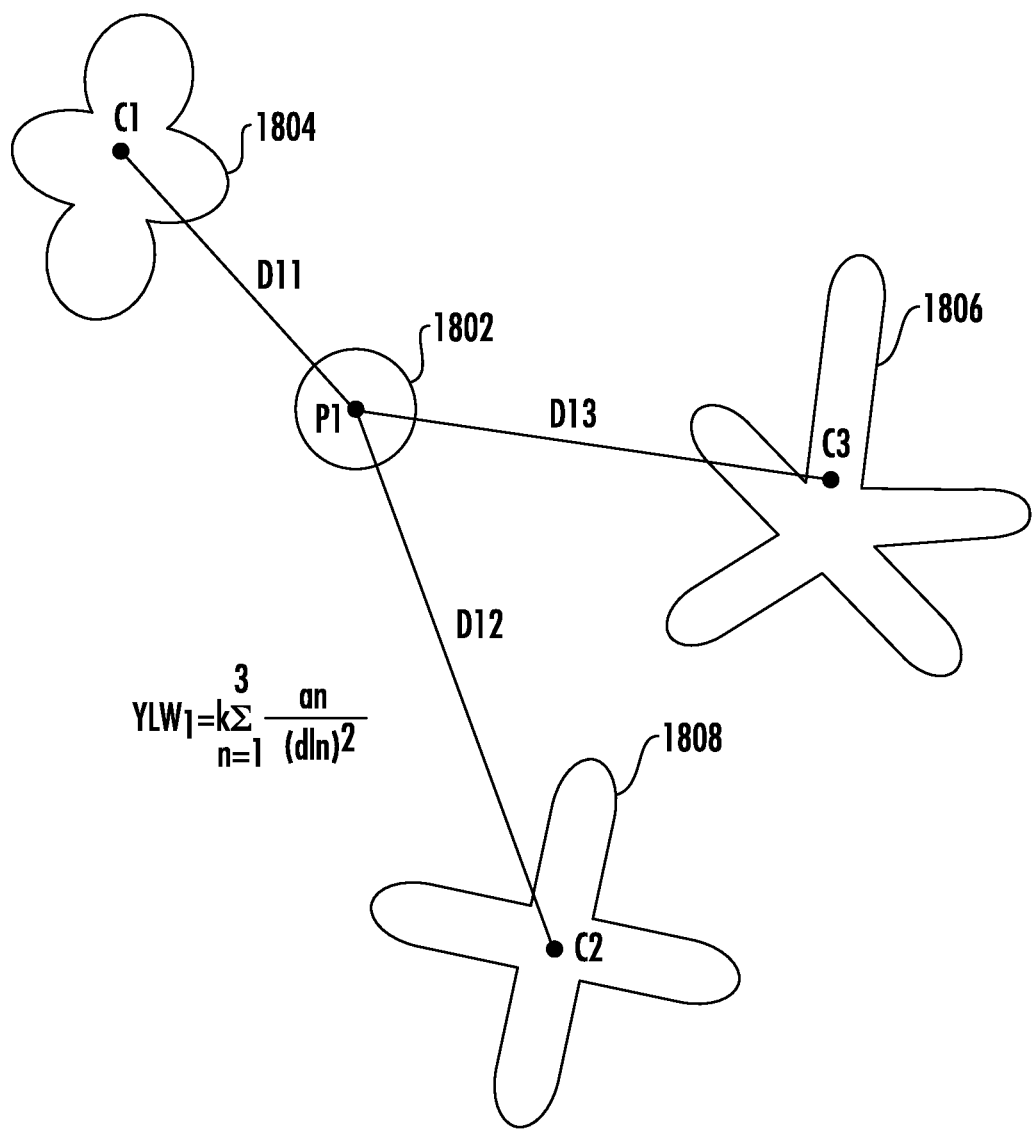
FIG. 23 is diagram illustrating an example method for determining shade loss for a crop plant.

FIG. 23 illustrates one example of the calculation of shade avoidance yield loss weightings by processor 32 following the instructions provided by module 1630. As shown by FIG. 23, in the example illustrated, crop plant P1 1802 has three weeds 1804, 1806 and 1808 in close proximity. Weeds 1804, 1806 and 1808 have centroids C1, C2 and C3; areas a1, a2 and a3; and distances d11, d12 and d13 from each respective centroid to the centroid of plant 1802, respectively. In the example illustrated, module 1630 directs processor 32 to determine shade avoidance yield loss weightings as a function of the area of each weed, and the distance from each weed centroid to a centroid of plant 1802. In the example illustrated, the shade avoidance yield loss weightings for plant P1 1802 (YLW$_1$) is YLW=K*SUM n=1 to 3 of $(a_n/(d_{1n})^2)$, where K is a constant for the crop variety which is retrieved from the crop variety data. K represents a susceptibility and magnitude of the shade avoidance and gives the crop avoidance yield loss weighting (YLW) the proper units for later calculations.

Figure 24:
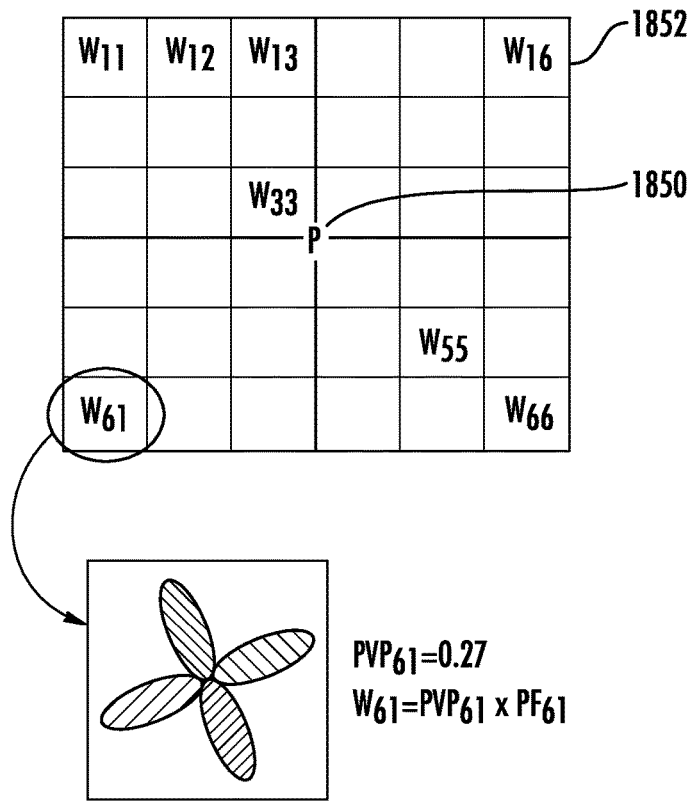
FIG. 24 is a diagram illustrating application of an example grid as part of an example method for calculating shade loss for a crop plant

FIG. 24 illustrates another example method by which processes 32, under the direction of module 1630, determines shade avoidance yield loss weightings. As shown by FIG. 24, in the example illustrated, numeric computation is reduced using a grid-centered on each crop plant P 1850. For each element of the grid 1852, a yield reduction weighting Wrc is calculated as a percentage of the vegetative pixels PVPrc in each element which is multiplied by a plant factor PRrc which is part of the crop variety data. The plant factor takes into account shade avoidance response for the crop variety in the distance of the respective grid element from the plant 1850. The rc subscripts are for the row and column of each grid element, respectively. Under this approach, the yield reduction weighting Wrc for each grid element is calculated according to the formula Wrc=PVPrc*PFrc. PVPrc, like k, for select weeds and crop varieties, is determined empirically through, for example, laboratory experimentation, wherein crop plants are planted in a normal pattern with weeds growing in one or more grid cells. The effect of shade avoidance invoked by the weeds for nearby crop plants is compared to yield of control plants which you not receive green light reflected by the weed leaves.

Recognizing that yield reduction from shallow roots resulting from the shade avoidance response may be more severe in dry years than wet years as well as more severe in high areas than low areas, other equations or factors may be used to calculate Wrc. For example, in one implementation, the following more detailed formula is used by processor 32 to calculate shade avoidance yield loss weightings: Wrc=PVPrc*PFrc*LSPrc*R, wherein LSPrc is a landscape or topological position factor and R is a rainfall factor for the season (shown in the particular example is being a constant for the field). In one implementation, the shade avoidance yield loss weightings for each individual plant are then summed for all the plants in a particular geo-referenced region to determine the shade avoidance yield loss weighting for the particular geo-referenced region.

Figure 25:
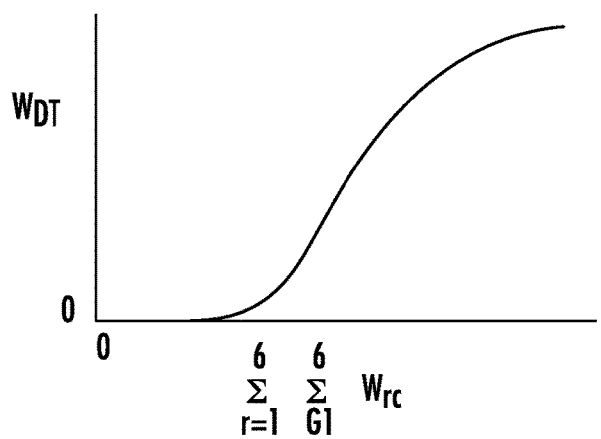
FIG. 25 is a graph illustrating determination of shade loss for a crop plant by summing shade loss of grid elements of the grid of FIG. 24 according to a sigmoid function.

In one implementation using the approach described with respect to FIG. 24, the shade avoidance yield loss weighting for each plant is a sum of the weightings for all the grid elements. In another implementation, as shown by FIG. 25, under the approach described with respect to FIG. 24, the shade avoidance yield loss weighting for each plant is calculated using more complex functions such as a sigmoid function. In one implementation, the shade avoidance yield loss weightings for each individual plant are then summed for all the plants in a particular geo-referenced region to determine the shade avoidance yield loss weighting for the particular geo-referenced region.

In some implementations, the as-planted map is not available or image processing is not performed to identify crop plant locations in the vegetation map. In such circumstances, this lack of actual plant location is handled by using a pseudo-plant location with map rows and appropriate seed intervals the plant population in row spacing.

As indicated by block 1730 in FIG. 21, aggregate yield allocation model 1632 (shown in FIG. 21) utilizes the shade avoidance yield loss determinations for each of the geo-referenced regions to differently weight the aggregate yield allocations amongst the different geo-referenced regions. Aggregate yield allocation model 1632 allocates each of the geo-referenced regions and aggregate yield portion allocation based upon different travel time for crops to the aggregate yield sensor and differences in the shade avoidance yield loss weightings for each of the different geo-referenced regions. As noted above, in some implementations, additional data is used in conjunction with the shade avoidance yield loss weight data to differently weight the aggregate yield allocations amongst the different geo-referenced regions. For example, in one implementation, aggregate yield allocation module 1632 may direct processor 32 to weight the allocations of the aggregate yield amongst the different geo-referenced regions based on a combination of shade loss avoidance data and any of the other pre-harvest weighting data types, such as those shown in FIG. 19.

As indicated by block 1732 in FIG. 21, aggregate yield allocation module 1632 outputs the aggregate yield portion allocations. As indicated by arrow 1640 in FIG. 21, module 1632 direct processor 32 to output such aggregate yield portion allocations to a database that stores yield map 1608. As indicated by arrow 1642 in FIG. 21, in one implementation, module 1632 directs processor 32 to present the yield map on display 1610. In one implementation, display 1610 is connected to processor 32 via a wired or wireless connection. In some implementations, display 1610 is wearable, handheld, vehicle mounted, part of a tablet or part of a personal computer or any other suitable display device. In some implementations, display 1610 comprises a surface onto which an image is projected.

In some implementations, different yields amongst the different geo-referenced regions, resulting from the different aggregate yield allocations, are assigned a color that is presented on display 1610, wherein each assigned color indicates the number of bushels or in what range of yield within which the actual yield falls. In other implementations, the different yields of the different geo-referenced regions are depicted with different patterns, such as blanks, dashes, and the like. In other implementations, different yields are depicted in different grayscale on display 1610. In some implementations, different yields are assigned a proportional height above a plane in a 3-D view of the field being presented on display 1610. In some implementations, two or more representation tactics are employed, such as color and height above a plane or color and pattern. In some implementations, color is employed to represent aggregate yield for an area with intensity used to depict higher resolution relative yield. In still other implementations, processor 32 utilizes existing market prices to calculate and display a depiction of all or a portion of a field with units of "dollars lost" from shade avoidance. For example, using such shade avoidance yield loss data, processor 32 determines such loss based upon the number of bushels per acre of your loss multiplied by the crop selling price per bushel in the acres per region.

Figure 26:
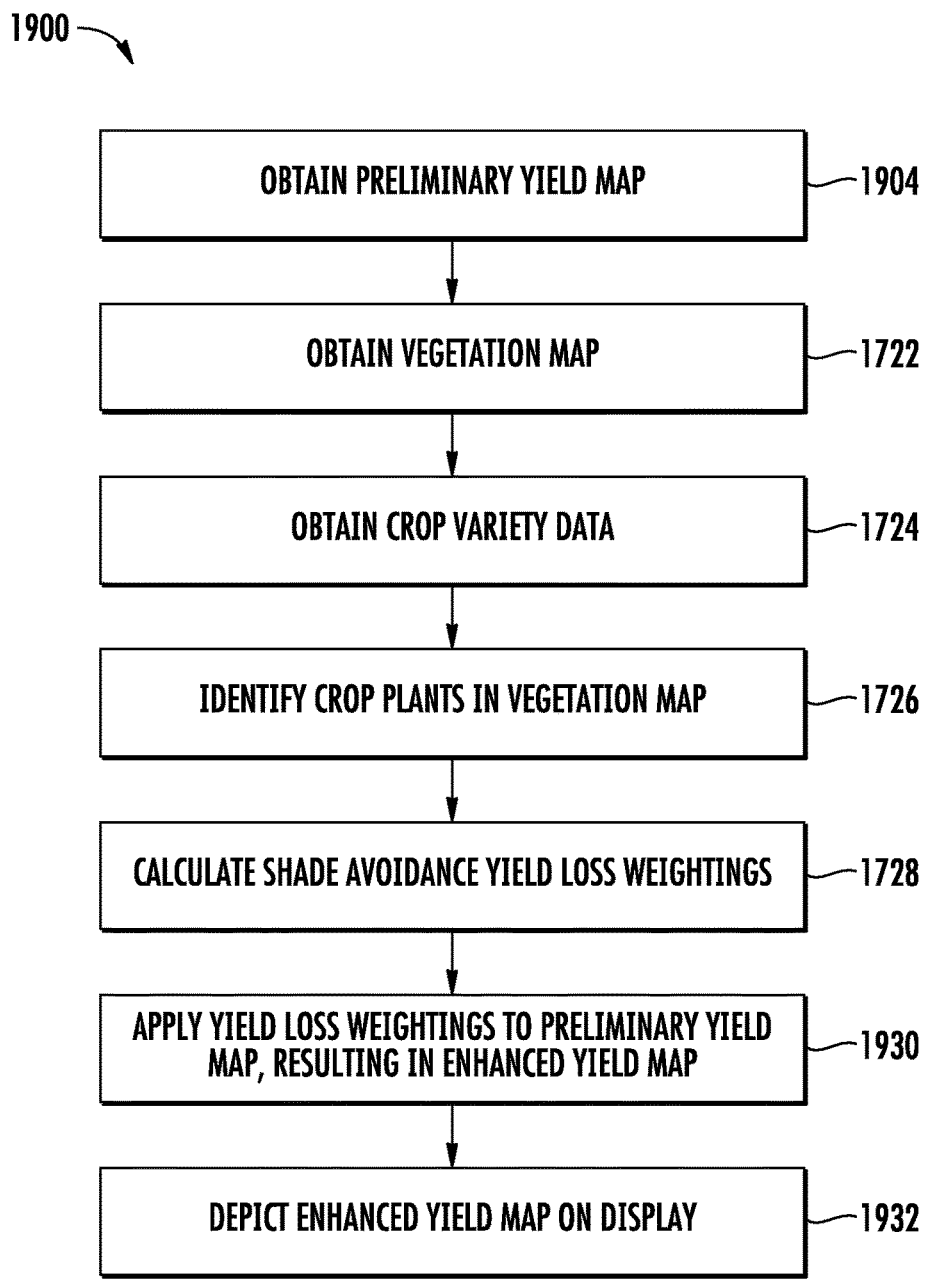
FIG. 26 is a flow diagram of an example method for generating an enhanced yield map based upon shade avoidance loss weightings.

Although methods for determining and applying shade avoidance yield loss data are described for differently weighting the allocations of aggregate yield amongst different geo-referenced regions that are based upon different travel times for crops to an aggregate yield sensor, in other implementations, the same methods may, in other implementations, be used to enhance an existing or preliminary yield map. FIG. 26 illustrates an example method 1900 which produces and displays an enhanced yield map using calculated shade avoidance yield loss weightings. In the example illustrated, method 1900 is carried out by the system 1600 shown and described with respect to FIG. 21 without the use of or provision of geo-referencing system 26, aggregate yield sensor 28 or aggregate yield allocation module 1632. Those steps of method 1900 correspond to steps of method 1700 are numbered similarly.

As indicated by block 1904, module 1630 directs processor 32 to obtain a preliminary yield map. The preliminary mail map comprises a map of multiple geo-referenced regions of a field to which have been assigned preliminary or initial crop yield values. In one implementation, the preliminary yield map includes resolution units having a width of a crop harvester head and a length that is a distance or time interval of travel by the harvester. In implementations, vegetation map 1624 is at a finer resolution, wherein the enhanced yield map resulting from the modification of the preliminary yield map by method 1900 and the resolution is equal to or between the resolution of the preliminary yield map and the vegetation map 1624.

As further illustrated indicated by blocks 1722, 1724, 1726 and 1728 in FIG. 26, method 1900 carries out the same corresponding steps as described above with respect to method 1700. In particular, module 1630 directs processor 32 to obtain a vegetation map, obtain crop variety data 1620, identify crop plants in the vegetation map and calculate shade avoidance yield loss weightings.

As indicated by block 1930, processor 32, following instructions provided by module 1630, applies the determined shade avoidance yield loss weightings for the individual plants in each resolution unit of the preliminary yield map. In one implementation, the preliminary yield map comprises yield data representing an average yield in a defined area (the resolution of the preliminary yield map), wherein the area is at a coarser resolution than the shade avoidance yield loss weight, all the Wtot's. As a result, average yield in each defined area is spatially redistributed in the area to provide higher resolution yield estimates within the defined area. As indicated by block 1932, the enhanced yield map is then stored in database 1608 and/or presented on display 1610 as described above.

FIG. 27 schematically illustrates crop sensing system 2020, an example implementation of system 1320. System 2020 is similar to system 820 described above except that system 2020 additionally comprises crop sensors 2036A-2036H (collectively referred to as crop sensors 2036). In addition, system 2020 is specifically illustrated as comprising geo-referencing system 26, aggregate yield sensor(s) 28, aggregate yield module 50, yield allocation module 52, yield mapping module 56 and pitch/roll sensors 86, 88 (each of which are described above with respect to system 20) which carry out method 300 (described above in FIG. 4), wherein the region weightings in block 314 of FIG. 4 comprise weightings based upon different yield estimates for the different geo-referenced regions from the following example yield estimation mechanisms: (1) data and/or signals from sensors 836 which are based upon power for each of the portions of harvester head 834; (2) data and/or signals from crop sensors 2036 which are based upon directly sensed attributes of the crops in each of the geo-referenced regions as such crops are being harvested; and/or (3) one or more pre-harvest weighting data 1336, such as crop height data 1340, variety data 1342, time interval distribution data 1344, weed/past/disease data 1346, evapotranspiration data 1348, soil moisture data 1350, on plant sense data 1352, canopy temperature data 1354 and/or shade avoidance data 1356. As described above, in some implementations, multiple weighting bases or yield estimation mechanisms are combined in equally or differently weighted manners to determine the different allocation weightings.

As described in more detail above, in some implementations, different weighting bases or yield estimation mechanisms are used for differently weighting aggregate yield allocations based upon the particular geo-referenced region or regions. For example, in one implementation, a first one or a first set of the above-described yield estimation mechanisms are used for weighting aggregate yield allocations for a first geo-referenced region while the second different one or a second different set of the above-described yield estimation mechanisms are used for weighting aggregate yield allocations for a second geo-referenced region.

Moreover, as described in more detail above, in some implementations, even though the same yield estimation mechanisms are used across different geo-referenced regions, the same yield estimation mechanisms may have different relative weights when combined based upon the particular geo-referenced region to which the yield estimation mechanisms are being applied. For example, in one implementation, even though two geo-referenced regions have aggregate yield allocations that are weighted based upon the same first and second yield estimation mechanisms, system 2020 applies a greater relative weight to the first yield estimation mechanism on one of the geo-referenced regions while applying a greater relative weight to the second yield estimation mechanism on the other of the geo-referenced regions.

Although system 2020 is illustrated as providing an operator with the ability to choose from different operational modes, wherein the operator selects any one or any combination of the described yield estimation mechanisms or wherein system 2020 automatically chooses from amongst the above-described yield estimation mechanisms, in other implementations, system 2020 utilizes less than each of the above-described yield estimation mechanisms. In some implementations, system 2020 may utilize additional or alternative yield estimation mechanisms when differently weighting the allocation of aggregate yield amongst the different geo-referenced regions based upon travel time of crops to the aggregate yield sensor.

Crop sensors 2036 comprise sensors that directly sense one or more attributes of the crops as a crops are being harvested by harvester 820. Crop sensors 2036 output signals indicating one or more characteristics of individual plants being harvested or groups of plants as they are being harvested. In such an implementation, yield allocation module 52 utilizes such signals to identify or predict yield differences between different plants and/or different groups of plants being harvested by the different portions, row units, of harvester 820. In one implementation, each of the row units includes a designated one of sensors 2036. In another implementation, multiple row units, forming different subsets of the entire set of row units share a sensor 2036. Based upon the predicted yield differences, yield allocation model 52 adjusts the allocation or apportionment of the aggregate yield amongst the different geo-referenced regions from which plants were harvested by the different row units.

In one implementation, each of sensors 2036 detects a diameter of each of the stalks of the plants being harvested from each of the geo-referenced regions by the different row units or groups of row units. One implementation, each of sensors 2036 is configured to detect the diameter of individual stalks. In such an implementation, yield allocation model 52 allocates aggregate yield from a particular measurement interval to each of the geo-referenced regions traversed by the different row unit using a weighting that is based upon the determined thickness of the plants harvested by each row unit. For example, two geo-referenced regions traversed by harvester 820 during the same measurement interval may receive different aggregate yield allocations due the stalks in one of the geo-referenced regions harvested by one of the row unit being thicker or wider than the stalks in the other of the geo-referenced regions harvested by other row unit, where the greater thickness of the stalk is determined as being linked to greater crop yield.

In one implementation, each of crop sensors 2036 comprises a sensor that interacts, engages or contacts the plants as the plants are being harvested, wherein such interaction results in signals indicating one or more characteristics of the plants being harvested. For example, in one implementation, each of sensors 2036 comprises a sensor that senses an impact of the crop, such as ears of corn, with harvester 820, such a stripper plate of harvester 820. In one implementation, each of sensors 2036 may comprise an auditory sensor or an accelerometer to detect the impact of the crop with harvester 820. In one implementation, larger or greater impacts producing higher amplitude signals indicate greater mass and are deemed as indicating greater yield. In such an implementation, two geo-referenced regions traversed by harvester 820 during the same measurement interval may receive different aggregate yield allocations from later measurement intervals due to differences in the sensed crop impacts being larger from plants in one geo-referenced region versus impacts from plants in another geo-referenced region. One example of such a crop impact detection system is disclosed in U.S. patent application Ser. No. 13/771,682 filed on Feb. 20, 2013 and entitled CROP SENSING; U.S. patent application Ser. No. 13/771,727 filed on Feb. 20, 2013 and entitled PER PLANT CROP SENSING RESOLUTION; U.S. patent application Ser. No. 13/771,760 filed on Feb. 20, 2013 and entitled CROP SENSING DISPLAY, the full disclosures of which are hereby incorporated by reference.

In one implementation, each of crop sensors 2036 comprises a sensor that detects one or more characteristics of the plants being harvested without contacting the plants being harvested. In such an implementation, such yield allocation weightings are based upon captured video or images of the plants during harvest. For example, in one implementation, each of sensors 2036 comprises a camera that captures images of the plants prior to engaging with harvester 820, wherein such images are analyzed and the results of such analysis is used to generate and apply yield allocation weightings. In one implementation, each of crop sensors 2036 comprises a camera or LIDAR that output signals indicating characteristics of the plants being harvested. In such implementations, yield allocation module 52 includes software, code or programmed logic to predict a yield for the different plants or groups of plants based upon signals from sensors 2036. In some implementations, images of other plant portions are used for yield allocation weightings using preselected or field calibrated conversion factors or both. For example, in other implementations, yield allocation weightings are based upon captured video or images of the size of the year at stripper plate or the size of the plant, wherein plant size correlates to plant mass which correlates to grain mass. In yet other implementations, such weightings are determined based upon other sensed characteristics of plants being harvested by harvester 820.

As described in more detail above, in one mode of operation, yield allocation module 52 additionally or alternatively utilizes a yield estimation mechanism based upon different power characteristic of each of different components 835 across a crop harvesting width of the harvester 820 as sensed by sensors 836, wherein yield allocation weightings for different plants in different geo-referenced regions are based upon the actual sensed power characteristics and/or differences in the sensed power characteristics of the different components across the harvesting width. For example, harvester 820 may be harvesting a first geo-referenced region with a first row unit or a group of row units and a second geo-referenced region at the same time with a different second row unit or a different second group of row units. Due to the first geo-referenced region providing a greater crop yield than the second geo-referenced region, the power consumed or otherwise employed to harvest the crops in the first geo-referenced region in many instances will be greater than the power consumed or otherwise employed to harvest the crops in the second geo-referenced region. As a result, the power consumed or employed by components of the first row unit or first group of row units to harvest the crops in the first geo-referenced region will likely be greater than the power consumed or employed by components of the second row unit or the second group of row units to harvest the crops in the second geo-referenced region. Harvester 820 utilizes sensors 836 across the harvesting width to sense a power characteristic associated with each of different components across the harvesting head and applies different yield allocation weightings to different geo-referenced regions based upon the actual sensed power characteristics and/or a relationship between the sensed power characteristics of the different components of the different individual row units or groups of row units.

Aggregate yield module 50 comprises software, code, circuitry and/or program logic providing instructions for directing processor 32 to determine an aggregate yield for each measurement interval based upon signals received from aggregate yield sensor 28. In one implementation, the aggregate yield for each measurement interval is based upon signals received from a gamma ray attenuation sensor, impact plate sensors, flow sensors, load sensors and/or optical sensors.

Yield allocation module 52 comprises software, code, circuitry and/or program logic providing instructions for directing processor 830 to allocate portions of the aggregate yield for a particular measurement interval to each of at least two geo-referenced regions that were traversed by harvester 820 prior to the particular measurement interval, wherein the allocation is based upon different amounts of time for crops to travel to aggregate yield sensor 820 after being initially separated from the growing medium or ground to aggregate yield sensor 28. In the example illustrated, the time for crops to travel from aggregation location to aggregate yield sensor 28 is the same for crops harvested from each of portions of harvester head 834. However, due to either different travel distances and/or different conveying speeds, reflected by the different travel times for the different transverse portions, crops removed by different transverse portions of header 34 during a particular measurement interval arrive at aggregate yield sensor 28 at different times after conclusion of the measurement interval. Yield allocation module 52 allocates the aggregate yield value for the measurement interval to different geo-referenced regions that were traversed or interacted upon by crop removal portions 40 prior to the measurement interval.

In addition, as indicated by blocks 314 and 316 of method 300 (shown in FIG. 4), yield allocation module 52 carries out such aggregate yield allocations based upon yield weightings or region weightings as determined based upon differences in yield estimations from one geo-referenced region to the next. Such yield estimations or region weightings are based upon one or more of the above-described yield estimation mechanisms. Yield mapping module 56 comprises software, code, circuitry and/or program logic providing instructions for directing processor 830 to map the allocation of aggregate yield to the different geo-referenced regions traversed by harvester 820. In one implementation, yield mapping module 56 records or stores the maps of yield for the different geo-referenced regions in a data storage 58. Data storage 58 comprises a data storage portion of memory 828. In one implementation, in addition to storing yield maps for the different geo-referenced regions, data storage 58 also stores additional data such as the aggregate yield for the different measurement intervals as well as earlier detected plant characteristics that are detected during the harvest of such plants or that are detected at earlier times prior to engagement of the plants by harvester 820, such as during herbicide, insecticide or fertilizer application, cultivation or overhead or aerial crop data collection. As noted above, in different implementations, data storage 58 is carried by harvester 820, at a location remote from harvester 820 and/or is distributed across different sites.

Although the present disclosure has been described with reference to example embodiments, workers skilled in the art will recognize that changes may be made in form and detail without departing from the spirit and scope of the claimed subject matter. For example, not every feature shown in drawings is required and one or more features may be omitted. Although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A method comprising:

receiving a first signal indicating an aggregate yield measured by an aggregate yield sensor during a measurement interval;

receiving a second signal indicating a plurality of geo-referenced regions across which a harvester has traveled prior to the measurement interval;

allocating, to each of at least two geo-referenced regions, an aggregate yield portion allocation based upon different travel times for crops to the aggregate yield sensor and pre-harvest weighting data value differences amongst the at least two geo-referenced regions; and outputting the aggregate yield portion allocations;

wherein the different travel times for crops to the aggregate yield sensor comprise different travel times for crops from different transverse portions of a width of a head of the harvester to the aggregate yield sensor and wherein different transverse portions comprise crop removal portions and crop conveyors, the crop conveyors to convey the crops to the aggregate yield sensor, the different travel times corresponding to different times for the crop conveyors to convey the crops from the different transverse portions to the aggregate yield sensor.

2. The method of claim 1, wherein the pre-harvest weighting data values are selected from a group of pre-harvest weighting data consisting of: shade avoidance data; crop variety data; time interval from planting to the emergence data; time interval distributions from planting to emergence; weed data; pest data; disease data evapotranspiration data; soil moisture data; on plant sensed data; canopy temperature data; and crop height data.

3. The method of claim 1, wherein the pre-harvest weighting data values comprise shade avoidance data.

4. The method of claim 1, wherein the pre-harvest weighting data values comprise growth stage time interval data.

5. The method of claim 1, wherein the pre-harvest weighting data values comprise a plurality of different types of pre-harvest weighting data.

6. The method of claim 1, wherein the pre-harvest weighting data values comprise comprises data from a plurality of growing seasons.

7. The method of claim 1, wherein the pre-harvest weighting data values comprise a plurality of different types of pre-harvest weighting data from a plurality of growing seasons.

8. The method of claim 1, wherein the pre-harvest weighting data values comprise a plurality of different types of pre-harvest weighting data and wherein the plurality of different types of pre-harvest weighting data are weighted relative to one another.

9. The method of claim 1 further comprising:
sensing a pitch of the harvester; and
allocating a portion of the aggregate yield to the plurality of geo-referenced regions based upon the pitch.

10. The method of claim 1 further comprising:
sensing a roll of the harvester; and
allocating a portion of the aggregate yield to the plurality of geo-referenced regions based upon the roll.

11. The method of claim 1 further comprising:
sensing an attribute of each of a plurality of plants harvested by and across the harvester; and
allocating the aggregate yield amongst the plurality of plants based upon the sensed attribute of each of the plurality of plants.

12. The method of claim 1 further comprising:
sensing different levels of power associated with different components of the harvester that interact with different plants across the harvester; and
allocating the aggregate yield amongst the different plants based upon the sensed different levels of power.

13. The method of claim 1, wherein the geo-referenced regions to which portions of the aggregate yield from the measured interval are allocated are part of a chevron shape.

14. The method of claim 1, wherein allocation of the portions of the aggregate yield from the measured interval to the plurality of geo-referenced regions is based upon a distance traveled by a harvested crop until being sensed by the aggregate yield sensor, conveyance speed applied by each conveyance subsystem and forward speed of the harvester head.

15. The method of claim 1, wherein the aggregate yield is allocated among sets of plants, each set being harvested by a different transverse portion of the harvester.

16. The method of claim 1 further comprising automatically adjusting operational settings of the harvester based upon the aggregate yield portion allocations.

17. The method of claim 1, wherein the allocating, to each of at least two geo-referenced regions, of the aggregate yield portion allocation is additionally based upon a measurement, selected from a group of measurements consisting of: a roll of the harvester; a pitch of the harvester; a sensed attribute of each of a plurality of plants being harvested; and sensed different levels of power associated with different components of the harvester that interact with different plants across a width of a head of the harvester.

* * * * *